US007247426B2

(12) United States Patent
Yakhini et al.

(10) Patent No.: US 7,247,426 B2
(45) Date of Patent: Jul. 24, 2007

(54) CLASSIFYING CANCERS

(75) Inventors: Zohar Yakhini, Yaacov (IL); Michael Bittner, Rockville, MD (US); Jeff Trent, Rockville, MD (US); Amir Ben-Dor, Bellevue, WA (US); Paul Meltzer, Rockville, MD (US); Yidong Chen, Rockville, MD (US); Ashani Weeraratna, Owings Mil, MD (US); Yuan Jiang, Gaithersburg, MD (US); Nick Sampas, San Jose, CA (US); Edward Dougherty, College Station, TX (US)

(73) Assignee: Agilent Technologies, Inc., Santa Clara, CA (US)

( * ) Notice: Subject to any disclaimer, the term of this patent is extended or adjusted under 35 U.S.C. 154(b) by 263 days.

(21) Appl. No.: 09/921,406

(22) Filed: Aug. 2, 2001

(65) Prior Publication Data

US 2003/0152923 A1   Aug. 14, 2003

(51) Int. Cl.
*C12Q 1/68* (2006.01)
(52) U.S. Cl. .................. 435/6; 436/64; 436/501; 436/518
(58) Field of Classification Search .................. 435/6, 435/7.23, 4; 436/64; 424/9.1
See application file for complete search history.

(56) References Cited

U.S. PATENT DOCUMENTS

| 6,025,137 A | 2/2000 | Shyjan ........................... 435/6 |
| 6,057,105 A | 5/2000 | Hoon et al. ..................... 435/6 |

OTHER PUBLICATIONS

Iozzo et al. (Cancer Research, vol. 55, pp. 3495-3499, 1995).*
Blanc et al. (Oncogene, 2005, vol. 24, pp. 1277-1283).*
Leris et al. (Anticancer Research, 2005, vol. 25, 2A, abstract).*
Hall et al., "Update on theIncidence and Mortality from Melanoma in the United States" J. Am. Acad. Dermatol. 40: 35-42, 1999.
Weyers et al., "Classification of Cutaneous Malignant Melanoma: A Reassessment of Histopathogic Criteria for the Distinction of Different Types" Cancer 86: 288-299, 1999.
Byers et al., "Pathologic Parameters in the Diagnosis and Progonis of Primary Cutaneous Melanoma" Hematol. Oncol. Clin. North Am. 12 : 717-735, 1998.
McMasters et al., "Recent Advances in Melanoma Staging and Therapy" Ann. Surg. Oncol. 6: 467-475, 1999.
Maniotis et al., "Vascular Channel Formation by Human Melanoma Cells in Vivo and in Vitro: Vasculogenic Mimicry" Am. J. Pathol. 155: 739-752, 1999.
DeRisi et al., "Use of a cDNA Microarrat to Analyse Gene Expression Patterns in Human Cancer", Nature Genet. 14: 457-460, 1996.
Khan et al., "Gene Expression Profiling of Alveolar Rhabdomyosarcoma with cDNA Microarrays" Caner Res. 58:5009-5013, 1998.

Perou et al., "Distinctive Gene Expression Patterns in Human Mammary Epithelial Cells and Breast Cancers" Proc. Natl. Sci. USA 96: 9212-9217, 1999.
Golub et al., "Molecular Classification of Cancer, Class Discovery and Class Prediction by Gene Expression Monitoring" Science 286: 531-537, 1999.
Alizadeh et al., "Distinct Typesof Diffuse Large B-Cell Lymphoma Identified by Gene Expression Profiling" Nature 403: 503-511, 2000.
Bittner et al., "Data Analysis and Integration of Steps and Arrows" Nature Genet. 22: 213-215, 1999.
Eisen et al., "Cluster Analysis and Display of Genome-Wide Expression Patterns" Proc. Natl. Acad. Sci USA, 95: 14863-14868, 1998.
Everitt, B. Applied Multivariant Data Analysis. (Oxford Univ. Press. New York, 1992).
Bittner, et al., "Molecular Classification of Cutaneous Malignant Melanoma by Gene Expression Profiling", Nature, 406: 536-539, 2000.
Adams "Characterization of Cell-Matrix Adhesion Requirements for the Formation of Fascin Microspikes" Mol. Biol. Cell 8:2345-2363, 1997.
Scott et al., "pp125FAK in Human Melanocytes and Melanome: Expression and Phosphorylation" Exp. Cell Res. 219: 197-203, 1995.
Jannji et al., "Autocrine TGF-Beta-Regulated Expression of Adhesion Receptors and Integrin-Linked Kinase in HT-144 Melanoma Cells Correlates with Their Metastic Phenotype" Int. J. Cancer 83: 255-262, 1999.
Hieken et al., "Beta1 Integrin Expression in Malignant Melanoma Predicts Occult Lymph Node Metastases" Surgery 118: 669-673, 1995.
Van Belle et al., "Progression-Related Expression of beta3 Intregrin in melanomas and Nevi" Hum. Pathol. 30:562-567, 1999.
Woods et al., "Syndecan-4 Binding to the High Affinity Heparin-Binding Domain of Fibronectin Drives Focal Adhesion Formation in Fibroblasts", Arch. Biochem. Biophys. 374: 66-72, 2000.
Helige et al., "Interelation of Motility, Cytoskeltal Organization and Gap Junctional Communication with Invasiveness of Melanocytic Cells in Vitro" Invasion Metastasis, 17: 26-41, 1997.
Maung et al., "Requirement for Focal Adhesiion Kinase in Tumor Cell Adhesion" Oncogene 18: 6824-6828, 1999.
Silletti et al., "Autocrine Motility Factor and the Extracellular Matrix I. Coordinate Regulation of Melanome Cell Adhesion, Spreading and Migration Involves Focal Contact Reorganization" Int. J. Cancer, 76: 120-128, 1998.
Duggan et al., "Expression Profililng Using cDNA Microarrays" Nature Genet. 21: 10-14, 1999.

(Continued)

Primary Examiner—Misook Yu
Assistant Examiner—Mark Halvorson

(57) ABSTRACT

The overexpression of certain marker genes including Wnt5a has been found useful in the identification of more aggressive forms of malignant melanoma. Therefore, the overexpression of these genes in tumor samples of malignant melanoma may be useful in the diagnosis, profiling, and treatment of patients suffering from this disease. Inhibitors of Wnt5a activity may be useful in the treatment of aggressive forms of malignant melanoma. Inhibition of Wnt5a activity may be effected by any method including anti-sense therapy, gene therapy, and pharmaceutical intervention.

8 Claims, 13 Drawing Sheets
(7 of 13 Drawing Sheet(s) Filed in Color)

OTHER PUBLICATIONS

Khan et al., "DNA Microarray Technology: The Anticipated Impact on the Study of Human Disease" Biochim. Biophys. Acta 1423:: 17-28, 1999.

Tamura et al., "Inhibition of Cell Migration, Spreading and Focal Adhesions by Tumor Suppressor PTEN" Science, 280:1614-1617, 1998.

Berenes et al., "The Role of Extracellular Matrix in Human Astrocytoma Migration and Proliferation Studied Studiied in a Microliter Scale Assay" Clin Exp. Metastasis 12:405-415,1994.

Giese et al., Contrasting Migratory Response of Astocytoma Cells to Tenascin Mediated by Different Integrin, J. Cell Sci., 109: 2161-2168, 1996.

Hendrix et al., "A Simple Quantiative Assay for Studing the Invasive Potential of High and Low Human Metastatic Variants" Cancer Lett. 38: 137-147, 1987.

Hendrix et al., "Role of Intermediate Filaments in Migration, Invasion and Metastasis", Cancer Metastasis Rev. 15:507-525, 1996.

Bui, et al., "Exp;ression and Hormone Regulation of Wnt2, 3, 4, 5a, 7a, 7b and 10b in Normal Human Endometrium and Endometrial Carcinoma", British Journal of Cancer, 75(8): 1131-1136, 1997.

Bui, et al., "Expression of Wnt5a is Downregulated by Extracellular Matrix and Mutated c-Ha-ras in the Human Mammary Epithelial Cell Line MCF-10A", Biochemical and Biophysical Research Communications, 239: 911-917, 1997.

Lejeune, et al., "Wnt5a Cloning, Expression, and Up-Regulation in Human Primary Breast Cancers", Clinical Cancer Research, 1, 215-222, 1995.

Huguet, et al., "Regulation of Wnt5a mRNA Expression in Human Mammary Epithelial Cells by Cell Shape, Confluence, and Hepatocyte Growth Factor", The Journal of Biological Chemistry, 270(21): 12851-12856, 1995.

Jonsson, et al., "Regulation of Wnt5a Expression in Human Mammary Cells by Protein Kinase C Activity and the Cytoskeleton", British Journal of Cancer, 78(4): 430-438, 1998.

* cited by examiner

REAL-TIME PCR OF WNT5A EXPRESSION

WNT5A PROTEIN EXPRESSION

WNT5A antibody staining of transfected cell lines.
A. Antibody negative control
B. Parental cell line (untransfected)
C. Transfectant 1-3
D. Transfectant 4-3
E. Transfectant 4-7
R&D systems anti WNT5a (goat IgG) developed with Cy5 rabbit anti-goat.

WNT5A TRANSFECTANTS-CHANGES IN CELL MORPHOLOGY

ACTIN STAINING OF WNT5A TRANSFECTANTS

BETA-CATENIN STAINING OF WNT5A TRANSFECTANTS

REPRESENTATIVE ACTIVITY OF PKC ISOFORMS

SUMMATION OF CHANGES IN PKC ISOFORM
ACTIVITY UPON WNT5A TRANSFECTION

SCRATCH ASSAY OF WNT5A EFFECTS ON INVASION

BOYDEN CHAMBER ASSAY OF WNT5A EFFECTS ON INVASION

FRIZZLED RECEPTOR EXPRESSION IN MELANOMA CELLS

EFFECT OF FRIZZLED ANTIBODY ON PKC ACTIVITY

EFFECT OF FRIZZLED ANTIBODY ON
INVASION OF WNT5A TRANSFECTANTS

CLASSIFYING CANCERS

REFERENCE TO MATERIAL PRESENTED IN APPENDIX

This patent application includes material comprising tables and data presented as Appendix A on CD-ROM. The one file on the accompanying CD-ROM is entitled AppendixA.xls (2,868 kb), which is a Microsoft Excel Worksheet. The CD-ROM was created on Aug. 2, 2001. The format is IBM-PC. The operating system is MS-Windows 98. The file on the CD-ROM is incorporated herein by reference.

BACKGROUND OF THE INVENTION

Cancer is the second leading cause of death in the United States after cardiovascular disease (Boring et al. *Cancer J. Clin.* 43:7, 1993; incorporated herein by reference). One in three Americans will develop cancer in his or her lifetime, and one of every four Americans will die of cancer. In order to better combat this deadly disease, efforts have recently focused on fine tuning the categorization of tumors; by categorizing cancers, physicians hope to better treat an individual's cancer by providing more effective treatments. Researchers and physicians have categorized cancers based on invasion, metastasis, gross pathology, microscopic pathology, imunohistochemical markers, and molecular markers. With the recent advances in gene chip technology, researchers are increasingly focusing on the categorization of tumors based on the expression of marker genes.

The most common human cancers are malignant neoplasms of the skin (Hall et al. *J. Am. Acad. Dermatol.* 40:35–42, 1999; Weyers et al. *Cancer* 86:288–299, 1999; each of which is incorporated herein by reference). The incidence of cutaneous melanoma is rising especially steeply, with minimal progress in non-surgical treatment of advanced disease (Byers et al. *Hematol. Oncol. Clin. North Am.* 12:717–735, 1998; McMasters et al *Ann. Surg. Oncol.* 6:467–475, 1999; each of which is incorporated herein by reference). Despite significant effort to identify independent predictors of melanoma outcome, no accepted histopathological, molecular, or immunohistochemical marker defines subsets of this neoplasm (Weyers et al. *Cancer* 86:288–299, 1999; Byers et al. *Hematol. Oncol. Clin. North Am.* 12:717–735, 1998; each of which is incorporated herein by reference). Accordingly, though melanoma is thought to present with different "taxonomic" forms, these are considered part of a continuous spectrum rather than discrete entities (Weyers et al *Cancer* 86:288–299, 1999; incorporated herein by reference). Improved characterization and understanding of this potentially deadly disease would be valuable.

SUMMARY OF THE INVENTION

The present invention provides a system for diagnosing aggressive forms of malignant melanoma based on the expression of certain marker genes within a tumor sample. In one embodiment, expression levels are determined for one or more of the following genes: Wnt5a (Seq. ID No.: 1, 2, & 3), MART-1 (Seq. ID No.: 4 & 5), pirin (Seq. ID No.: 6 & 7), HADHB (Seq. ID No.: 8 & 9), CD63 (Seq. ID No.: 10 & 11), EDNRB (Seq. ID No.: 12 & 13), PGAM1 (Seq. ID No.: 14 & 15), HXB (Seq. ID No.: 16 & 17), RXRA (Seq. ID No.: 18 & 19), integrin 1b (Seq. ID No.: 20 & 21), syndecan 4 (Seq. ID No.: 22 & 23), tropomyosin 1 (Seq. ID No.: 24 & 25), AXL (Seq. ID No.: 26 & 27), EphA2 (Seq. ID No.: 28 & 29), GAP43 (Seq. ID. No.: 30 & 31), PFKL (Seq. ID No.: 32 & 33), synuclein a (Seq. ID No.: 34 & 35), annexin A2 (Seq. ID No.: 36 & 37), CD20 (Seq. ID No.: 38 & 39), and RAB2 (Seq. ID No.: 40 & 41). In certain preferred embodiments, expression of a plurality of these genes is detected. In particularly preferred embodiments, Wnt5a is one of the genes whose expression is detected. According to the present invention, overexpression of Wnt5a in a tumor sample indicates a more aggressive form of the disease.

The present invention also provides a system for selecting a treatment protocol for a patient diagnosed with malignant melanoma based on the expression pattern of certain marker genes in a tumor sample. For example, tumors overexpressing Wnt5a may be treated more aggressively or with specific agents such as inhibitors of Wnt5a expression. Inhibitors of Wnt5a activity include anti-sense agents, RNA inhibition agents, small molecule inhibitors of Wnt5a activity, gene therapy, etc.

In another aspect, the present invention provides a system for identifying and then treating aggressive forms of malignant melanoma by administering inhibitors of Wnt5a activity to a subject.

In another aspect, the present invention provides a system for identifying compounds useful in the treatment of cancer, particularly aggressive forms of malignant melanoma expressing Wnt5a. In the inventive method, a cell expressing Wnt5a is contacted with an agent being screened for activities useful in the treatment of cancer, such as decreasing or inhibiting Wnt5a expression and/or activity. The agent may be a polynucleotide, protein, peptide, natural product, small molecule, etc. The level of Wnt5a expression or activity may be assayed using any available technique, including but not limited to, Northern blot analysis, enzyme activity, expression of a reporter gene, etc.

The present invention also provides kits useful in diagnosing or identifying cancers or more aggressive forms of cancer. The kits may be used to identify more aggressive forms of malignant melanoma. The kit may include a gene chip with nucleic acid sequences of genes of interest including Wnt5a, MART-1, pirin, HADHB, CD63, EDNRB, PGAM1, HXB, RXRA, integrin 1b, syndecan 4, tropomyosin 1, AXL, EphA2, GAP43, PFKL, synuclein a, annexin A2, CD20, and RAB2, or a subset thereof. The kit may also or alternatively include primers, enzymes, and reagents for identifying, amplifying, labeling, or sequencing nucleic acids. Same kits may also include reagents for purifying nucleic acids such as mRNA. Rather than detecting gene expression, the kit may be used to determine protein levels and therefore include antibodies directed against the proteins encoded by the genes, Wnt5a, MART-1, pirin, HADHB, CD63, EDNRB, PGAM1, HXB, RXRA, integrin 1b, syndecan 4, tropomyosin 1, AXL, EphA2, GAP43, PFKL, synuclein a, annexin A2, CD20, and RAB2, or a subset thereof.

DEFINITIONS

"Animal": The term animal, as used herein, refers to humans as well as non-human animals, including, for example, mammals, birds, reptiles, amphibians, and fish. Preferred non-human animals are a mammals (e.g., a rodent, a mouse, a rat, a rabbit, a monkey, a dog, a cat, a primate, or a pig). An animal may be a transgenic animal. In certain embodiments, non-human animals may be laboratory animals, raised by humans in a controlled environment other than their natural habitat.

"Antibody": The term antibody refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. The antibody may be a fragment of an antibody such as an Fab fragment or a recombinantly produced scFv fragment.

"Cancer": Cancer refers to a malignant tumor (e.g., lung cancer) or growth of cells (e.g., leukemia). Cancers tend to be less differentiated than benign tumors, grow more rapidly, show infiltration, invasion and destruction, and may metastasize. Cancers include, but are not limited to, fibrosarcoma, myxosarcoma, angiosarcoma, leukemia, squamous cell carcinoma, basal cell carcinoma, malignant melanoma, renal cell carcinoma, hepatocellular carcinoma, etc.

"Effective amount": In general, the "effective amount" of an active agent refers to the amount necessary to elicit a desired biological response. As will be appreciated by those of ordinary skill in this art, the absolute amount of a Wnt5a inhibitor that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, in the case of anti-neoplastic agents, the effective amount may be the amount of agent needed to reduce the size of the primary tumor, to reduce the size of a secondary tumor, to reduce the number of metastases, to reduce the growth rate of a tumor, to reduce the ability of the primary tumor to metastasize, to increase life expectancy, etc.

"Marker gene": A "marker gene" may be any gene or gene product (e.g., protein, peptide, mRNA) that indicates a particular diseased or physiological state (e.g., carcinoma, normal, dysplasia) or indicates a particular cell type, tissue type, or origin. The expression or lack of expression of a marker gene may indicate a particular physiological or diseased state of a patient, organ, tissue, or cell. Preferably, the expression or lack of expression may be determined using standard techniques such as RT-PCR, sequencing, immunochemistry, gene chip analysis, etc. In certain embodiments, the level of expression of a marker gene is quantifiable.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

"Tumor": As used in the present application, "tumor" refers to an abnormal growth of cells. The growth of the cells of a tumor typically exceed the growth of normal tissue and tends to be uncoordinated. The tumor may be benign (e.g., lipoma, fibroma, myxoma, lymphangioma, meningioma, nevus, adenoma, leiomyoma, mature teratoma, etc.) or malignant (e.g., malignant melanoma, ovarian cancer, carcinoma in situ, carcinoma, adenocarcinoma, liposarcoma, mesothelioma, squamous cell carcinoma, basal cell carcinoma, colon cancer, lung cancer, etc.).

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF CERTAIN PREFERRED EMBODIMENTS OF THE INVENTION

Figure 1A:
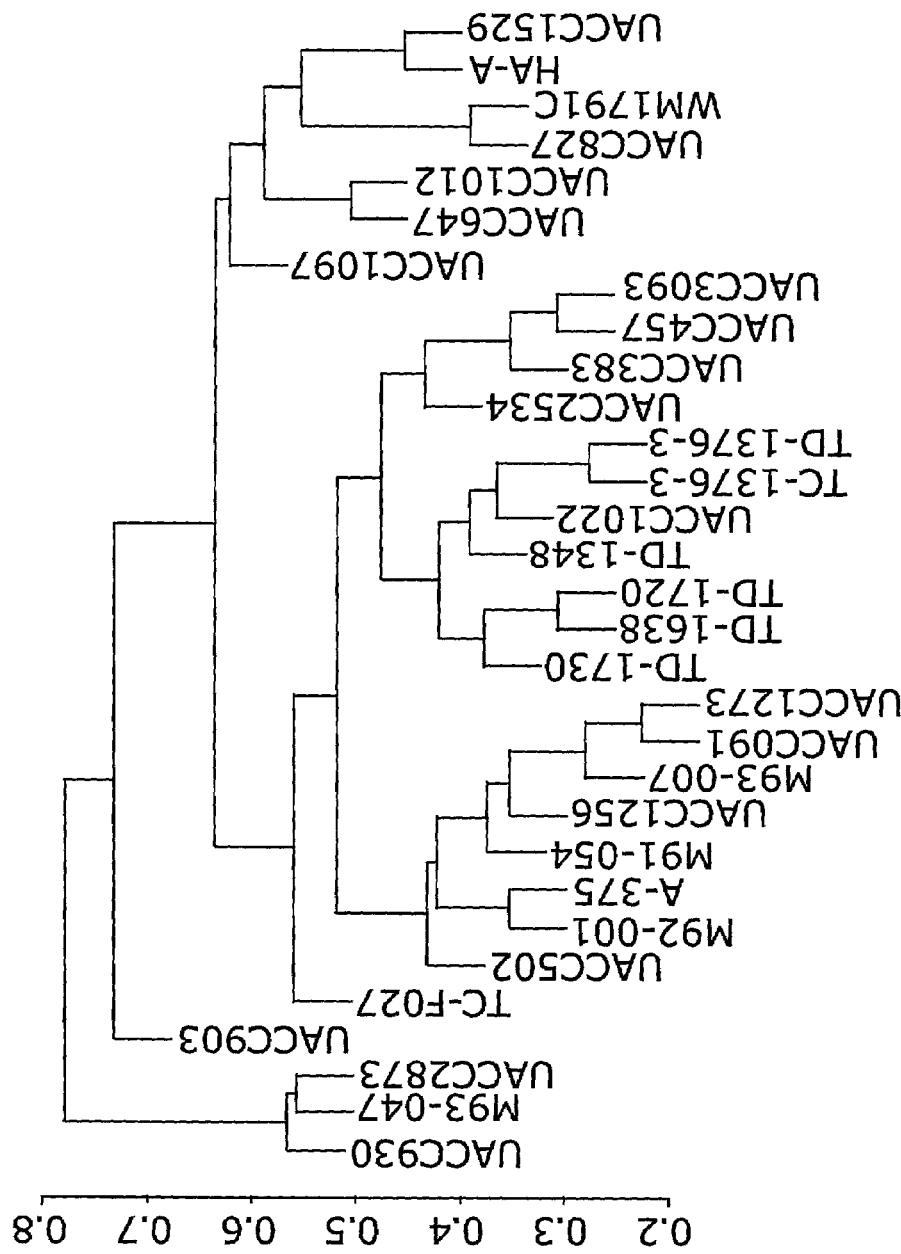
FIG. 1 shows the clustering of gene expression data. a. Hierarchical clustering dendrogram with the cluster of 19 melanomas at the center. b. MDS three-dimensional plot of all 31 cutaneous melanoma samples showing major clustering of 19 samples (blue, within cylinder), and remaining 12 samples (gold). c. A plot of the observed and expected number of genes producing a given number of classification errors for a partition of the 31 melanomas into two groups of 12 and 19. Red triangles, observed clusters; filled bars, randomly produced clusters, open circles, predicted results for randomly variable gene expression. d. Introduction of random gaussian noise followed by cuts from the top of the original tree (resulting in k clusters), to determine discrepant pairs after perturbation (see Supplementary Information in Examples).

The present invention provides systems for identifying and treating cancers based on the expression of marker genes in the cancer cells. In a particular embodiment, the cancer to be categorized is malignant melanoma. The invention allows for the identification of more aggressive forms of cancer and profiling the affected patient so that a proper treatment regimen can be initiated. The present invention also provides for kits useful in practicing the inventive methods.

Diagnosing and Identifying Forms of Cancer

In diagnosing or identifying a particular cancer or tumor, a test sample containing at least one cell from the tumor is provided to obtain a genetic sample. The test sample may be obtained using any technique known in the art including biopsy, blood sample, sample of bodily fluid (e.g., urine, lymph, ascites, cerebral spinal fluid, pleural effusion, sputum, stool, tears, sweat, pus, etc.), surgical excisions needle biopsy, scraping, etc. From the test sample is obtained a genetic sample. The genetic sample comprises a nucleic acid, preferably RNA and/or DNA. For example, in determining the expression of marker genes one can obtain mRNA from the test sample, and the mRNA may be reverse transcribed into cDNA for further analysis. In another embodiment, the mRNA itself is used in determining the expression of marker genes. In some embodiments, the expressions level of a particular marker gene may be determined by determining the level/presence of a gene product (e.g., protein) thereby eliminating the need to obtain a genetic sample from the test sample.

The test sample is preferably a sample representative of the tumor or cancer as a whole. Preferably there is enough of the test sample to obtain a large enough genetic sample to accurately and reliably determine the expression levels of marker genes of interest in the cancer or tumor. In certain embodiments, multiple samples may be taken from the same tumor in order to obtain a representative sampling of the tumor.

A genetic sample may be obtained from the test sample using any techniques known in the art (Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); *Nucleic Acid Hybridization* (B. D. Hames & S. J. Higgins eds. 1984); the treatise, *Methods in Enzymology* (Academic Press, Inc., N.Y.); each of which is incorporated herein by reference). The nucleic acid may be purified from whole cells using DNA or RNA purification techniques. The genetic sample may also be amplified using PCR or in vivo techniques requiring subcloning. In a preferred embodiment, the genetic sample is obtained by isolating mRNA from the cells of the test sample and reverse transcribing the RNA into DNA in order to create cDNA (Khan et al. *Biochem. Biophys. Acta* 1423:17–28, 1999; incorporated herein by reference).

Once a genetic sample has been obtained, it can be analyzed for the presence or absence of particular marker genes. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, etc. In determining the expression level of a marker gene or genes in a genetic sample, the level of expression may be normalized by comparison to the expression of another gene such as a well known, well characterized gene or a housekeeping gene.

The expression data from a particular marker gene or group of marker genes may be analyzed using statistical methods described below in the Examples in order to determine the phenotype or characteristic of a particular tumor or cancer. Methods used in classifying tumors based on gene expression data are described in Ben-Dor et al. *J. Comput. Biol.* 7(3 & 4):559–584, 2000; incorporated herein by reference. The analyzed data may also be used to select/profile patients for a particular treatment protocol.

For example, the present invention demonstrates that marker gene Wnt5a is expressed at high levels in more aggressive forms of malignant melanomas. A patient with malignant melanoma may have the expression level of Wnt5a in the cells of his/her tumor determined in order to help determine the prognosis and/or treatment plan for his/her particular disease. The expression level of Wnt5a would preferably be one of several factors used in deciding the prognosis or treatment plan of a patient. Preferably a trained and fully licensed physician would be consulted in determining the patient's prognosis and treatment plan. A high level of expression of Wnt5a may indicate a worse prognosis and suggest a more aggressive treatment plan. The treatment plan may also include inhibitors of Wnt5a activity such as anti-sense agents and gene therapy directed against Wnt5a. Small molecule inhibitors of Wnt5a activity may also be used in the treatment plan as well as pharmaceuticals that inhibit the Wnt5a pathway either upstream or downstream of Wnt5a itself.

Marker Genes

The present invention provides several marker genes that correlate with particularly aggressive forms of malignant melanoma. These markers may also be useful in categorizing other tumors or cancers other than malignant melanoma. For example, inventive marker genes may be useful in categorizing other types of skin cancer. Preferred marker genes include Wnt5a, MART-1, pirin, HADHB, CD63, ENDRB, PGAM1, HXB, RXRA, integrin b1, syndecan 4, tropomyosin 1, AXL, EphA2, GAP43, PFKL, synuclein a, annexin A2, CD20, and RAB2, and combinations thereof. Other potential marker genes are listed in the Examples below. Particular sets of marker genes may be defined using statistical methods as described in the Examples in order to decrease or increase the specificity or sensitivity of the set. For example, a particular set of marker genes highly specific of aggressive forms of malignant melanoma may be less sensitive (i.e., a negative result may occur in the presence on an aggressive form of melanoma).

Different subsets of marker genes may be developed that show optimal function with different races, ethnic groups, sexes, geographic groups, stages of disease, types of cancer, cell types, etc. Subsets of marker genes may also be developed to be sensitive to the effect of a particular therapeutic regimen on disease progression.

One particularly useful marker gene in the diagnosis of aggressive form of malignant melanoma is Wnt5a. The Wnt genes make up a large family of highly conserved genes that have been studied extensively in development. The first member, int-1 was discovered as a common integration site of mouse mammary tumor virus (MMTV) in mammary epithelial adenocarcinomas (Nusse and Varmus *Cell* 69:1073–1087, 1992; incorporated herein by reference). Int-1 is highly homologous to the *Drosophila* developmental gene wingless that is involved in pattern formation. The combination of wingless and int-1 gives rise to the term Wnt. Homologues of Wnt genes have been isolated in *Drosophila, Xenopus*, chicken, mouse, and humans (Nusse and Varmus *Cell* 69:1073–1087, 1992; incorporated herein by reference). In humans, there are nine Wnt genes known including Wnt5a (Clark et al. *Genomics* 18:249–260, 1993; Lejeune et al. *Clin. Cancer Res.* 1:215–222, 1995; each of which is incorporated herein by reference). Wnt5a has been found to be up-regulated in lung, colon, and prostate carcinomas and melanomas (Iozzo et al. *Cancer Res.* 55:3495–3499, 1995; incorporated herein by reference).

The sequence of the mRNA of *Homo sapiens* wingless MMTV integration site family, member 5a (Wnt5a) is shown below:

```
  1   attaattctg gctccacttg ttgctcggcc caggttgggg agaggacgga gggtggccgc   (Seq. ID No.: 2)

61   agcgggttcc tgagtgaatt acccaggagg gactgagcac agcaccaact agagagggt 121   caggggtgc gggactcgag cgagcaggaa ggaggcagcg cctggcacca gggctttgac 181   tcaacagaat tgagacacgt ttgtaatcgc tggcgtgccc cgcgcacagg atcccagcga 241   aaatcagatt tcctggtgag gttgcgtggg tggattaatt tggaaaaaga aactgcctat 301   atcttgccat caaaaaactc acggaggaga agcgcagtca atcaacagta aacttaagag 361   accccgatg ctcccctggt ttaacttgta tgcttgaaaa ttatctgaga gggaataaac 421   atctttcct tcttccctct ccagaagtcc attggaatat taagcccagg agttgctttg 481   gggatggctg gaagtgcaat gtcttccaag ttcttcctag tggctttggc catattttc 541   tccttcgccc aggttgtaat tgaagccaat tcttggtggt cgctaggtat gaataaccct 601   gttcagatgt cagaagtata tattatagga gcacagcctc tctgcagcca actggcagga
```

-continued

```
 661  ctttctcaag gacagaagaa actgtgccac ttgtatcagg accacatgca gtacatcgga
 721  gaaggcgcga agacaggcat caaagaatgc cagtatcaat tccgacatcg acggtggaac
 781  tgcagcactg tggataacac ctctgttttt ggcagggtga tgcagatagg cagccgcgag
 841  acggccttca catacgccgt gagcgcagca ggggtggtga acgccatgag ccgggcgtgc
 901  cgcgagggcg agctgtccac ctgcggctgc agccgcgccg cgcgccccaa ggacctgccg
 961  cgggactggc tctgggcgg ctgcggcgac aacatcgact atggctaccg ctttgccaag
1021  gagttcgtgg acgcccgcga gcgggagcgc atccacgcca agggctccta cgagagtgct
1081  cgcatcctca tgaacctgca caacaacgag gccggccgca ggacggtgta caacctggct
1141  gatgtggcct gcaagtgcca tggggtgtcc ggctcatgta gcctgaagac atgctggctg
1201  cagctggcag acttccgcaa ggtgggtgat gccctgaagg agaagtacga cagcgcggcg
1261  gccatgcggc tcaacagccg gggcaagttg gtacaggtca acagccgctt caactcgccc
1321  accacacaag acctggtcta catcgacccc agccctgact actgcgtgcg caatgagagc
1381  accggctcgc tgggcacgca gggccgcctg tgcaacaaga cgtcggaggg catggatggc
1441  tgcgagctca tgtgctgcgg ccgtgggtac gaccagttca gaccgtgca gacggagcgc
1501  tgccactgca agttccactg gtgctgctac gtcaagtgca agaagtgcac ggagatcgtg
1561  gaccagtttg tgtgcaagta gtgggtgcca cccagcactc agcccgctc ccaggacccg
1621  cttatttata gaaagtacag tgattctggt ttttggtttt tagaaatatt ttttattttt
1681  ccccaagaat tgcaaccgga accatttttt ttcctgttac catctaagaa ctctgtggtt
1741  tattattaat attataatta ttatttggca ataatggggg tgggaaccac gaaaaatatt
1801  tattttgtgg atctttgaaa aggtaataca agacttcttt tggatagtat agaatgaagg
1861  gggaaataac acataccccta acttagctgt gtgggacatg gtacacatcc agaaggtaaa
1921  gaaatacatt ttcttttttct caaatatgcc atcatatggg atgggtaggt tccagttgaa
1981  agagggtggt agaaatctat tcacaattca gcttctatga ccaaaatgag ttgtaaattc
2041  tctggtgcaa gataaaaggt cttgggaaaa caaaacaaaa caaaacaaac ctcccttccc
2101  cagcagggct gctagcttgc tttctgcatt ttcaaaatga taatttacaa tggaaggaca
2161  agaatgtcat attctcaagg aaaaaaggta tatcacatgt ctcattctcc tcaaatattc
2221  catttgcaga cagaccgtca tattctaata gctcatgaaa tttgggcagc agggaggaaa
2281  gtccccagaa attaaaaaat ttaaaactct tatgtcaaga tgttgatttg aagctgttat
2341  aagaattggg attccagatt tgtaaaaaga cccccaatga ttctggacac tagatttttt
2401  gtttggggag gttggcttga acataaatga aatatcctgt attttcttag ggatacttgg
2461  ttagtaaatt ataatagtag aaataataca tgaatcccat tcacaggttt ctcagcccaa
2521  gcaacaaggt aattgcgtgc cattcagcac tgcaccagag cagacaacct atttgaggaa
2581  aaacagtgaa atccaccttc ctcttcacac tgagccctct ctgattcctc cgtgttgtga
2641  tgtgatgctg gccacgtttc caaacggcag ctccactggg tcccctttgg ttgtaggaca
2701  ggaaatgaaa cattaggagc tctgcttgga aaacagttca ctacttaggg atttttgttt
2761  cctaaaactt ttattttgag gagcagtagt tttctatgtt ttaatgacag aacttggcta
2821  atggaattca cagaggtgtt gcagcgtatc actgttatga tcctgtgttt agattatcca
2881  ctcatgcttc tcctattgta ctgcaggtgt accttaaaac tgttcccagt gtacttgaac
2941  agttgcattt ataaggggg aaatgtggtt taatggtgcc tgatatctca aagtcttttg
3001  tacataacat atatatatat atacatatat ataaatataa atataaatat atctcattgc
```

```
-continued
3061  agccagtgat ttagatttac agcttactct ggggttatct ctctgtctag agcattgttg 3121  tccttcactg cagtccagtt gggattattc caaaagtttt ttgagtcttg agcttgggct 3181  gtggcccgc  tgtgatcata ccctgagcac gacgaagcaa cctcgtttct gaggaagaag 3241  cttgagttct gactcactga aatgcgtgtt gggttgaaga tatctttttt tcttttctgc 3301  ctcacccctt tgtctccaac ctccatttct gttcactttg tggagagggc attacttgtt 3361  cgttatagac atggacgtta agagatattc aaaactcaga agcatcagca atgtttctct 3421  tttcttagtt cattctgcag aatggaaacc catgcctatt agaaatgaca gtacttatta 3481  attgagtccc taaggaatat tcagcccact acatagatag ctttttttt ttttttttt 3541  ttttaataag gacacctctt tccaaacagg ccatcaaata tgttcttatc tcagacttac 3601  gttgttttaa aagtttggaa agatacacat cttttcatac cccccttag gaggttgggc 3661  tttcatatca cctcagccaa ctgtggctct taatttattg cataatgata tccacatcag 3721  ccaactgtgg ctctttaatt tattgcataa tgatattcac atcccctcag ttgcagtgaa 3781  ttgtgagcaa aagatcttga aagcaaaaag cactaattag tttaaaatgt cacttttttg 3841  gttttatta  tacaaaaacc atgaagtact tttttttattt gctaaatcag attgttcctt 3901  tttagtgact catgtttatg aagagagttg agtttaacaa tcctagcttt taaaagaaac 3961  tatttaatgt aaaatattct acatgtcatt cagatattat gtatatcttc tagcctttat 4021  tctgtactt  taatgtacat atttctgtct tgcgtgattt gtatatttca ctggtttaaa 4081  aaacaaacat cgaaaggctt attccaaatg gaag
```

The translated sequence of Wnt5a is as follows:

```
MAGSAMSSKFFLVALAIFFSFAQVVIEANSWWSLGMNNPVQMSE                        (Seq. ID No.: 3)

VYIIGAQPLCSQLAGLSQGQKKLCHLYQDHMQYIGEGAKTGIKECQYQFRHRRWNCST

VDNTSVFGRVMQIGSRETAFTYAVSAAGVVNAMSRACREGELSTCGCSRAARPKDLPR

DWLWGGCGDNIDYGYRFAKEFVDARERERIHAKGSYESARILMNLHNNEAGRRTVYNL

ADVACKCHGVSGSCSLKTCWLQLADFRKVGDALKEKYDSAAAMRLNSRGKLVQVNSRF

NSPTTQDLVYIDPSPDYCVRNESTGSLGTQGRLCNKTSEGMDGCELMCCGRGYDQFKT

VQTERCHCKFHWCCYVKCKKCTEIVDQFVCK
```

Other sequences homologous to the above sequences may also be used in the present invention. Preferably the sequence is at least 70% identical to the human Wnt5a DNA and protein sequences listed above. More preferably the sequence is at least 80%, 90%, 95%, 97%, 98%, 99%, or >99% identical. A homolog of Wnt5a may also be identified by its activity. In another preferred embodiment, the homolog of Wnt5a is identified by its location in the genome (e.g., location on the chromosome).

Identifying Anti-Neoplastic Agents

The present invention also provides a novel method of identifying compounds useful in the treatment of patients with cancer. In certain embodiments, the cancer is malignant melanoma. In other embodiments, the cancer is a malignant melanoma expressing Wnt5a. In particular, the inventive method identifies compounds directed against Wnt5a or Wnt5a activity specifically, or more generally, against downstream or upstream signals in the Wnt5a pathway.

Any compound, moiety, or entity can be screened for activity against Wnt5a according to the present invention. For example, polynucleotides, peptides, proteins, natural products, chemical compounds, small molecules, polymers, biomolecules, etc. may be tested. The agents to be screened may be prepared by purification or synthesis, or may be obtained from commercial or other stock sources.

The assay used to screen the agents may be an in vitro or in vivo assay. For example, an in vitro assay may utilize purified or partially purified WNT5A protein. The WNT5A protein may be obtained by purifying the protein from a natural source or from a cell, such as bacteria, mammalian cells, yeast, or fungi, overexpressing WNT5A. Methods for overexpressing and purifying the proteins encoded by cloned genes are well known in the art (see, Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989; each of which is incorporated herein by reference). Agents may be screened for their ability to bind the WNT5A protein or to enhance or prevent an interaction between WNT5A and another protein, peptide, polynucleotide, or chemical compound. Agents may also be screened for their ability to affect more downstream effects of WNT5A. Agents may be screened using high-throughput techniques known in the arts.

In one embodiment of an in vivo assay, a cell expressing Wnt5a is contacted with an agent to be tested. The level of Wnt5a expression or activity is then determined using an assay known in the art. These assays may include but are not limited to Northern blot analysis, enzyme activity, quantitative PCR, Western blot analysis, etc. As would be appreciated by one of skill in this art, experiments designed to screen for agents directed against Wnt5a may include proper positive and/or negative controls. The experiment may also include testing a particular agent a several difference concentrations in the range of about 1 nM to about 100 mM, preferably about 1 nM to about 1 mM, more preferably about 1 nM to about 100 μM.

In one preferred embodiment, the cells used in the screening method are skin cells, more preferably malignant melanoma cells. In certain embodiments, the cells or cell line are genetically engineered to express Wnt5a. In certain embodiments, the cells are malignant melanoma cells that did not express Wnt5a naturally but have been genetically engineered to express Wnt5a. Preferred embodiments of such cells and cell lines are described below in the Examples.

Inventive methods of detecting whether a compound inhibits Wnt5a may include an assay which assesses the ability of the cells to "chew through", digest, or migrate through extracellular matrix as described below in the Examples. Assays of this type may include, but are not limited to, the scratch assay, and the Boyden chamber assay. A cell that overexpresses Wnt5a may be able to digest or migrate through extracellular matrix in its search for media or nutrients. Agents that inhibit such a cell's ability to digest extracellular matrix and/or may be inhibiting the activity of Wnt5a may be useful in the treatment malignant melanoma expressing Wnt5a. In a preferred embodiment, the agent reduces the ability of the cell to digest or migrate through extracellular by at least about 50% when compared to cell that were not contacted with the agent, more preferably by at least about 75%, and most preferably by at least about 90%.

In certain other embodiments, cell morphology or cytoskeletal organization may be used to assess the effect of an agent on cells expressing Wnt5a. The cells may be contacted with various concentrations of the agent with a control plate of cells contacted with no agent. The shape of the cells, number of attachments of each cell to the plate, and/or the organization of actin filaments may be assessed to determine the effect of the agent on the cells. In other embodiments, downstream signaling molecules in the Wnt5a pathway are analyzed to determine the effect of the added agent. In one embodiment, the phosphorylation of protein kinase C is used to determine the effect of the agent.

Figure 5:
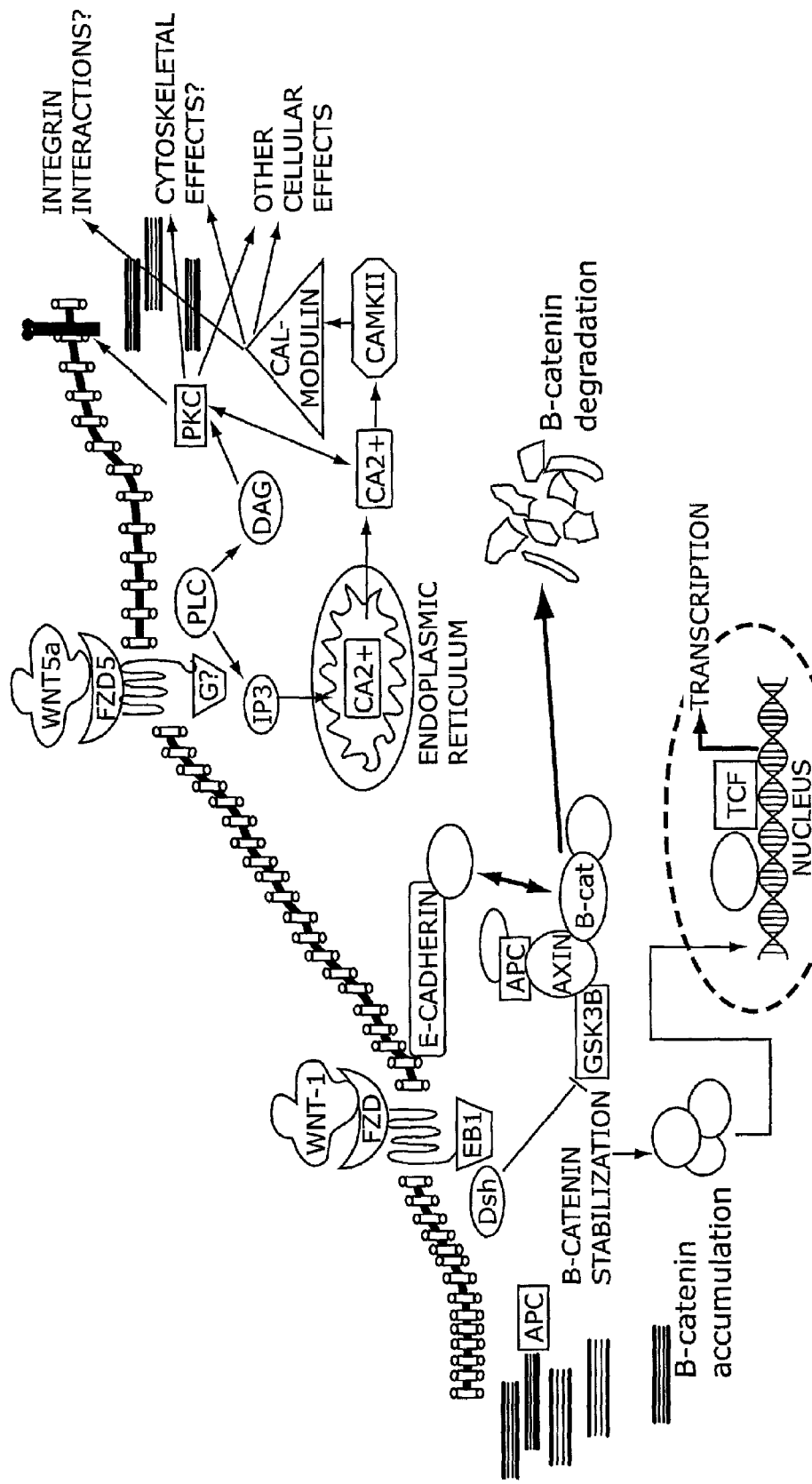
FIG. 5 shows a diagram of the Wnt5a and Wnt1 signaling pathways.

In other embodiments, agents may be screened for their ability to inhibit or knock out the Wnt5a pathway as shown in FIG. 5. In one embodiment, agents may be screened for their ability to block the binding of WNT5A to its receptor, frizzled 5. An agent able to block this binding interaction could possibly attenuate or reverse the phenotypes that increased WNT5A would normally produce, such as increased cell movement an invasiveness.

These and other aspects of the present invention will be further appreciated upon consideration of the following Examples, which are intended to illustrate certain particular embodiments of the invention but are not intended to limit its scope, as defined by the claims.

EXAMPLES

Example 1

Molecular Classification of Cutaneous Malignant Melanoma by Gene Expression Profiling We have proposed that a discrete and previously unrecognizable cancer taxonomy can be identified by viewing the systematized data from gene expression experiments (Bittner et al. *Nature* 406:536–540, 3 Aug. 2000; incorporated herein by reference). However, for melanoma, inherent or technically induced variation could obscure such a classification as its appearance is very similar between patient samples and, in contrast to haematologic cancers (Golub et al. "Molecular classification of cancer, class discovery and class prediction by gene expression monitoring" *Science* 286:531–537, 1999; Alizadeh et al. "Distinct types of diffuse large B-cell lymphoma identified by gene expression profiling" *Nature* 403:503–511, 2000; each of which is incorporated herein by reference), it has few known recurring genetic changes. To explore this question, we gathered expression profiles for 38 samples, including 31 melanomas and 7 controls (Table 1). Total messenger RNA was isolated directly from melanoma biopsies or tumor cell cultures, prepared fluorescent complementary DNA from the message and hybridized them to a microarray containing probes for 8,150 cDNAs (representing 6,971 unique genes), obtaining quantitative and comparative measurements for each gene.

The tumor cell mRNA was compared with a single reference probe, providing normalized measures of the expression of each gene in each sample relative to the standard. Analysis of the normalized expression across all genes between samples provided a measure of the overall difference in expression pattern between samples. Similarly, the orthogonal analysis of linear covariance between pairs of genes across all samples provided a measure of the similarity of behavior of the genes studied.

Figure 1B:
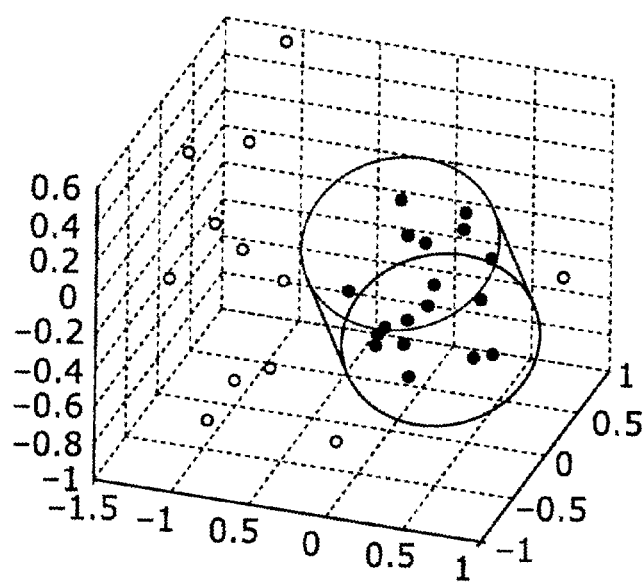

FIG. 1 shows the integration of several analytical methods to visualize the overall expression pattern relationships between cutaneous melanoma tumor samples. Using a matrix of Pearson correlation coefficients from the complete pair-wise comparison of all experiments (Bittner et al. "Data analysis and integration of steps and arrows" *Nature Genet.* 22:213–215, 1999; incorporated herein by reference), the 31 melanoma experiments are displayed as a hierarchical clustering dendrogram (Khan et al. "Gene expression profiling of alveolar rhabdomyosarcoma with cDNA microarrays" *Cancer Res.* 58:5009–5013, 1998; Eisen et al. "Cluster analysis and display of genome-wide expression patterns" *Proc. Natl. Acad. Sci. USA* 95:14863–14868, 1998; each of which is incorporated herein by reference) and as a three-dimensional multidimensional scaling (MDS) plot (Khan et al. "Gene expression profiling of alveolar rhabdomyosarcoma with cDNA microarrays" *Cancer Res.* 58:5009–5013, 1998; Everitt, B. *Applied Multivariant Data Analysis*. (Oxford Univ. Press, New York, 1992); incorporated herein by reference). The MDS plot displays the position of each tumor sample in three-dimensional Euclidean space, with the distance between experimental samples reflecting their approximate degree of correlation (Khan et al. "Gene expression profiling of alveolar rhabdomyosarcoma with cDNA microarrays" *Cancer Res.* 58:5009–5013, 1998;

Everitt, B. *Applied Multivariant Data Analysis.* (Oxford Univ. Press, New York, 1992); incorporated herein by reference). The analysis included all genes meeting a minimum level of expression in each hybridization. We also employed a non-hierarchical clustering algorithm (termed cluster affinity search technique; CAST) (Ben-Dor et al. "Clustering gene expression patterns" *J. Comput. Biol.* 6:281–297, 1999; incorporated herein by reference) to define experimental clusters. The resulting hierarchical dendrogram of the 31 melanoma samples (FIG. 1a) demonstrates that 19 samples are tightly clustered at the bottom of the dendrogram in the area of highest similarity. Likewise, the non-hierarchical CAST algorithm identified the identical major cluster 19 melanomas. This cluster is also a compact, readily separable grouping based on its overall similarity of expression pattern viewed by MDS (FIG. 1b).

Figure 1C:
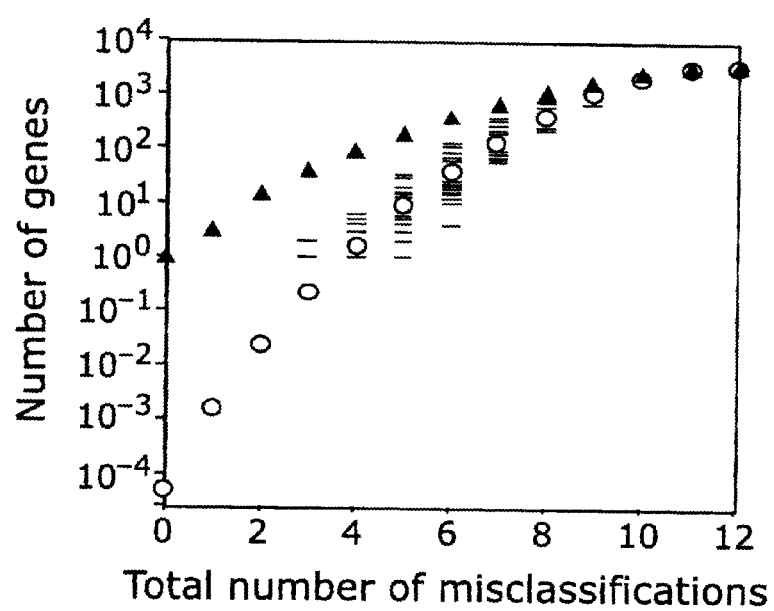

There is no single established method to estimate the significance of an observed degree of relationship obtained by cluster prediction techniques (Golub et al. "Molecular classification of cancer, class discovery and class prediction by gene expression monitoring" *Science* 286:531–537, 1999; Bittner et al. "Data analysis and integration of steps and arrows" *Nature Genet.* 22:213–215, 1999; each of which is incorporated herein by reference). Accordingly, we used two independent approaches to test the validity of our cluster prediction of the 19-element cluster. The first approach (FIG. 1c) examines the power of individual genes to discriminate the major cluster of 19 from the remaining samples by examining the frequency of strong classifier genes compared to the expected frequency of such genes if expression is randomly variable, and to the frequency of strong classifiers in random partitions of the same samples into new groupings of 19 and 12 (Ben-Dor et al. "Class Discovery in Gene Expression Data" *Proceeding RECOMB* 2001, pp. 31–38, 2001; incorporated herein by reference). The non-randomness of the cluster results is evident. Specifically, many genes have expression patterns that differ strongly between the initial sample clusters and thus serve as good classifiers (FIG. 1c, red triangles). However, expression patterns are not readily found which classify the samples when they are grouped into random partitions of the same size (FIG. 1c, blue lines). Accordingly, in randomly formed clusters, expression behavior is essentially indistinguishable from truly random behavior of genes relative to these clusters (FIG. 1c, compare blue lines with open circles).

The second approach we used to test the validity of the cluster predictions is based on evaluating cluster membership after introducing random perturbations to the data set. For each sample, the log-ratio of each gene was perturbed by the introduction of random gaussian noise with the mean equal to 0 and the standard deviation equal to 0.15 (an estimate of variation derived by computing the median standard deviation of the log-ratios for single genes across all 31 samples). Hierarchical clustering was then performed on the perturbed data set and a comparison made between the original tree (FIG. 1a) and the perturbed tree. Comparisons involved cutting the original and perturbed trees into k clusters followed by computing the proportion of paired samples clustering together in the original tree that did not cluster together in the perturbed tree (we refer to this measure as a weighted proportion of discrepant pairs because it gives more weight to larger clusters). The comparison was repeated over multiple perturbed data sets for each possible cut in the original tree (k=2, 3, . . . , 30). For a given k, the weighted proportion of discrepant pairs was then averaged over the perturbed data sets resulting in the identification of weighted average discrepant pairs ($WADP_k$; see Supplementary Information).

Figure 1D:
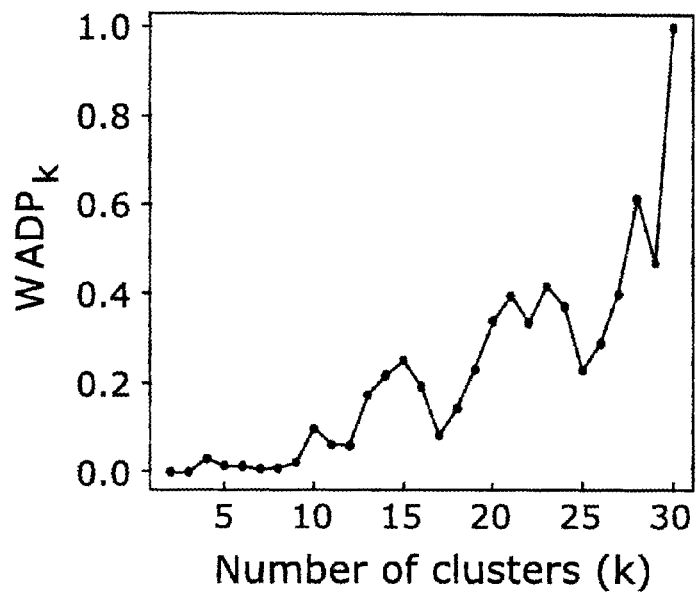

Clusters that result from cutting the original tree into 9 or fewer groups are very reproducible (FIG. 1d). It is noteworthy that the rise in $WADP_k$ almost exactly coincides with the division of the major 19-element cluster into smaller subclusters. These results strongly support the view that the major cluster of melanoma samples identified in this study represents a bona fide and highly reproducible grouping.

We then performed statistical tests to determine whether any clinical or tumour cell characteristics were specifically associated with the clustered group. Tests for associations between the major cluster of 19 samples and the remaining 12 melanoma samples were performed for several in vivo variables, including sex, age, biopsy site, Breslow thickness, Clark's level and survival. There was no statistically significant association between the cluster group and any clinical variable. There were also no significant associations with the in vitro variables, including p16 or β-catenin mutation status, in vitro pigmentation and cell passage number (see Supplementary Information).

We included two pairs of specimens derived from the same patient in this sample set. These are M92-001 and M93-007 (two different samples from the same individual, surgically removed one year apart), and TD-1376-3 and TC-1376-3 (the biopsy sample and a cell culture of the same tumour carried three passages in vitro). Although there was no significant association between cell passage number and cluster group (P=0.857, see Supplementary Information), the TD-1376-3/TC-1376-3 pair were included to serve as another control for the effects of cell culture. Remarkably, of the 465 pairwise comparisons among the melanoma samples, the pairs TD-1376-3/TC-1376-3 and M92-001/M93-007 are the second and third most highly correlated pairs of samples, with nearly identical correlation coefficients (FIG. 1b).

Figure 2A:
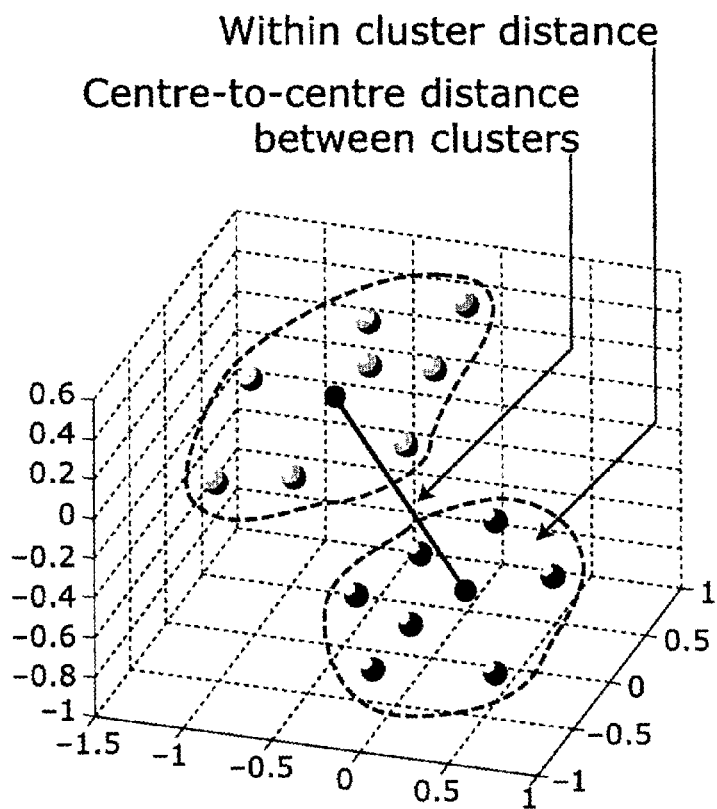
FIG. 2 illustrates the identification of genes which discriminate melanoma clusters. a. MDS analysis ranking genes according to their impact on minimizing cluster volume and maximizing center-to center inter-cluster distance. b. Top 22 genes obtained by these criteria listed in order of decreasing weight (for a full list, see Supplementary Information in Examples). Right, data from cutaneous melanomas identified on the horizontal axis and sorted by cluster (described in Maniotis et al. "Vascular channel formation by human melanoma cells in vivo and in vitro: vasculogenic mimicry" *Am. J. Pathol.* 155:739–752, 1999; incorporated herein by reference). Left, data from uveal melanomas expressed as the ratio of highly invasive to less invasive. Red, high ratios; green, low ratios (intensity of saturation scaled according to the ratio). The three genes not scored in the uveal samples were not included in the print design of the cutaneous samples.
Figure 2B:
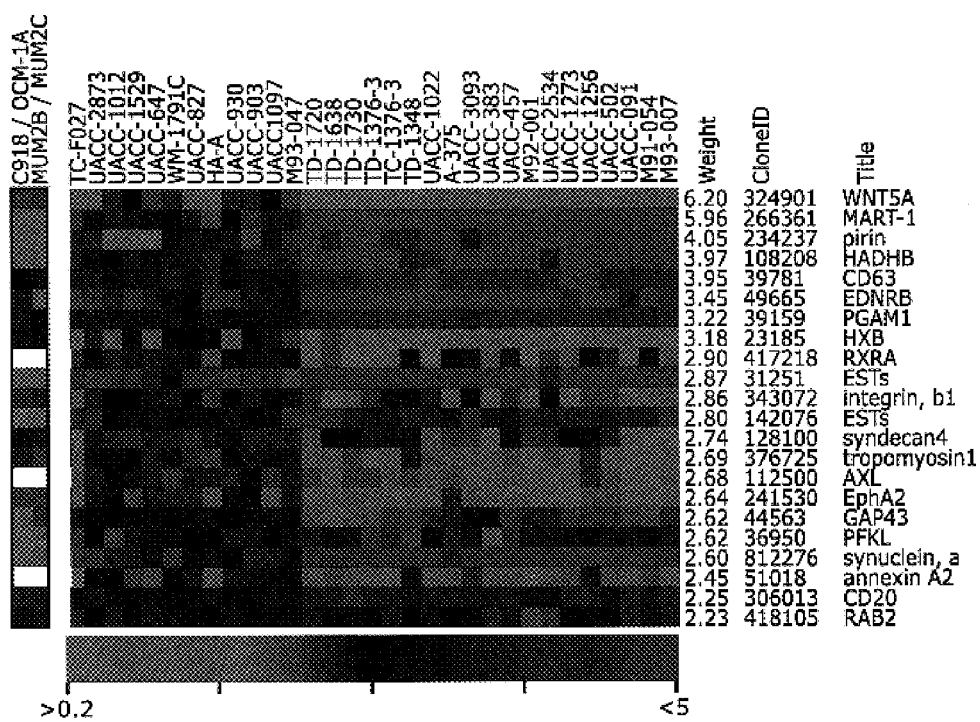
Figure 3:
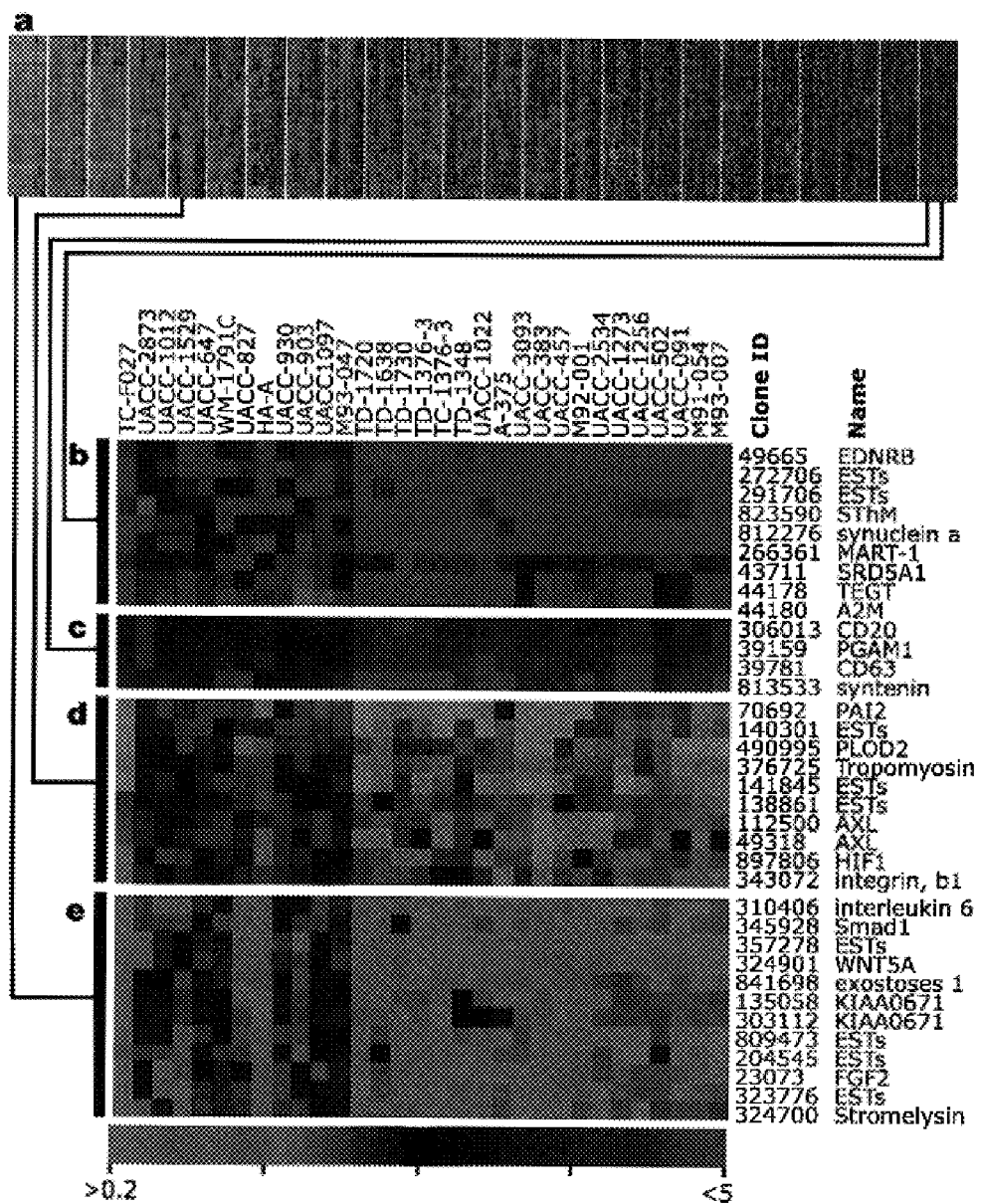
FIG. 3. Guiding gene cluster selection. a. Two-dimensional cluster analysis of cutaneous melanoma samples (horizontal axis) and genes (vertical axis, presented in segments). b–e. Data from a queried at regions corresponding to four two discriminators of the major cluster: MART-1 (b), CD63 (c), tropomyosin (d), and WNT5a (e). Note that these clusters include other genes from the discriminator list (bold). The major cluster of 19 samples is visually apparent on the left of this display. The full list of gene names and corresponding calculated ratio information is provided in the Supplementary Information in the Examples.

On the basis of the linear correlation of global gene expression in FIG. 1, FIGS. 2 and 3 illustrate the approach we have used to guide 'gene cluster' interpretation empirically. FIG. 2a depicts our statistical method for extracting a 'weighted list' of individual genes whose variance of change across all experiments correctly defines the boundary of a given sample cluster (for details see Supplementary Information). FIG. 2b displays the list of genes with the most power to define the major melanoma cluster of 19 samples (FIGS. 1a and b) in rank order along the vertical axis. The samples are ordered along the horizontal axis by cluster inclusion, and data are presented graphically as coloured images with the colour saturation directly proportional to the magnitude of the measured gene expression ratio (brightest red, highest R/G ratio; black squares, R/G ratio=1; brightest greens, lowest R/G ratio). The complete list of genes discriminating the major cluster is in the Supplementary Information.

The weighted gene list can also be used to guide analysis of the larger gene expression data set. FIG. 3a displays all data from the cutaneous melanoma samples in this study as a coloured image with genes ordered along the vertical axis by similarity of expression pattern (after Eisen et al. "Cluster analysis and display of genome-wide expression patterns" *Proc. Natl. Acad. Sci. USA* 95:14863–14868, 1998; incorporated herein by reference). However, rather than basing analysis of this large (>300,000 elements) data set entirely on visual selection, we used genes from the weighted list to index gene cluster selection. FIG. 3b–e illustrates this approach using four genes from the 'weighted list' in FIG. 2b (MART-1, CD63, tropomyosin and WNT5A), to interrogate the entire gene expression data set represented in FIG. 3a.

TABLE 1

Summary of melanoma cases by cluster designation

| Case no. | Sex/Age | Biopsy site | Passage no (Biopsy) | p16 mutation status* | Invasive ability† | Vasulogenic mimicry‡ | Gel contraction§ | Cell motilit‖ | Scratch wound (%)¶ |
|---|---|---|---|---|---|---|---|---|---|
| Melanoma primary cluster | | | | | | | | | |
| UACC-502 | M/69 | Cervical node | 3 | Deleted | 2.8 ± 01% | − | ND | ND | 37 |
| M92-001 | F/43 | Ankle | 2 | Deleted | 3.0 ± 0.5% | − | ND | 76.8 ± 2.96 | 22 |
| A-375 | F/54 | Skin | ND | Mutation | 2.8 ± 0.2% | − | ND | 67.80 ± 4.40 | 26 |
| M91-054# | M/45 | Axill. lymph node | 3 | WT | # | # | # | ND | 30 |
| UACC-1256 | F/67 | Thigh femoral node | 9 | Deleted | ND | ND | ND | ND | ND |
| M93-007 | F/43 | Ankle | 3 | Deleted | 2.6 ± 0.1% | − | − | ND | 12 |
| UACC-091 | M/52 | Unk | 7 | Deleted | 2.1 ± 0.2% | − | − | ND | 11 |
| UACC-1273 | M/50 | Axill. lymph node | 16 | Mutation | 2.5 ± 0.3% | − | − | ND | 13 |
| TD-1730 | M/55 | Thyroid lobe | Biopsy | ND | ND | ND | ND | ND | ND |
| TD-1638 | M/49 | Paraspinous | Biopsy | ND | ND | ND | ND | ND | ND |
| TD-1720 | M/29 | Shoulder | Biopsy | ND | ND | ND | ND | ND | ND |
| TD-1348 | M/44 | Axill. lymph node | Biopsy | ND | ND | ND | ND | ND | ND |
| UACC-1022 | F/53 | Chest wall | 13 | WT | 2.9 ± 0.1% | − | − | ND | 63 |
| TC-1376¤ | M/30 | Distal ileum | 3 | ND | ND | ND | ND | ND | 21 |
| TD-1376¤ | M/30 | Distal ileum | Biopsy | ND | ND | ND | ND | ND | ND |
| UACC-2534 | M/68 | Abdomen | 7 | Deleted | 3.2 ± 0.02% | − | ND | ND | 7 |
| UACC-383 | M/69 | Thigh femoral node | 29 | Deleted | 2.3 ± 0.2% | − | ND | 70.40 ± 5.27 | 35 |
| UACC-457 | FUkn | Unk | 19 | WT | 3.1 ± 0.2% | − | ND | 12.80 ± 0.05 | ND |
| UACC-3093 | M/75 | Axill. lymph node | 4 | WT | ND | ND | ND | 40.30 ± 2.00 | 24 |
| Melanoma non-clustered | | | | | | | | | |
| UACC-930 | F/35 | Sm. bowel | 4 | WT | 4.8 ± 0.3% | ± | − | ND | 50 |
| M93-047 | F/75 | Axill. lymph node | 3 | Mutation | 10.7 ± 0.03% | + | + | ND | 75 |
| UACC-2973 | M/37 | Axill. lymph node | 5 | ND | ND | ND | ND | ND | 48 |
| UACC-903 | M/25 | Back | 14 | Deleted | 3.8 ± 0.3% | + | − | ND | 91 |
| TC-F027 | M/30 | Rt. chest wall | 6 | ND | ND | ND | ND | ND | 91 |
| UACC-1097 | M/56 | Rectus muscle | 6 | Mutation | ND | ND | ND | ND | 34 |
| UACC-647** | M/32 | Axill. node | 14 | WT | 3.8 ± 0.1% | + | ± | ND | 55 |
| UACC-1012 | M/54 | Neck | 3 | ND | 4.9 ± 0.1% | ND | ND | 122.00 ± 11.30 | 54 |
| UACC-827 | F/32 | Rt. breast | 16 | Mutation | ND | ND | ND | ND | 32 |
| WM1791C | Unk | Ukn | 52 | ND | 4.6 ± 0.3% | + | ND | 141.00 ± 11.40 | 71 |
| HA-A | F/Ukn | Ukn | 19 | ND | 3.9 ± 0.5% | ± | ND | 211.00 ± 12.40 | 62 |
| UACC-1529 | M/48 | Axill. lymph node | 13 | Mutation | 4.2 ± 0.5% | + | − | ND | ND |
| Uveal melanoma samples | | | | | | | | | |
| CCM-1A | Unk | Primary | 25 | ND | 2.2 ± 01% | − | − | ND | ND |
| C918 | F/60 | Primary | 15 | ND | 12.9 ± 03% | + | + | ND | ND |
| MUM-2C | M | Liver metastases | 8 | ND | 2.0 ± 0.1% | − | − | ND | ND |
| MUM-2B | M | Liver metastases | 8 | ND | 13.3 ± 0.6% | + | + | ND | ND |
| Control samples | | | | | | | | | |

Nil. C (fibroblast), UACC-3149 (ovarian adenocarcinoma); MCF-10A (breast epithelium), CRL-1634 (fibroblast), SRS-3 (cell culture variant), SRS-5 (cell culture variant), RMS-13 (rhabdomyosarcoma)

*Mutation status of indicated samples for p16 obtained by sequencing Deleted, homozygous. Supplementary Information includes the specific mutations in p16 for each sample tested. Samples were also sequenced for β-catenin. No example of β-catenin mutation was observed.
†Ability to invade a defined basement matrix. P = 0.0055; t-test for two populations.
‡Tube forming ability at 5 days in a three-dimensional matrigel matrix
§Ability to contract floating collagen 1 gels at 5 days as compared to HT-1080 fibrosarcoma cells (Maniotis et al. "Vascular channel formation by human melanoma cells in vivo and in vitro: vasculogenic mimicry" Am. J Pathol 155 739–752, 1999, incorporated herein by reference)
‖Migration rates expressed in μm per day. Mean from eight experiments ± s d (P = 0.0063; t-test for two populations) Rates below 100 μm per day completely segregates in the melanoma primary cluster TABLE 1-continued Summary of melanoma cases by cluster designation

| Case no. | Sex/Age | Biopsy site | Passage no (Biopsy) | p16 mutation status* | Invasive ability† | Vasulogenic mimicry‡ | Gel contraction§ | Cell motilit!! | Scratch wound (%)¶ |
|---|---|---|---|---|---|---|---|---|---|

¶Ability to close in vitro scratch wound at 24 h. Photographs of the wound were measured and percentage wound closure determined (Silletti et al. "Autocrine motility factor and the extracellular matrix I Coordinate regulation of melanome cell adhesion, spreading and migration involves focal contact reorganization" Int J. Cancer 76:120–128, 1998; incorporated herein by reference) (P < 0.00002, t-test for two populations).
M91-054 was the only sample that demonstrated a mixed phenotype in culture with both an epitheloid population and a more fibroblastic population Vasculogenic mimicry and gel contraction were only observed in the epitheloid population Scratch assay resulted in 30% closure after 24 h for both populations.
◻TC-1376 mRNA was isolated after short term (3 passage) culture of the biopsy sample from the patient TD-1376 allowing the effects of short term culture on the expression profile to be observed
**UACC-647 cells form extensive cord-like networks by 5 days Finally, in parallel to our microarray analysis of cutaneous melanoma, we studied a series of uveal melanoma specimens characterized for properties related to metastasis, including invasive ability and vasculogenic mimicry in vitro (Maniotis et al. "Vascular channel formation by human melanoma cells in vivo and in vitro: vasculogenic mimicry" Am. J. Pathol. 155:739–752, 1999; incorporated herein by reference). These samples were hybridized pairwise, directly comparing highly invasive cells to their less invasive counterparts. We examined the pattern of gene expression in these phenotypically characterized cells with respect to the weighted discriminator list (FIG. 2b) that defines the major cluster of 19 cutaneous melanomas. Strikingly, genes expressed in common in the highly invasive uveal melanoma cells (FIG. 2b, inset) were strongly anti-correlated with the same gene from the major cluster of cutaneous melanoma samples (FIG. 2b). This observation, coupled with the known biological function of genes within the weighted list, indicated that specimens assigned within the major cutaneous melanoma cluster (FIGS. 1a, b) would have reduced motility and reduced invasive ability as they have down-regulation of genes related to cell spreading or migration, including formation of focal adhesions (Adams "Characterization of cell-matrix adhesion requirements for the formation of fascin microspikes" Mol. Biol. Cell 8:2345–2363, 1997; Scott et al. "pp125FAK in human melanocytes and melanoma: expression and phosphorylation" Exp. Cell Res. 219:197–203, 1995; each of which is incorporated herein by reference). Specific genes with reduced expression in the major cluster included integrin β1 (Jannji et al. "Autocrine TGF-beta-regulated expression of adhesion receptors and integrin-linked kinase in HT-144 melanoma cells correlates with their metastic phenotype" Int. J. Cancer 83:255–262, 1999; Hieken et al. "Beta1 integrin expression in malignant melanoma predicts occult lymph node metastases" Surgery 118:669–673, 1995; each of which is incorporated herein by reference), integrin β3 (Van Belle et al. "Progression-related expression of beta3 integrin in melanomas and nevi" Hum. Pathol. 30:562–567, 1999; incorporated herein by reference), integrin α1 (Hieken et al. "Beta1 integrin expression in malignant melanoma predicts occult lymph node metastases" Surgery 118:669–673, 1995; incorporated herein by reference), syndecan 4 (Woods et al. "Syndecan-4 binding to the high affinity heparin-binding domain of fibronectin drives focal adhesion formation in fibroblasts" Arch. Biochem. Biophys. 374:66–72, 2000; incorporated herein by reference) and vinculin (Helige et al. "Interrelation of motility, cytoskeltal organization and gap junctional communication with invasiveness of melanocytic cells in vitro" Invasion Metastasis 17:26–41, 1997; incorporated herein by reference) (FIGS. 2 and 3; see Supplementary Information). In samples outside the major cluster increased expression of fibronectin is particularly interesting. With other reports (Maung et al. "Requirement for focal adhesion kinase in tumor cell adhesion" Oncogene 18:6824–6828, 1999; Silletti et al. "Autocrine motility factor and the extracellular matrix I. Coordinate regulation of melanome cell adhesion, spreading and migration involves focal contact reorganization" Int. J. Cancer 76:120–128, 1998; each of which is incorporated herein by reference), this observation indicates that these cells are induced to secrete this pro-migratory molecule, consistent with an important role for focal contacts in modulating melanoma cell motility.

Figure 4:
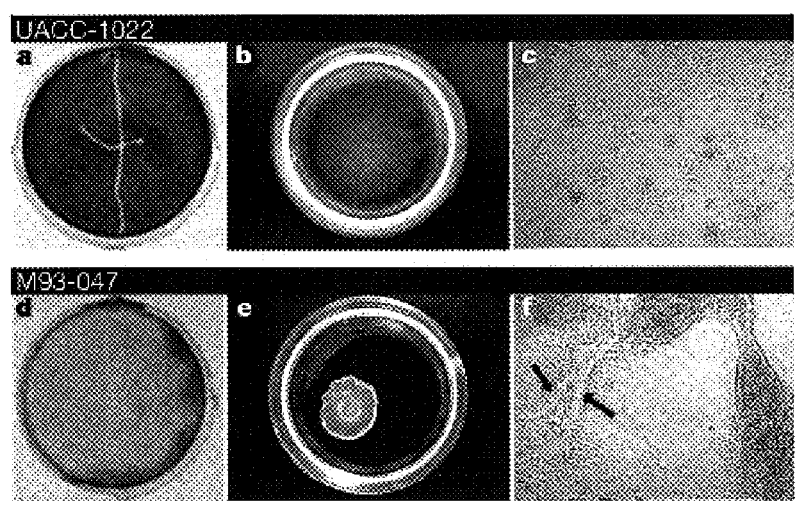
FIG. 4 shows the variation in biological properties of melanoma clusters. a–c. A representative member of the major melanoma cluster (UACC-1022). d–f. A sample falling outside of the major cluster (M93-047). The two groups differ in the ability to migrate into a scratch wound (a, d), contract collagen gels (b, e) and form tubular networks (c, f). Results of these and additional cell mobility/invasion assays are included in Table 1. Tubular network formation (vasculogenic mimicry (Maniotis et al. "Vascular channel formation by human melanoma cells in vivo and in vitro: vasculogenic mimicry" *Am. J. Pathol.* 155:739–752, 1999; incorporated herein by reference), f) and collagen gel contraction (related to the patterning of vascular channels, e) were observed only outside the major cluster (Table 1).

We then directly tested the prediction from the array results that cell spreading and migration could be discordant between melanoma cluster groups. Cutaneous melanomas (assigned either in or out of the major cluster) were characterized using a series of cellular assays applied to test cell motility and invasiveness (Table 1, FIG. 4). FIG. 4 illustrates the discordance of cutaneous melanoma samples within the major cluster and those outside this group. As predicted from the analysis of their gene expression patterns, melanomas within the major cluster had reduced motility (P=0.0063), invasive ability (P=0.0055) and vasculogenic mimicry in comparison with melanomas outside the major cluster (Table 1).

The patient population in this study had a uniformly poor prognosis, and neither typical clinical factors (for example, age, sex, biopsy site) nor in vitro characteristics (for example, passage number) provide strong correlation with clinical outcome, or expression information (see Supplementary Information). In contrast, molecular classification of these tumors on the basis of gene expression (FIG. 1, Table 1) could identify a previously undetected subtype of this cancer. The analyses described here were not designed to address the relationship of gene expression profile and clinical outcome in melanoma patients, and thus the clinical relevance of our observed subgrouping awaits further analysis. However, survival information was available on 15 patients, and the results, though not statistically significant, are of interest. Three deaths occurred out of 10 patients in the tight cluster of 19 while 4 deaths occurred out of 5 patients in the remaining group (log-rank P-value=0.135). Our results indicate melanoma will provide a unique opportunity to study a homogeneous group of patients to determine if gene expression patterns predict prognosis or therapeutic response in settings where we cannot currently determine who is most at risk for rapid disease progression and death.

Finally, classification of melanoma on the basis of gene expression patterns is possible, despite the prevailing view that the 'taxonomy' of this disease falls in a continuous spectrum lacking discernible entities. Our data show that melanoma is a useful model to identify genes critical for aspects of the metastatic process, including tumour cell motility and the ability to form primitive tubular networks that may contribute to tumour perfusion. The extent to which melanoma samples can be clinically subdivided by expression patterns remains to be elucidated. However, our identification of genes 'weighted' for their ability to discriminate a subset of melanomas should provide a sound molecular basis for the dissection of other clinically relevant subsets of this tumur.

Methods

Samples

Cultured cells were collected and mRNA isolated as described (Khan et al. "DNA Microarray technology: the anticipated impact on the study of human disease" *Biochim. Biophys. Acta* 1423:17–28, 1999; each of which is incorporated herein by reference). Samples underwent a series of controls for quality of mRNA, labeling and hybridization, as well as sample integrity (including genotyping DNA from all samples with five dinucleotide markers from four different chromosomes to insure individuality). The entire coding sequence of the p16 gene and exon 3 of the β-catenin genes was sequenced to assess the mutation status of all available samples (see Supplementary Information). The biopsy tumor specimens used in this study were obtained with Institutional Review Board approval and clinical information is provided in the Supplementary Information. Biopsies were debrided, dissected into small pieces and frozen in liquid nitrogen. Frozen specimens were immediately placed into TRIzol Reagent (Gibco BRL), homogenized and mRNA isolated as described (Khan et al. "DNA Microarray Technology: The Anticipated Impact on the Study of Human Disease" *Biochim. Biophys. Acta* 1423:17–28, 1999;

each of which is incorporated herein by reference).

Microarrays

The 8,150 human cDNAs used in this study were obtained under a Cooperative Research and Development Agreement with Research Genetics and 6,912 were verified by sequence. This set of cDNAs is part of a larger collection (Khan et al. "Gene expression profiling of alveolar rhabdomyosarcoma with cDNA microarrays" *Cancer Res.* 58:5009–5013, 1998; Duggan et al. "Expression profiling using cDNA microarrays" *Nature Genet.* 21:10–14, 1999; each of which is incorporated herein by reference). On the basis of the Unigene build of 9 Mar. 2000, the 8,150 cDNAs represent 6,971 unique genes in this melanoma array. All clones were confirmed by resequencing if necessary. Microarrays were hybridized, scanned and image analysis performed as described (Khan et al. "Gene expression profiling of alveolar rhabdomyosarcoma with cDNA microarrays" *Cancer Res.* 58:5009–5013, 1998; Khan et al. "DNA Microarray technology: the anticipated impact on the study of human disease" *Biochim. Biophys. Acta* 1423: 17–28, 1999; each of which is incorporated herein by reference). The raw data from the microarray is shown in Appendix A, a Microsoft Excel Worksheet, which has been included on a CD-ROM submitted with this application and is incorporated herein by reference.

Statistical Methods

Detailed information on all statistical methods is in the Supplementary Information. Agglomerative hierarchical clustering of the 31 melanomas on the basis of their gene expression profiles was performed as described (Khan et al. "Gene expression profiling of alveolar rhabdomyosarcoma with cDNA microarrays" *Cancer Res.* 58:5009–5013, 1998; Bittner et al. "Data analysis and integration of steps and arrows" *Nature Genet.* 22:213–215, 1999; each of which is incorporated herein by reference), to investigate relationships between tumour samples. Average linkage was used, as well as a dissimilarity measure of one minus the Pearson correlation coefficient of log ratios. The cutoff employed to obtain the observed partitioning was 0.54. The MDS was performed using an implementation of MDS in the MATLAB package. A non-hierarchical clustering algorithm (Ben-Dor et al. "Clustering gene expression patterns" *J. Comput. Biol.* 6:281–297, 1999; incorporated herein by reference) was used to define experimental clusters. This approach takes a graph theoretic approach, and makes no assumptions on the similarity function or the number of clusters sought.

To generate the weighted gene list, cluster compaction and separation were evaluated. For a given clustering result, $n_1=19$ and $n_2=12$, the discriminative weight of each gene $w=d_B/(k_1 d_{w1}+k_2 d_{w2}+\alpha)$; where $d_B$ is the centre-to-centre distance (between cluster Euclidean distance), $d_{w1}$ is the average Euclidean distance among all sample pairs within cluster i, $k_i=t_i/(t_1+t_2)$ for a total of t; sample pairs in cluster i, and $\alpha$ is a small constant (0.1 in our study) to prevent the zero denominator case (FIG. 2a). Genes may then be ranked on the basis of w.

In vitro Biological Assays

Floating collagen lattices were prepared and used to test selected cell lines for their ability to deform the gels as described (Maniotis et al. "Vascular channel formation by human melanoma cells in vivo and in vitro: vasculogenic mimicry" *Am. J. Pathol.* 155:739–752, 1999; Table 1 legend). Samples were also tested for their ability to migrate into an in vitro scratch wound as described (Tamura et al. "Inhibition of cell migration, spreading and focal adhesions by tumor suppressor PTEN" *Science* 280:1614–1617, 1998; incorporated herein by reference). Cells were stained with Giemsa, a digital micrograph of the region was prepared and the stained area as a percent of total area in the scraped and open sub-regions was estimated by a thresholding procedure using IPLabs Spectrum (Scanalytics, Vienna, Va.) software. Results in Table 1 represent data from 24 h after plating on coverslips treated with fibronectin (FN; 10 µg ml$^{-1}$; Tamura et al. "Inhibition of cell migration, spreading and focal adhesions by tumor suppressor PTEN" *Science* 280:1614–1617, 1998; incorporated herein by reference).

Examples of tubular network formation (associated with vasculogenic mimicry) could be observed following seeding of cell lines onto three-dimensional gels of polymerized Matrigel or Type 1 collagen (Collaborative Biochemical) as described (Maniotis et al. "Vascular channel formation by human melanoma cells in vivo and in vitro: vasculogenic mimicry" *Am. J. Pathol.* 155:739–752, 1999; Table 1).

Table 1 lists results from high throughput screening for cell migration as the radial dispersion of cells from an initial confluent monolayer of 2,000 melanoma cells deposited within a 1.0 mm circular area on glass surfaces precoated with FN (100 µg ml$^{-1}$; Berens et al. "The role of extracellular matrix in human astrocytoma migration and proliferation studied in a microliter scale assay" *Clin. Exp. Metastasis* 12:405–415, 1994; Giese et al. "Contrasting migratory response of astrocytoma cells to tenascin mediated by different integrins" *J. Cell Sci.* 109:2161–2168, 1996; each of which is incorporated herein by reference).

Selected cell lines were tested for their ability to invade a defined basement membrane matrix. Tumor cells ($1\times10^5$) were seeded into the upper wells of the membrane invasion culture system (MICS) chamber (Hendrix et al. "A simple quantiative assay for studying the invasive potential of high and low human metastatic variants" *Cancer Lett.* 38:137–147, 1987; incorporated herein by reference) onto collagen/laminin/gelatin-coated (Sigma) polycarbonate membranes containing 10-µm pores (Osmonics, Livermore, Calif.) containing 1× Mito+ Serum Extender (Becton Dickinson). After 24 h of incubation at 37° C., the cells that invaded each membrane were collected, stained and counted as described (Hendrix et al. "Role of intermediate filaments in migration, invasion and metastasis" *Cancer Metastasis Rev.* 15:507–525, 1996; incorporated herein by reference). Percent invasion was corrected for proliferation and calculated as (total number of invading cells/total number of cells seeded)×100.

Supplement I—Statistical Methods for Clustering of Gene Expression Data and Validation of Cluster Predictions Overview:

To fully appreciate the expression patterns derived from large number of cDNA microarrays and their relationship between melanoma tumor samples, several statistical methods were integrated as follows, a. Multidimensional scaling (MDS) method was employed in order to visualize the similarity between samples, and a hierarchical clustering dendrogram was produced by an implementation of the average-linkage clustering algorithm, b. The clustering results were further verified by a non-hierarchical algorithm, CAST (Ben-Dor et al. *J. Comput. Biol.* 6:281–297, 1999; incorporated herein by reference), c. In order to determine the tightness and the statistical significance of the clusters derived from various methods, two independent approaches were assembled to validate the prediction. One, $WADP_k$ method, is sensitivity analysis of the noise perturbation to the data set. The other one is based on comparing the discrimination power observed for genes in the data to that expected in random data. This is accomplished using TNoM scoring.

d. After confirming the clustering result, each gene was weighted based on their discriminative ability for the clusters derived from previous method.

In the following section, detailed descriptions of the methods listed in Steps 3 to 4 will be presented. For some of the more standard methods, such as MDS, average-linkage methods, and CAST, we refer readers to the literature (Ben-Dor et al. *J. Comput. Biol.* 6:281–297, 1999; Eisen et al. *Proc. Natl. Acad. Sci. USA* 95:14863–14868, 1998; Everitt *Cluster Analysis* (London: Edward Arnold), 1993; each of which is incorporated herein by reference). Since not all genes were readily detectable by the array method, a subset of the total number of surveyed genes was analyzed in all cases. A set of 3613 genes was chosen for analysis. The genes were chosen by an empirically derived set of criteria requiring an average mean intensity above background of the least intense signal (Cy3 or Cy5) across all experiments>2000 arbitrary units, and an average spot size across all experiments of >30 pixels. To avoid distortions of the data resulting from ratios where the signal in one channel is large, and the signal in the other channel is undetectable, ratios higher than 50 or lower than 0.02 were truncated to 50 or 0.02 for these analyses.

Description of the $WADP_k$ Method for Testing the Validity of Cluster Predictions Hierarchical clustering of the 31 melanoma samples was performed, resulting in a dendrogram (FIG. 1). Although the dendrogram gives insights about the similarity and relatedness among samples, it does not indicate robustness to variability associated with the assay sampling, etc. In order to draw valid conclusions about the clustering structure present in the data, it is necessary to investigate how variability affects the results of the cluster analysis. To this end, we developed and implemented a method that determines the reproducibility of given levels of cluster structure within the dendrogram under the condition of added noise. The method is described below.

First, cut the original dendrogram at a height that results in k clusters and let $N_k$ denote the number of clusters containing 2 or more elements. Let $M_i$ represent the number of pairs of elements in the $i^{th}$ of the $N_k$ clusters. Next, perturb the data by adding to every log-ratio of each sample an independent random deviate generated from the $N(0,\Box)$ distribution. Cluster the perturbed data and cut the resulting dendrogram at a height that again results in k clusters. For the $M_i$ pairs of elements in the $i^{th}$ original cluster, record the number of those pairs, $D_i$ that do not remain together in the clustering of the perturbed data. Next, calculate the overall discrepancy rate for the clustering: $(D_1+D_2+\ldots+D_{N_k})/(M_1+M_2+\ldots+M_{N_k})$. This overall discrepancy rate is a weighted average of the $N_k$ cluster-specific discrepancy rates (i.e., $D_i/M_i$, for $i=1, 2, \ldots, N_k$), with weights proportional to the number of pairs in individual clusters. Finally, repeat the calculations over many perturbations of the original data set and report the average overall discrepancy rate (termed the Weighted Average Discrepant Pairs for k clusters, or $WADP_k$). The above procedure is repeated for all possible cuts of the original dendrogram and $WADP_k$ is plotted versus k. Minima of the WADP curve are interpreted as indicating reproducible levels of structure.

The parameter σ represents the noise standard deviation inherent to the system. As mentioned above, the noise is composed of—at the least—assay variability and sampling variability. σ is unknown and must be estimated. The method we use for estimating σ is to compute the variance of the log-ratio of each gene across all samples. We then use the median of the empirical distribution of these variances as an estimate of $\sigma^{-2}$ It may be more appropriate to use a smaller value (say the tenth percentile of the empirical distribution), if it were believed that a large percentage of genes present on the array were truly differentially expressed within the population of samples hybridized.

Description of the TNoM Method for the Cluster Significance Based on Random Partition.

Threshold number of misclassification, or TNoM score, is a simple threshold-based method that uses a given expression level, for a given gene, to predict the cluster label of a given test sample. In the present study, we have 31 samples form 2 groups. Therefore, we can label the samples by $l_i$, $i=1, \ldots, m$, where $l_i \in \{0,1\}$ and $m=31$. For the kth gene, let $<x_i, l_i>_k$ be its expression pattern (or ratios in this study) and corresponding cluster labels. A threshold function is defined as, $$f_{h,a}(x) = \begin{cases} a, & \text{if } x < h \\ 1-a & \text{otherwise} \end{cases}$$

where h is a threshold value, and a∈{0,1}. For a given h and a we can assign the label $f_{h,a}(x_i)$ to the ith sample. The number of misclassifications entailed by this scheme is, $$e = \sum_{i=1}^{m} |l_i - f_{h,a}(x_i)|$$

The TNoM score for the kth gene, $s_k$, is defined as the minimum error achieved over all possible choices of h and a, $$s_k = \min_{h,a} \left( \sum_{i=1}^{m} |l_i - f_{h,a}(x_i)| \right)$$

The minimization step is accomplished by exhaustively searching all 2(m+1) possibilities.

To examine the significance of groups derived by clustering algorithm, we used three steps. First, we evaluated TNoM scores for all genes found in the data set. Then, the number of genes that have TNoM score less than or equal to s, for s=0, . . . , 12 (where 12 is the maximum misclassifications any classification rule may commit) was listed. Next, we randomly assigned cluster labels to all samples to form two arbitrary groups of 19 and 12 samples. The TNoM score was again evaluated for each gene. A list of the number of genes that have TNoM score less than or equal s was similarly obtained. We repeated this process 50 times to observe random fluctuations and their range of scores. Finally, the expected number of genes resulting in s or fewer misclassifications under the assumption of perfect random gene expression patterns can be calculated (Ben-Dor et al., submitted for publication). As expected, the value produced by the 50 random sampling is close to those produced by the theoretical rigorous calculation. The significance of the suggested clusters is reflected in the overabundance of genes with low TNoM scores. More precisely, a meaningful partition will produce far more genes with low TNoM scores than a random one.

Description of the Weighting Method Based on Gene's Discriminative Ability.

The clustering algorithms described in the text produced one tightly bonded cluster of $n_1$=19 samples, and we assume the rest of $n_2$=12 samples form another cluster. For a given two-cluster setting, a discriminative weight for each gene can be evaluated by, $$w = d_B/(k_1 d_{w_1} + k_2 d_{w_2} + \alpha)$$

where $d_B$ is the center-to-center distance (between cluster Euclidean distance), $d_{w_1}$ is the average Euclidean distance among all sample pairs, total of $t_1$ and $t_2$ sample pairs for cluster 1 and 2, respectively, and $k_1 = t_1/(t_1+t_2)$, and $k_2 = t_2/(t_1+t_2)$. $\alpha$ is a small constant (0.1 in our study) to prevent zero denominator case. Genes may then be ranked on the basis of w. The equation for weight w is not only designed to evaluate discriminative ability for single gene, but also capable of evaluate discriminative ability for 2 or more genes together. If you do not assume the second group of samples to be a tight cluster you can drop the $d_{w_2}$ term.

Supplement II—Statistical Analysis of Clinical and Culture Characteristics of Melanoma Clusters Summary Report:

Thirty-one tissue specimens were clustered using the Bioclust clustering algorithm (see text), resulting in one tight cluster of 19 specimens (Group A) and 12 specimens that showed no specific clustering pattern (Group B). Statistical tests were performed to determine whether any clinical or tumor cell characteristics were specifically associated with cluster group. For categorical variables we created a contingency table and used Fisher's exact test to compute a p-value (the Chi-square test was not used because each table had at least one expected cell frequency less than 5). For continuous and ordered variables, we used the Wilcoxon two-sample (rank-sum) test, a non-parametric alternative to the two-sample t test. Tests were performed in S-plus 4.5 and StatXact 3.1.

The two groups consisted of the following patient IDs:

| Group A | | | | | Group B | |
|---|---|---|---|---|---|---|
| M93-007 | M91-054 | UACC091 | UACC502 | HA-A | UACC827 | UACC1529 |
| UACC1256 | UACC127 | UACC253 | M92-001 | UACC647 | UACC930 | M93-047 |
| UACC457 | UACC383 | UACC309 | A-375 | UACC2837 | TC-F027 | WM1791C |
| UACC1022 | TD1376-3 | TD1683 | TD1720 | UACC1012 | UACC1097 | UACC903 |
| TD1384 | TD1730 | TC1376-3 | | | | |

As noted in the text, two pairs of specimens in Group A were derived from the same patient. The two pairs are M93-007 & M92-001 and TD1376-3 & TC1376-3. In our analyses, we only considered the data for each of these patients once or, as specifically noted, entirely removed the specimens for these patients from the analysis.

We first performed an analysis that included all specimen types (tissues and cell lines). We tested for associations between group and the following variables: sex, age, mutation status, biopsy site*, pigment, Breslow thickness, Clark level, and specimen type. There was no variable tested, which was shown to be associated with cluster group (at the 0.05 significance level.

*Biopsy site was broken down into the following three categories: skin/external (including ankle, abdomen/chest, shoulder, breast, neck/forehead and back), internal (including chest wall, distal ileum, paraspinous, thyroid lobe, small bowel, rectus muscle and intra-abdominal), and lymph nodes (including axillary, cervical and thigh femoral).

Although there was not a statistically significant association between group and specimen type (p=0.106) it was noteworthy that all 5 tissue specimens were located in Group A. We therefore performed another analysis in which we only considered data from cell lines. In the analysis of cell lines, no variables were associated with cluster group at the 0.05 significance level, although "age" did have a marginal association (p=0.0812). Passage number was also tested in this analysis and had no association with group (p=0.8570).

Next, we investigated for differences in survival between the two cluster groups. We used a measure of survival that indicated survival time from the date of biopsy. Four cases (including the previous two) had a biopsy date falling in 1998 and a known status (alive or dead) for which a specific date of death or last follow-up was unknown. In order to use these cases in the survival analysis, the survival/follow-up time in these cases was arbitrarily set to 1 year if the biopsy date occurred prior to Jul. 1, 1998 or 0.5 years if the biopsy date occurred on or after Jul. 1, 1998.

A total of 15 cases were included in the analysis, 10 from Group A and 5 from Group B. Survival/follow-up times were rounded to the nearest quarter year. A Kaplan-Meier survival plot was created and log-rank test performed. No statistically significant association between group and survival was found (p=0.135).

The analyses performed resulted in no significant association with cluster group. However, this does not necessarily mean associations do not exist between the groups and the clinical and tumor characteristics tested. The power of the tests we performed is limited by the amount of data available for each variable. For example, only 6 specimens in Group A and 3 in Group B have information on Breslow thickness. Finding significant associations with so few data is unlikely. The power of the tests would increase with more complete data on the existing specimens and by the addition of new specimens to the data set. Such studies are underway in our laboratory.

Analysis of All Specimens:
Group A=specimens that cluster; Group B=others.
Two pairs of specimens in Group A (M93-007/M92-001 & TD1376-3/TC1376-3) were derived from the same patient. The clinical and tumor characteristics for each of these patients are only considered once in the below analyses.

Sex—No Statistically Significant Association with Group
Contingency Table with Fisher's Exact Test

|   | A | B |   |
|---|---|---|---|
| F | 4 | 4 | p-value = 0.6754 |
| M | 12 | 7 | alternative hypothesis: two-sided |

Age—No Statistically Significant Association with Group
Wilcoxon Rank-sum Test: p-value=0.1397
data: x: age w/group=A, and y: age w/group=B
Mann-Whitney Statistic: W=102.0, n=15, m=10
alternative hypothesis: two-sided Mutation Status—No Statistically Significant Association with Group
Contingency Table with Fisher's Exact Test

|   | A | B |   |
|---|---|---|---|
| mutated | 2 | 4 | p-value = 0.1713 |
| deleted | 6 | 1 | alternative hypothesis: two-sided |
| WT | 4 | 2 |   |

Contingency Table with Fisher's Exact Test
Combined mutated and deleted into one category.

|   | A | B |   |
|---|---|---|---|
| mut./del. | 8 | 5 | p-value = 1 |
| WT | 4 | 2 | alternative hypothesis: two-sided |

Biopsy Site—No Statistically Significant Association with Group
Contingency Table with Fisher's Exact Test

|   | A | B |   |
|---|---|---|---|
| skin/external | 3 | 3 | p-value = 0.8763 |
| internal | 4 | 3 | alt. hypothesis: two-sided |
| LN | 7 | 4 |   |

Pigment—No Statistically Significant Association with Group
Wilcoxon Rank-sum Test: p-value=0.2631
Pigment Type: light=1, med=2, dark=3
(amelanotic=light; tan=med; pigmented=dark.)
data: x: pig. type w/group=A, and y: pig. type w/group=B
Mann-Whitney Statistic: W=76.5, n=13, m=9
alternative hypothesis: two-sided Breslow Thickness—No Statistically Significant Association with Group
Wilcoxon Rank-sum Test: p-value=0.2619
data: x: thickness w/group=A, and y: thickness w/group=B
Mann-Whitney Statistic: W=14.0, n=6, m=3
alternative hypothesis: two-sided Clark Level—No Statistically Significant Association with Group
Wilcoxon Rank-sum Test: p-value=0.4481
Clark level: II=2, III=3, IV=4
data: x: Clark level w/group=A, and y: Clark level w/group=B
Mann-Whitney Statistic: W=19.5, n=6, m=5
alternative hypothesis: two-sided For the below analysis, the two pairs of specimens in Group A derived from the same patient (M93-007/M92-001 & TD1376-3/TC1376-3) were removed.

Specimen Type—No Statistically Significant Association with Group
Contingency Table with Fisher's Exact Test

|   | A | B |   |
|---|---|---|---|
| cell line | 11 | 12 | p-value = 0.106 |
| tissue | 4 | 0 | alternative hypothesis: two-sided |

Analysis of Cell Cultures:
Group A=specimens that cluster; Group B=others.
A pair of cell lines in Group A (M93-007/M92-001) was derived from the same patient. The clinical and tumor characteristic for this patient is only considered once in the below analyses.

Sex—No Statistically Significant Association with Group
   Contingency Table with Fisher's Exact Test

|   | A | B |   |
|---|---|---|---|
| F | 4 | 4 | p-value =1 |
| M | 8 | 7 | alternative hypothesis: two-sided |

Age—No Statistically Significant Association with Group
   Wilcoxon Rank-sum Test: p-value=0.0812
   data: x: age w/group=A, and y: age w/group=B
   Mann-Whitney Statistic: W=80.0, n=11, m=10
   alternative hypothesis: two-sided Mutation Status—No Statistically Significant Association with Group
   Contingency Table with Fisher's Exact Test

|   | A | B |   |
|---|---|---|---|
| mutated | 2 | 4 | p-value = 0.1713 |
| deleted | 6 | 1 | alternative hypothesis: two-sided |
| WT | 4 | 2 |   |

Contingency Table with Fisher's Exact Test
Combined mutated and deleted into one category.

|   | A | B |   |
|---|---|---|---|
| mut./del. | 8 | 5 | p-value = 1 |
| WT | 4 | 2 | alternative hypothesis: two-sided |

Biopsy Site—No Statistically Significant Association with Group
   Contingency Table with Fisher's Exact Test

|   | A | B |   |
|---|---|---|---|
| skin/external | 2 | 3 | p-value = 0.7272 |
| internal | 2 | 3 | alt. hypothesis: two-sided |
| LN | 6 | 4 |   |

Pigment—No Statistically Significant Association with Group
   Wilcoxon Rank-sum Test: p-value=0.4212
   Pigment Type: light=1, med=2, dark=3
   amelanotic=light; tan=med; pigmented=dark.
   data: x: pig. type w/group=A, and y: pig. type w/group=B
   Mann-Whitney Statistic: W=50.5, n=9, m=9
   alternative hypothesis: two-sided Breslow Thickness—No Statistically Significant Association with Group
   Wilcoxon Rank-sum Test: p-value=0.2000
   data: x: thickness w/group=A, and y: thickness w/group=B
   Mann-Whitney Statistic: W=8.0, n=3, m=3
   alternative hypothesis: two-sided Clark Level—No Statistically Significant Association with Group
   Wilcoxon Rank-sum Test: p-value=0.6349
   Clark level: II=2, III=3, IV=4
   data: x: Clark level w/group=A, and y: Clark level w/group=B
   Mann-Whitney Statistic: W=13.0, n=4, m=5
   alternative hypothesis: two-sided For the below analysis, the pair of specimens derived from the same patient in Group A (M93-007/M92-001) was removed.

Passage Number—No Statistically Significant Association with Group
   Wilcoxon Rank-sum Test: p-value=0.8570
   Passage #'s for established cell lines were set equal to 21.
   data: x: passage # w/group=A, and y: passage # w/group=B
   Mann-Whitney Statistic: W=34.0, n=8, m=8
   alternative hypothesis: two-sided
   Contingency Table with Fisher's Exact Test

|   | A | B |   |
|---|---|---|---|
| 1–5 | 3 | 4 | p-value = 0.8695 |
| 6–10 | 4 | 2 | alternative hypothesis: two-sided |
| 11–20 | 4 | 5 |   |
| >20 | 1 | 1 |   |

Survival Analysis:

Data used in the survival analysis:

| Pt.ID | Group | Status | Time |
|---|---|---|---|
| M93-007 | A | 0 | 7 |
| M91-054 | A | 0 | 7 |
| UACC091 | A | 0 | 7 |
| UACC502 | A | 1 | 0.5 |
| UACC2534 | A | 1 | 0.25 |
| TD1683 | A | 1 | 1 |
| TD1720 | A | 0 | 0.5 |
| TD1348 | A | 0 | 5 |
| TD1730 | A | 0 | 0.5 |
| TC1376-3 | A | 0 | 3 |
| UACC827 | B | 1 | 0.5 |
| UACC930 | B | 1 | 2.25 |
| M93-047 | B | 0 | 6 |
| TC-F027 | B | 1 | 1 |
| UACC903 | B | 1 | 0.25 |

Status: 0 = alive, 1 = dead
Time is in years.

Example 2

Expression of Wnt5a in Cell Lines with Originally Low Level Expression

Wnt5a scored very high out of all the marker genes analyzed in the ability to discriminate between highly invasive malignant melanoma and less invasive melanoma. Melanoma samples with high levels of Wnt5a expression were more aggressive tumors than those with lower levels of Wnt5a expression. FIG. 2B shows the top 22 genes selected for their ability to classify highly invasive malignant melanoma from less invasive melanoma. Wnt5a is at the tope of the list of these marker genes.

FIG. 5 also shows Wnt5a's expected signaling pathway in contrast to the Wnt1 pathway. Wnt1 is known to be transforming; however, its proximal methods of signaling are very different from those of Wnt5a. In some studies, researchers have observed that the two pathways seem to oppose each other in terms of downstream effects. In the Wnt5a pathway, the first transduction of the Wnt5a signal is accomplished through the interaction of Wnt5a with a G protein-coupled receptor, frizzled 5 (FZD5). The signal is subsequently transduced through the PLC/IP3/DAG/PKC pathways. The Wnt5a signal eventually leads to integrin interactions, cytoskeletal effects, and other cellular effects.

Figure 6A:
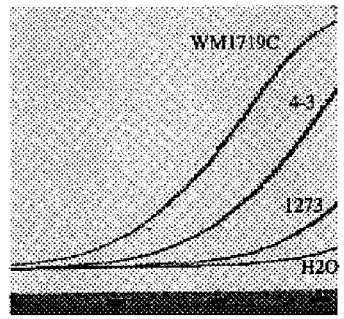
FIG. 6 shows the data from real time PCR analysis of three cell lines, one with low Wnt5a expression (which scored as having low expression in the gene chip analysis), one with high Wnt5a expression (which scored as having high expression in the gene chip analysis), and one with intermediate Wnt5a expression, an originally low scoring cell line which had been transfected with a vector designed to express Wnt5a. The patent and transfected cell line were also analyzed for WNT5A protein abundance using Western blot analysis and immunohistochemical staining.
Figure 6B:
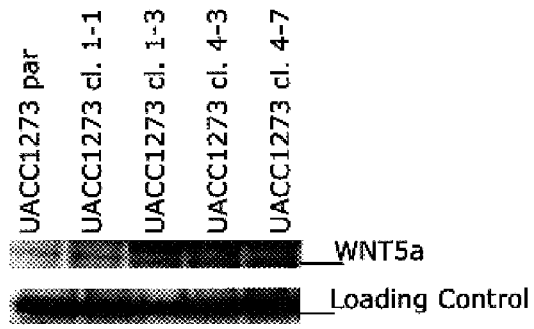
Figure 6C:
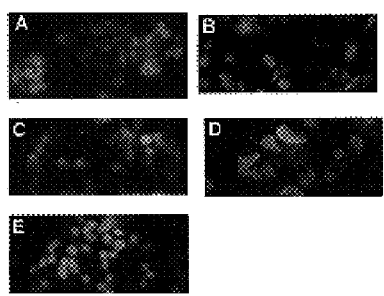

Low level expression of Wnt5a in the cluster of 19 melanomas was verified by real time PCR. Data for the samples WM-1791C and UACC-1273 are shown in FIG. 6A. The real time PCR results show that there is much more Wnt5a transcript in cell line WM-1791C, which originally was scored as having high level expression of Wnt5a by gene chip analysis, than in UACC-1273, which was originally scored as having low level expression. Vectors used to express higher levels of Wnt5a in cells that normally express low levels were developed using standard techniques to see if the phenotype of less aggressive samples expressing low levels of Wnt5a could be changed. A derivative of UACC-1273, a transfectant 4-3, which had been transfected with this vector, shows an intermediate level of Wnt5a expression in the real time PCR analysis. The increase in Wnt5a expression carries over in WNT5A protein abundance as shown by Western blot and by immunohistochemical staining (nuclei staining blue, WNT5A staining red) (FIGS. 6B and 6C).

Figure 7A:
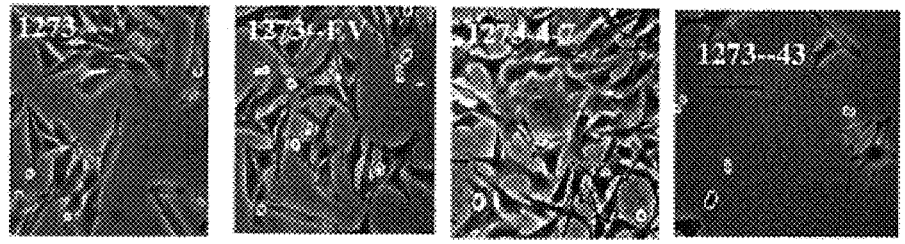
FIG. 7 shows the dramatic changes in cell morphology and cytoskeletal organization upon transfection of the parental cell line with a vector driving Wnt5a expression. The parental cell line is spindle shaped with few points of attachment to the culture plate and disorganized actin filaments. The transfectants are broader and flatter with many extensions and highly polarlized actin filaments.
Figure 7B:
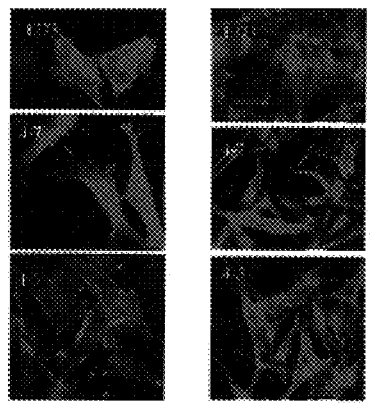

In terms of morphology, cell lines with originally low levels of Wnt5a expression showed dramatic changes in morphology and cytoskeletal organization when stably transfected with a vector driving Wnt5a expression. The parental line, UACC-1273, is spindle shaped with few points of attachment to the culture plate and disorganized actin filaments (FIG. 7). The transfectants are broader and flatter with many extensions and highly polarized actin filaments.

Figure 8A:
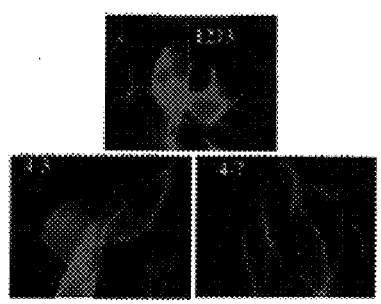
FIG. 8 shows the results of experiments done to look at possible cross talk between the Wnt5a and Wnt1 pathways. Beta-catenin was localized to the cytoplasm indicating that the Wnt1 pathway is not active. The downstream target of Wnt5a, protein kinase C, was also observed to be phosphorylated, especially the mu and alpha/beta isoforms, indicating that the expected Wnt5a pathway is active.
Figure 8B:
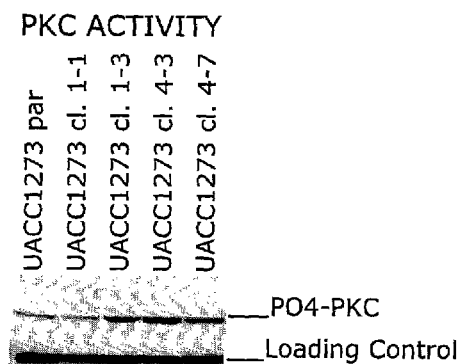
Figure 8C:
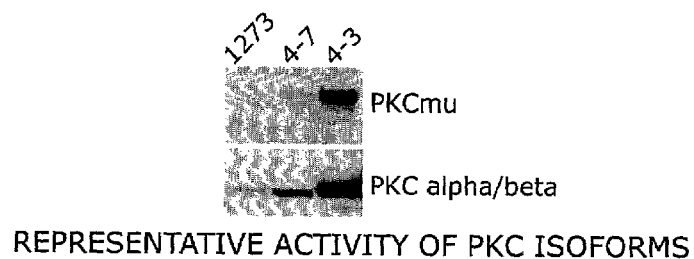
Figure 8D:
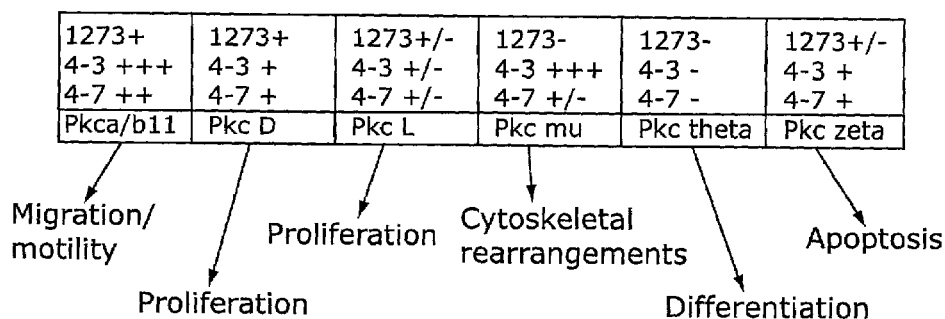

In order to determine whether there was cross talk between the Wnt5a and Wnt1 pathways, an assay looking at beta-catenin was used. When Wnt1 signaling is active, beta-catenin is localized to the nucleus. In FIG. 8A, antibody staining for beta-catenin shows that the beta-catenin is localized in the cytoplasm and not concentrated in the nucleus. Therefore, no cross talk between the two pathways seems to be occurring.

Protein kinase C (PKC), a downstream target likely to be modulated by Wnt5a, was also looked at. Wnt5a modulates PKC activity by phosphorylation of some or all of the PKC isoforms and not by alteration of PKC transcript levels. As can be seen in FIG. 8, increased phosphorylated PKC is produced in the transfectants expressing significant levels of the Wnt5a transcript, as expected. The isoforms must frequently phosphorylated are mu and alpha/beta. This is further evidence that one is looking at the exptected Wnt5a pathway. PKC is one of the central hubs of signal transduction, and pathways leading to many types of cellular action incuding proliferation, cytoskeletal organization, and cell movement are known.

Figure 9A:
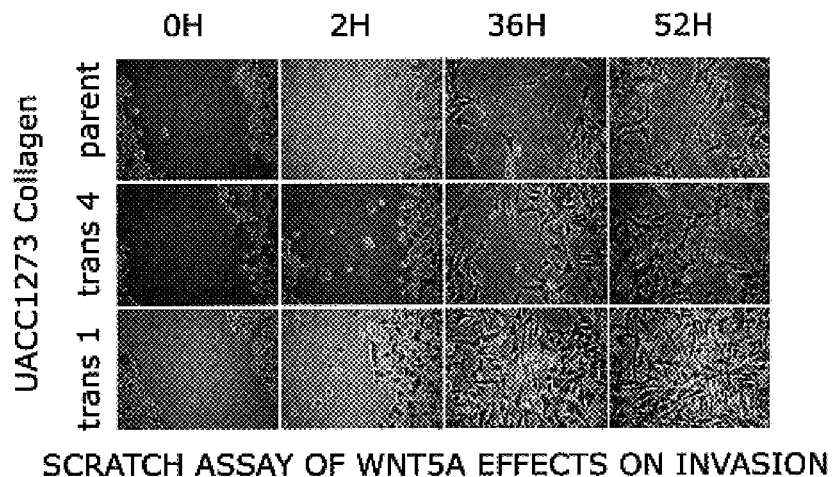
FIG. 9 shows scratch assay and Boyden chamber assay results for the parent cell line as well as the transfected cell line. The results from these two standard assays show that increased cell movement and invasiveness correlate with increased Wnt5a expression.
Figure 9B:
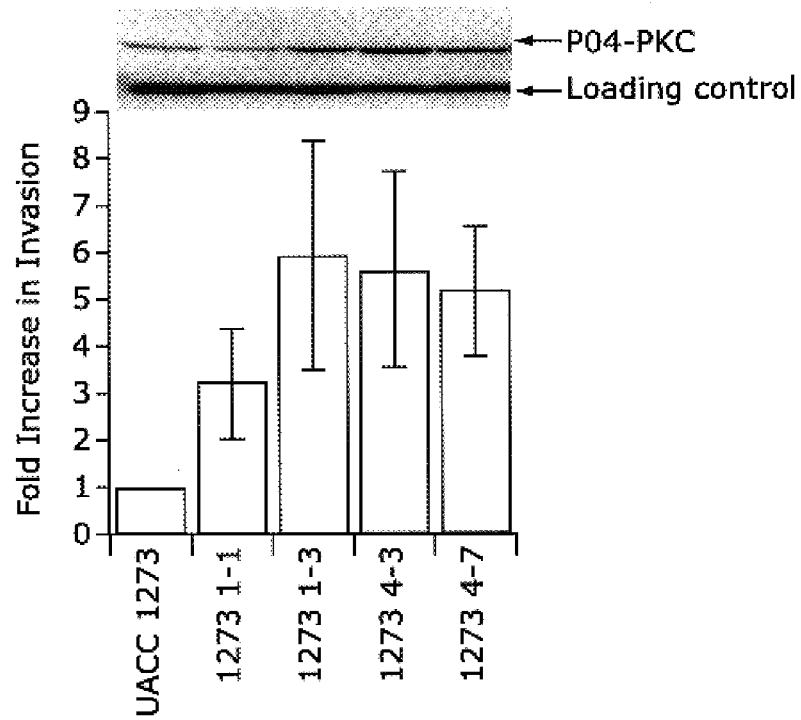
Figure 10A:
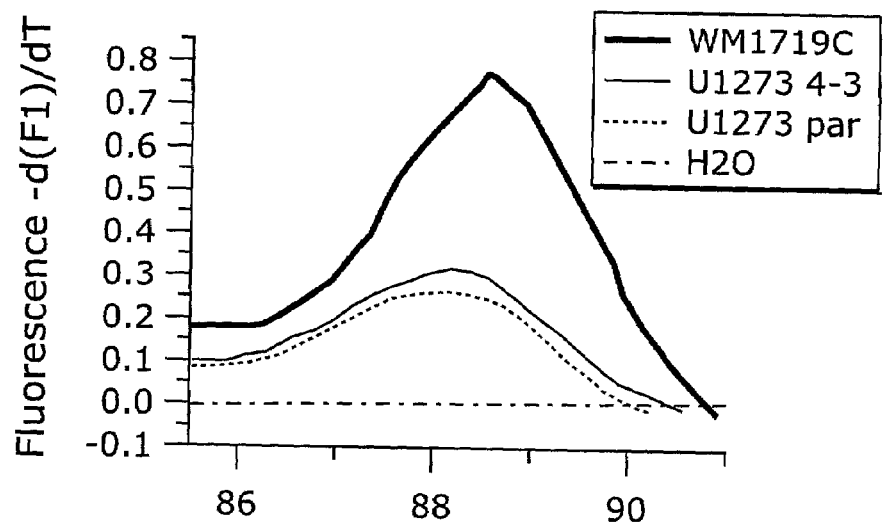
FIG. 10 shows that the transition from low to high Wnt5a expression is not associated with increasing amounts of the G protein coupled receptor, frizzled 5 (fzd5). Also shown are results indicating that an antibody to fzd5 can attenuate or reverse the phenotype that increased Wnt5a would normally produce.
Figure 10B:
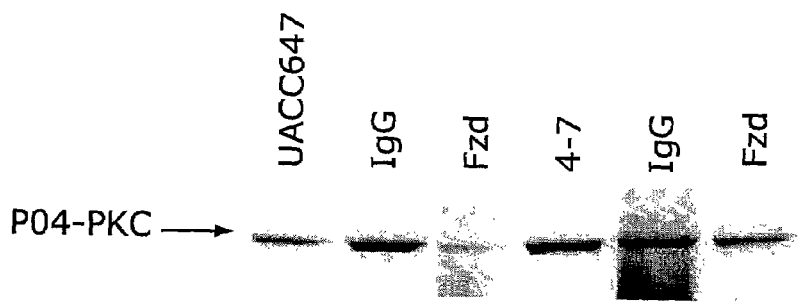
Figure 10C:
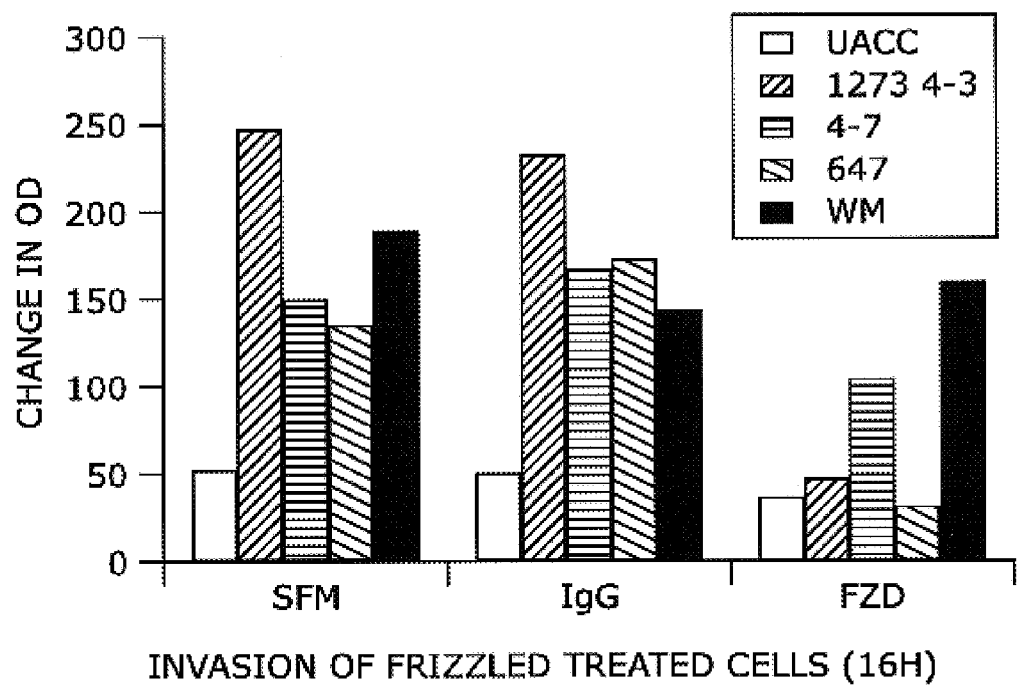
Figure 10D:

Increased cell movement and invasiveness were also found to correlate with increased Wnt5a expression in a scratch assay and a Boyden chamber assay. Transfectants expressing increased levels of Wnt5a show increased competence in filling in open gaps on a cell culture dish when compared to cells of the parent cell line (FIG. 9). Increased phosphorylated PKC was found to correlate with increasing cell invasiveness as measured by a standard test for invasiveness, the Boyden chamber assay.

The first transduction of the Wnt5a signal is accomplished through interaction with a G protein coupled, seven transmembrane receptor, frizzled 5. The various cell lines tested show varying native levels of fzd5 transcript. In the cell line, UACC-1273, the transition from low to high Wnt5a expression is not associated with increasing amounts of the receptor. The use of an antibody to fzd5 prevents it from responding to Wnt5a and thereby attenuates or reverses the phenotypes that increased Wnt5a would normally produce. This is shown in the decreased level of phosphorylated PKC upon treatment with the anti-fzd antibody and in the decreased invasiveness of Wnt5a transfectants treated with the ant-fzd antibody (FIG. 10).

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of diagnosing an aggressive form of malignant melanoma, the method comprising the steps of:
providing a test genetic sample from a test sample tumor;
measuring Wnt5a expression in the test genetic sample;
analyzing expression of Wnt5a by statistical methods, wherein the statistical methods comprise comparing increased expression of Wnt5a in the test genetic sample to the gene expression profile of Wnt5a from a cluster of pair-matched tumor samples,
wherein increased expression of Wnt5a in the test sample compared to Wnt5a expression in the cluster of pair-matched tumor samples having less than about 3.5% invasive ability indicates the second tumor is aggressive.

2. A method of diagnosing an aggressive form of malignant melanoma, the method comprising the steps of:
measuring Wnt5a expression in a test tumor;
analyzing expression of Wnt5a in the test tumor by statistical methods, wherein the statistical methods comprise comparing increased expression of Wnt5a in the test tumor to the gene expression profile of Wnt5a from a cluster of pair-matched tumor samples,
wherein increased expression of Wnt5a in the test tumor compared to Wnt5a expression in the cluster of pair-matched tumor samples having non-detectable or no vasculogenic mimicry indicates the test tumor is aggressive; and
selecting a first treatment regimen for an individual with the test tumor if the test tumor is aggressive and a second treatment regimen if the test tumor is non-aggressive, wherein the first and second treatment regimens are not the same.

3. A method of diagnosing an aggressive form of malignant melanoma, the method comprising the steps of:
measuring Wnt5a expression in a test sample tumor;
analyzing expression of Wnt5a in the test sample tumor by statistical methods, wherein the statistical methods comprise comparing increased expression of Wnt5a in the test sample tumor to the gene expression profile of Wnt5a from a cluster of pair-matched tumor samples, wherein increased expression of Wnt5a in the test sample compared to Wnt5a expression in the cluster of pair-matched tumor sample having a cell motility of less than about 110.7 µm per day indicates the test tumor is aggressive.

4. A method of diagnosing an aggressive form of malignant melanoma, the method comprising the steps of:
providing a genetic sample from a test sample of a tumor;
analyzing expression of Wnt5a in the test sample of the tumor compared to a Wnt5a gene expression profile from a cluster of pair-matched tumor samples, wherein increased expression of Wnt5a in the test sample compared to a tumor in the gene expression profile having a particular phenotype indicates that the tumor of the test sample is aggressive.

5. The method of claim 4, wherein the phenotype is chosen from at least one of: reduced cell motility, reduced invasive ability, and non-detectable or no vasculogenic mimicry.

6. The method of claim 4, wherein analyzing comprises comparing expression of Wnt5a in the test sample of the tumor to a Wnt5a gene expression profile from a cluster of pair-matched tumor samples, wherein increased Wnt5a expression in the test sample relative to a tumor in the gene expression profile having less than about 3.5% invasive ability indicates the tumor of the test sample is aggressive.

7. The method of claim 4, wherein analyzing comprises comparing expression of Wnt5a in the test sample of the tumor to a Wnt5a gene expression profile from a cluster of pair-matched tumor samples, wherein increased Wnt5a expression in the test sample relative to a tumor in the gene expression profile having non-detectable or no vasculogenic mimicry indicates the tumor of the test sample is aggressive.

8. The method of claim 4, wherein analyzing comprises comparing expression of Wnt5a in the test sample of the tumor to a Wnt5a gene expression profile from a cluster of pair-matched tumor samples, wherein increased Wnt5a expression in the test sample relative to a tumor in the gene expression profile having a cell motility of less than about 110.7 µm per day indicates the tumor of the test sample is aggressive.

* * * * *

SEQUENCE LISTING

```
<160> NUMBER OF SEQ ID NOS: 41

<210> SEQ ID NO 1
<211> LENGTH: 489
<212> TYPE: DNA
<213> ORGANISM: Homo sapiens
<220> FEATURE:
<221> NAME/KEY: misc_feature
<222> LOCATION: (57)
<223> OTHER INFORMATION: n = gat or c
<220> FEATURE:
<221> NAME/KEY: misc_feature
<222> LOCATION: (167)
<223> OTHER INFORMATION: n = gat or c
<220> FEATURE:
<221> NAME/KEY: misc_feature
```

```
<222> LOCATION: (245)
<223> OTHER INFORMATION: n = gat or c
<220> FEATURE:
<221> NAME/KEY: misc_feature
<222> LOCATION: (268)
<223> OTHER INFORMATION: n = gat or c
<220> FEATURE:
<221> NAME/KEY: misc_feature
<222> LOCATION: (306)
<223> OTHER INFORMATION: n = gat or c
<220> FEATURE:
<221> NAME/KEY: misc_feature
<222> LOCATION: (388)
<223> OTHER INFORMATION: n = GAT or C
<220> FEATURE:
<221> NAME/KEY: misc_feature
<222> LOCATION: (443)
<223> OTHER INFORMATION: n = gat or c
<220> FEATURE:
<221> NAME/KEY: misc_feature
<222> LOCATION: (462)
<223> OTHER INFORMATION: n = gat or c
<220> FEATURE:
<221> NAME/KEY: misc_feature
<222> LOCATION: (472)..(477)
<223> OTHER INFORMATION: n = gat or c
<220> FEATURE:
<221> NAME/KEY: misc_feature
<222> LOCATION: (488)
<223> OTHER INFORMATION: n = gat or c

<400> SEQUENCE: 1
tttttttttt ttatatttat atttatattt atatatatgt atatatatat atatgtnatg      60
tacaaaagac tttgagatat caggcaccat taaaccacat ttcccccctt ataaatgcaa     120
ctgttcaagt acactgggaa cagttttaag gtacacctgc agtacantag gagaagcatg     180
agtggataat ctaaacacag gatcataaca gtgatacgct gcaacacctc tgtgaattcc     240
attanccaag ttctgtcatt aaaacatngg aaaactactg gctcctcaaa ataaaaggtt     300
ttaggnaacc aaaaatcccc taagtagtga actgttttcc aagcagagct ccctaatggt     360
tttcaatttc ctgggcctac aaccaaangg ggaccccagt tggaagctgc cgtttgggaa     420
acgtgggcca ggcatcagat cancaacacg ggggggaatc cngagagggg cncattnttg     480 aagaaggng                                                             489

<210> SEQ ID NO 2
<211> LENGTH: 4114
<212> TYPE: DNA
<213> ORGANISM: Homo sapiens

<400> SEQUENCE: 2
attaattctg gctccacttg ttgctcggcc caggttgggg agaggacgga gggtggccgc      60
agcgggttcc tgagtgaatt acccaggagg gactgagcac agcaccaact agagagggt     120 cagggggtgc gggactcgag cgagcaggaa ggaggcagcg cctggcacca gggctttgac     180
tcaacagaat tgagacacgt ttgtaatcgc tggcgtgccc cgcgcacagg atcccagcga     240
aaatcagatt tcctggtgag gttgcgtggg tggattaatt tggaaaaaga aactgcctat     300
atcttgccat caaaaaactc acggaggaga agcgcagtca atcaacagta aacttaagag     360 accccgatg ctcccctggt ttaacttgta tgcttgaaaa ttatctgaga gggaataaac      420 atctttcct tcttccctct ccagaagtcc attggaatat taagcccagg agttgctttg     480
gggatggctg gaagtgcaat gtcttccaag tccttcctag tggctttggc catatttttc     540
tccttcgccc aggttgtaat tgaagccaat tcttggtggt cgctaggtat gaataaccct     600
```

-continued

```
gttcagatgt cagaagtata tattatagga gcacagcctc tctgcagcca actggcagga      660 cttttctcaag gacagaagaa actgtgccac ttgtatcagg accacatgca gtacatcgga    720
gaaggcgcga agacaggcat caaagaatgc cagtatcaat tccgacatcg acggtggaac      780
tgcagcactg tggataacac ctctgttttt ggcagggtga tgcagatagg cagccgcgag     840
acggccttca catacgccgt gagcgcagca ggggtggtga acgccatgag ccggcgtgc      900 cgcgagggcg agctgtccac ctgcggctgc agccgcgccg cgcgccccaa ggacctgccg     960
cgggactggc tctggggcgg ctgcggcgac aacatcgact atggctaccg ctttgccaag    1020
gagttcgtgg acgcccgcga gcgggagcgc atccacgcca agggctccta cgagagtgct    1080
cgcatcctca tgaacctgca caacaacgag gccggccgca ggacggtgta caacctggct    1140
gatgtggcct gcaagtgcca tggggtgtcc ggctcatgta gcctgaagac atgctggctg    1200
cagctggcag acttccgcaa ggtgggtgat gccctgaagg agaagtacga cagcgcggcg    1260
gccatgcggc tcaacagccg gggcaagttg gtacaggtca acagccgctt caactcgccc    1320
accacacaag acctggtcta catcgacccc agccctgact actgcgtgcg caatgagagc    1380
accggctcgc tgggcacgca gggccgcctg tgcaacaaga cgtcggaggg catggatggc    1440
tgcgagctca tgtgctgcgg ccgtgggtac gaccagttca agaccgtgca gacggagcgc    1500
tgccactgca agtccactg gtgctgctac gtcaagtgca agaagtgcac ggagatcgtg     1560
gaccagtttg tgtgcaagta gtgggtgcca cccagcactc agccccgctc ccaggacccg    1620
cttatttata gaaagtacag tgattctggt ttttggtttt tagaaatatt ttttattttt    1680
ccccaagaat tgcaaccgga accattttttt ttcctgttac catctaagaa ctctgtggtt   1740
tattattaat attataatta ttatttggca ataatggggg tgggaaccac gaaaaatatt    1800
tattttgtgg atctttgaaa aggtaataca agacttcttt tggatagtat agaatgaagg    1860
gggaaataac atacccta acttagctgt gtgggacatg gtacacatcc agaaggtaaa      1920
gaaatacatt ttcttttttct caaatatgcc atcatatggg atgggtaggt tccagttgaa   1980
agagggtggt agaaatctat tcacaattca gcttctatga ccaaaatgag ttgtaaattc    2040
tctggtgcaa gataaaaggt cttgggaaaa caaaacaaaa caaaacaaac ctcccttccc    2100
cagcagggct gctagcttgc tttctgcatt ttcaaaatga aatttacaa tggaaggaca     2160 agaatgtcat attctcaagg aaaaaaggta tatcacatgt ctcattctcc tcaaatattc    2220
catttgcaga cagaccgtca tattctaata gctcatgaaa tttgggcagc agggaggaaa    2280
gtccccagaa attaaaaaat ttaaaactct tatgtcaaga tgttgatttg aagctgttat    2340
aagaattggg attccagatt tgtaaaaaga ccccaatga ttctggacac tagattttt     2400 gtttggggag gttggcttga acataaatga aatatcctgt attttcttag ggatacttgg    2460
ttagtaaatt ataatagtag aaataataca tgaatcccat tcacaggttt ctcagcccaa    2520
gcaacaaggt aattgcgtgc cattcagcac tgcaccagag cagacaacct atttgaggaa    2580
aaacagtgaa atccaccttc ctcttcacac tgagccctct ctgattcctc cgtgttgtga    2640
tgtgatgctg gccacgtttc caaacggcag ctccactggg tccccttttgg ttgtaggaca    2700 ggaaatgaaa cattaggagc tctgcttgga aaacagttca ctacttaggg attttttgttt     2760 cctaaaactt ttatttgag gagcagtagt tttctatgtt ttaatgacag aacttggcta    2820
atggaattca cagaggtgtt gcagcgtatc actgttatga tcctgtgttt agattatcca    2880
ctcatgcttc tcctattgta ctgcaggtgt accttaaaac tgttcccagt gtacttgaac    2940
agttgcattt ataagggggg aaatgtggtt taatggtgcc tgatatctca aagtcttttg    3000
```

```
tacataacat atatatatat atacatatat ataaatataa atataaatat atctcattgc   3060
agccagtgat ttagatttac agcttactct ggggttatct ctctgtctag agcattgttg   3120
tccttcactg cagtccagtt gggattattc caaaagtttt ttgagtcttg agcttgggct   3180
gtggccccgc tgtgatcata ccctgagcac gacgaagcaa cctcgtttct gaggaagaag   3240
cttgagttct gactcactga aatgcgtgtt gggttgaaga tatcttttt tcttttctgc    3300 ctcaccccctt tgtctccaac ctccatttct gttcactttg tggagagggc attacttgtt  3360
cgttatagac atggacgtta agagatattc aaaactcaga agcatcagca atgtttctct   3420
tttcttagtt cattctgcag aatggaaacc catgcctatt agaaatgaca gtacttatta   3480
attgagtccc taaggaatat tcagcccact acatagatag cttttttttt ttttttttt    3540 ttttaataag gacacctctt tccaaacagg ccatcaaata tgttcttatc tcagacttac   3600
gttgttttaa aagtttggaa agatacacat cttttcatac cccccttag gaggttgggc    3660 tttcatatca cctcagccaa ctgtggctct taatttattg cataatgata tccacatcag   3720
ccaactgtgg ctctttaatt tattgcataa tgatattcac atcccctcag ttgcagtgaa   3780
ttgtgagcaa aagatcttga agcaaaaag cactaattag tttaaaatgt cactttttg     3840 gtttttatta tacaaaaacc atgaagtact tttttattt gctaaatcag attgttcctt    3900
tttagtgact catgtttatg aagagagttg agtttaacaa tcctagcttt taaaagaaac   3960
tatttaatgt aaaatattct acatgtcatt cagatattat gtatatcttc tagccttat    4020 tctgtacttt taatgtacat atttctgtct tgcgtgattt gtatatttca ctggtttaaa   4080
aaacaaacat cgaaaggctt attccaaatg gaag                               4114
```

<210> SEQ ID NO 3
<211> LENGTH: 365
<212> TYPE: PRT
<213> ORGANISM: Homo sapiens

<400> SEQUENCE: 3

```
Met Ala Gly Ser Ala Met Ser Ser Lys Phe Phe Leu Val Ala Leu Ala
  1               5                  10                  15

Ile Phe Phe Ser Phe Ala Gln Val Val Ile Glu Ala Asn Ser Trp Trp
                 20                  25                  30

Ser Leu Gly Met Asn Asn Pro Val Gln Met Ser Glu Val Tyr Ile Ile
             35                  40                  45

Gly Ala Gln Pro Leu Cys Ser Gln Leu Ala Gly Leu Ser Gln Gly Gln
         50                  55                  60

Lys Lys Leu Cys His Leu Tyr Gln Asp His Met Gln Tyr Ile Gly Glu
 65                  70                  75                  80

Gly Ala Lys Thr Gly Ile Lys Glu Cys Gln Tyr Gln Phe Arg His Arg
                 85                  90                  95

Arg Trp Asn Cys Ser Thr Val Asp Asn Thr Ser Val Phe Gly Arg Val
                100                 105                 110

Met Gln Ile Gly Ser Arg Glu Thr Ala Phe Thr Tyr Ala Val Ser Ala
            115                 120                 125

Ala Gly Val Val Asn Ala Met Ser Arg Ala Cys Arg Glu Gly Glu Leu
        130                 135                 140

Ser Thr Cys Gly Cys Ser Arg Ala Ala Arg Pro Lys Asp Leu Pro Arg
145                 150                 155                 160

Asp Trp Leu Trp Gly Gly Cys Gly Asp Asn Ile Asp Tyr Gly Tyr Arg
                165                 170                 175
```

```
Phe Ala Lys Glu Phe Val Asp Ala Arg Glu Arg Glu Arg Ile His Ala
            180                 185                 190
Lys Gly Ser Tyr Glu Ser Ala Arg Ile Leu Met Asn Leu His Asn Asn
            195                 200                 205
Glu Ala Gly Arg Arg Thr Val Tyr Asn Leu Ala Asp Val Ala Cys Lys
            210                 215                 220
Cys His Gly Val Ser Gly Ser Cys Ser Leu Lys Thr Cys Trp Leu Gln
225                 230                 235                 240
Leu Ala Asp Phe Arg Lys Val Gly Asp Ala Leu Lys Glu Lys Tyr Asp
                245                 250                 255
Ser Ala Ala Met Arg Leu Asn Ser Arg Gly Lys Leu Val Gln Val
            260                 265                 270
Asn Ser Arg Phe Asn Ser Pro Thr Thr Gln Asp Leu Val Tyr Ile Asp
            275                 280                 285
Pro Ser Pro Asp Tyr Cys Val Arg Asn Glu Ser Thr Gly Ser Leu Gly
            290                 295                 300
Thr Gln Gly Arg Leu Cys Asn Lys Thr Ser Glu Gly Met Asp Gly Cys
305                 310                 315                 320
Glu Leu Met Cys Cys Gly Arg Gly Tyr Asp Gln Phe Lys Thr Val Gln
                325                 330                 335
Thr Glu Arg Cys His Cys Lys Phe His Trp Cys Cys Tyr Val Lys Cys
                340                 345                 350
Lys Lys Cys Thr Glu Ile Val Asp Gln Phe Val Cys Lys
            355                 360                 365

<210> SEQ ID NO 4
<211> LENGTH: 401
<212> TYPE: DNA
<213> ORGANISM: Homo sapiens
<220> FEATURE:
<221> NAME/KEY: misc_feature
<222> LOCATION: (233)
<223> OTHER INFORMATION: n = gat or c

<400> SEQUENCE: 4
atcatgcatt gcaacattta ttgatggagt tttcccaatt taatatttct catcatttcc      60
tcacatgatt agtactgcta gcggacctac taaaatttta acactgactt attattagag     120
atggcttgca tttttcctac accattccaa aggagaacat tagatgtctg tattaaattc     180
aagcaaaagt gtgagagaaa taatttcagc atgtctcagg tgtctcgctg gcncttaagg     240
tgaataaggt ggtggtgact gttctgcaga gagtttctca taagcaggtg gagcattggg     300
aaccacaggt tcacagtttt tctcttgaag agacactttg ctgtcccgat gatcaaaccc     360
ttcttgtggg catcttcctg ttaaggcaca ttgaggccaa c                         401

<210> SEQ ID NO 5
<211> LENGTH: 1524
<212> TYPE: DNA
<213> ORGANISM: Homo sapiens

<400> SEQUENCE: 5
agcagacaga ggactctcat taaggaaggt gtcctgtgcc ctgaccctac aagatgccaa      60
gagaagatgc tcacttcatc tatggttacc ccaagaaggg gcacgccac tcttacacca     120 cggctgaaga ggccgctggg atcggcatcc tgacagtgat cctgggagtc ttactgctca     180
tcggctgttg gtattgtaga agacgaaatg gatacagagc cttgatggat aaaagtcttc     240
```

-continued

```
atgttggcac tcaatgtgcc ttaacaagaa gatgcccaca agaagggttt gatcatcggg     300
acagcaaagt gtctcttcaa gagaaaaact gtgaacctgt ggttcccaat gctccacctg     360
cttatgagaa actctctgca gaacagtcac caccacctta ttcaccttaa gagccagcga     420
gacacctgag acatgctgaa attatttctc tcacacttttt gcttgaattt aatacagaca     480
tctaatgttc tcctttggaa tggtgtagga aaaatgcaag ccatctctaa taataagtca     540
gtgttaaaat tttagtaggt ccgctagcag tactaatcat gtgaggaaat gatgagaaat     600
attaaattgg gaaaactcca tcaataaatg ttgcaatgca tgatactatc tgtgccagag     660
gtaatgttag taaatccatg gtgttatttt ctgagagaca gaattcaagt gggtattctg     720
gggccatcca atttctcttt acttgaaatt tggctaataa caaactagtc aggttttcga     780
accttgaccg acatgaactg tacacagaat tgttccagta ctatgagtg ctcacaaagg     840 atacttttac aggttaagac aaagggttga ctggcctatt tatctgatca agaacatgtc     900
agcaatgtct ctttgtgctc taaaattcta ttatactaca ataatatatt gtaaagatcc     960
tatagctctt tttttttgag atggagtttc gcttttgttg cccaggctgg agtgcaatgg    1020
cgcgatcttg gctcaccata acctccgcct cccaggttca agcaattctc ctgccttagc    1080
ctcctgagta gctgggatta caggcgtgcg ccactatgcc tgactaattt tgtagtttta    1140
gtagagacgg ggtttctcca tgttggtcag gctggtctca aactcctgac ctcaggtgat    1200
ctgcccgcct cagcctccca aagtgctgga attacaggcg tgagccacca cgcctggctg    1260
gatcctatat cttaggtaag acatataacg cagtctaatt acatttcact tcaaggctca    1320
atgctattct aactaatgac aagtattttc tactaaacca gaaattggta gaaggattta    1380
aataagtaaa agctactatg tactgcctta gtgctgatgc ctgtgtactg ccttaaatgt    1440
acctatggca atttagctct cttgggttcc caaatccctc tcacaagaat gtgcagaaga    1500
aatcataaag gatcagagat tctg                                          1524
```

<210> SEQ ID NO 6
<211> LENGTH: 431
<212> TYPE: DNA
<213> ORGANISM: Homo sapiens
<220> FEATURE:
<221> NAME/KEY: misc_feature
<222> LOCATION: (47)
<223> OTHER INFORMATION: n = gat or c
<220> FEATURE:
<221> NAME/KEY: misc_feature
<222> LOCATION: (92)..(95)
<223> OTHER INFORMATION: n = gat or c
<220> FEATURE:
<221> NAME/KEY: misc_feature
<222> LOCATION: (386)
<223> OTHER INFORMATION: n = gat or c
<220> FEATURE:
<221> NAME/KEY: misc_feature
<222> LOCATION: (408)
<223> OTHER INFORMATION: n = gat or c
<220> FEATURE:
<221> NAME/KEY: misc_feature
<222> LOCATION: (427)
<223> OTHER INFORMATION: n = gat or c

<400> SEQUENCE: 6

```
taaaatttta agaaacaat gattaggttt atttgcatgt gccaggnaat atcctacatt      60
tattgttaca aaaaccatgt tatcacgtta gntgngaatt ctttagaagc accggctaaa    120
taagctttag aaatggaatg ccttcaatgg ctcaatctca gaaatggcaa aattctagga    180
cacatcaaga cctgctcttc cgctttccac tagttcccaa tctttgattt ccaggttttg    240
```

```
gcccttttcaa acccattttt tgcgtttctg aaatcaagaa tagcttgaga aatctcttca      300
ttggtgttca tcacaaatgg gaccatgttg ggataactgg gttctcttaa tggctcccca      360
gcaattaaga caaagtgggc ttctcntggg gatccctgtt ctccaccngg ggcactatca      420 cctttttncca a                                                          431
```

```
<210> SEQ ID NO 7
<211> LENGTH: 1318
<212> TYPE: DNA
<213> ORGANISM: Homo sapiens

<400> SEQUENCE: 7
ctcctctagg ccgccggccg cgaagcgctg agtcacggtg aggcgactgg acccacactc       60
tcttaacctg ccctccctgc actcgctccc ggcggctctt cgcgtcaccc ccgccgctaa      120
ggctccaggt gccgctaccg cagcgtgagt acctggggct cctgcagggg tccactagcc      180
ctccatcctc tacagctcag catcagaaca ctctcttttt agactccgat atgggtcct       240 ccaagaaagt tactctctca gtgctcagcc gggagcagtc ggaagggtt ggagcgaggg       300 tccggagaag cattggcaga cccgagttaa aaaatctgga tccgtttta ctgtttgatg       360 aatttaaagg aggtagacca ggaggatttc ctgatcatcc acatcgaggt tttgaaacag      420
tatcctacct cctggaaggg ggcagcatgg cccatgaaga cttctgtgga cacactggta      480
aaatgaaccc aggagatttg cagtggatga ctgcgggccg gggcattctg cacgctgaga      540
tgccttgctc agaggagcca gcccatggcc tacaactgtg ggttaatttg aggagctcag      600
agaagatggt ggagcctcag taccaggaac tgaaaagtga agaaatccct aaacccagta      660
aggatggtgt gacagttgct gtcatttctg gagaagccct gggaataaag tccaaggttt      720
acactcgcac accaacctta tatttggact tcaaattgga cccaggagcc aaacattccc      780
aacctatccc taaagggtgg acaagcttca tttacacgat atctggagat gtgtatattg      840
ggcccgatga tgcacaacaa aaaatagaac ctcatcacac agcagtgctt ggagaaggtg      900
acagtgtcca ggtggagaac aaggatccca agagaagcca cttgtcttaa ttgctgggg      960 agccattaag agaaccagtt atccaacatg gtccatttgt gatgaacacc aatgaagaga     1020
tttctcaagc tattcttgat ttcagaaacg caaaaaatgg gtttgaaagg ccaaaacct     1080 ggaaatcaaa gattgggaac tagtggaaag cggaagagca ggtcttgatg tgtcctagaa     1140
ttttgccatt tctgagattg agccattgaa ggcattccat ttctaaagct tatttagccg     1200
gtgcttctaa agaattccac actaacgtga taacatggtt tttgtaacaa taaatgtagg     1260
atatttcctg gcacatgcaa ataaacctaa tcattgtttc tttaaaaaaa aaaaaaaa      1318
```

```
<210> SEQ ID NO 8
<211> LENGTH: 533
<212> TYPE: DNA
<213> ORGANISM: Homo sapiens
<220> FEATURE:
<221> NAME/KEY: misc_feature
<222> LOCATION: (180)
<223> OTHER INFORMATION: n = gat or c
<220> FEATURE:
<221> NAME/KEY: misc_feature
<222> LOCATION: (360)
<223> OTHER INFORMATION: n = gat or c
<220> FEATURE:
<221> NAME/KEY: misc_feature
<222> LOCATION: (396)
<223> OTHER INFORMATION: n = gat or c
<220> FEATURE:
```

<221> NAME/KEY: misc_feature
<222> LOCATION: (465)
<223> OTHER INFORMATION: n = gat or c
<220> FEATURE:
<221> NAME/KEY: misc_feature
<222> LOCATION: (433)
<223> OTHER INFORMATION: n = gat or c
<220> FEATURE:
<221> NAME/KEY: misc_feature
<222> LOCATION: (441)
<223> OTHER INFORMATION: n = gat or c
<220> FEATURE:
<221> NAME/KEY: misc_feature
<222> LOCATION: (456)
<223> OTHER INFORMATION: n = gat or c

<400> SEQUENCE: 8

```
ttccactttc acattaaaat gaataactat attttttaacc ctctattcat aacacacaca      60
aaaaggttat attaggcttt tctacagaga gtacagaaat agaaaagtca ctactaaata     120
caaataacat tgacagttac caagaaagaa gaatttgcag ctgtcactgt gccgtagntn     180
tgatgaatgc aggttttagt ttggccatct gctccagtga ggaaggacgg atgccattat     240
ctttgggaac tgtatctttt cctattaaaa aaatgaattt ttttaactct atggggacca     300
caagccttat atatcttctc cacagggaat atgctttaaa aattaccaaa accaaatggn     360
aatataaacc cttccctatt cactggaggg aaggnggtt ttataattat cctattntcc     420
aaatttaac ctnagggctt naaggccatg gggggnatcc tcctnatggc tttcctaaan      480
gggggcncc ccnttttcnt agggccntc cttcccggcc gggccggntt ctg             533
```

<210> SEQ ID NO 9
<211> LENGTH: 1991
<212> TYPE: DNA
<213> ORGANISM: Homo sapiens

<400> SEQUENCE: 9

```
cttgctccga gagggagtcc tcgcggacgt cagccaagat tccagaatga ctatcttgac      60
ttacccctttt aaaaatcttc ccactgcatc aaaatgggcc ctcagatttt ccataagacc    120
tctgagctgt tcctcccagc tacgagctgc cccagctgtc cagaccaaaa cgaagaagac    180
gttagccaaa cccaatataa ggaatgttgt ggtggtggat ggtgttcgca ctccattttt     240
gctgtctggc acttcatata aagacctgat gccacatgat ttggctagag cagcgcttac    300
gggtttgttg catcggacca gtgtccctaa ggaagtagtt gattatatca tctttggtac    360
agttattcag gaagtgaaaa caagcaatgt ggctagagag gctgcccttg gagctggctt    420
ctctgacaag actcctgctc acactgtcac catggcttgt atctctgcca accaagccat    480
gaccacaggt gttggcttga ttgcttctgg ccagtgtgat gtgatcgtgg caggtggtgt    540
tgagttgatg tccgatgtcc ctattcgtca ctcaaggaaa atgagaaaac tgatgcttga    600
tctcaataag gccaaatcta tgggccagcg actgtcttta atctctaaat tccgatttaa    660
tttcctagca cctgagctcc ctgcggtttc tgagttctcc accagtgaga ccatgggcca    720
ctctgcagac cgactggccg ctgcctttgc tgtttctcgg ctggaacagg atgaatatgc    780
actgcgctct cacagtctag ccaagaaggc acaggatgaa ggactccttt ctgatgtggt    840
acccttcaaa gtaccaggaa aagatacagt taccaaagat aatggcatcc gtccttcctc    900
actggagcag atggccaaac taaaacctgc attcatcaag ccctacggca cagtgacagc    960
tgcaaattct tcttttcttga ctgatggtgc atctgcaatg ttaatcatgg cggaggaaaa   1020
ggctctggcc atgggttata agccgaaggc atatttgagg gatttttatgt atgtgtctca   1080
```

```
ggatccaaaa gatcaactat tacttggacc aacatatgct actccaaaag ttctagaaaa    1140
ggcaggattg accatgaatg atattgatgc ttttgaattt catgaagctt tctcgggtca    1200
gattttggca aatttaaag ccatggattc tgattggttt gcagaaaact acatgggtag     1260
aaaaaccaag gttggattgc ctcctttgga aagtttaat aactggggtg gatctctgtc    1320
cctgggacac ccatttggag ccactggctg caggttggtc atggctgctg ccaacagatt    1380
acggaaagaa ggaggccagt atggcttagt ggctgcgtgt gcagctggag gcagggcca    1440 tgctatgata gtggaagctt atccaaaata atagatccag aagaagtgac ctgaagtttc    1500
tgtgcaacac tcacactagg caatgccatt tcaatgcatt actaaatgac atttgtagtt    1560
cctagctcct cttaggaaaa cagttcttgt ggccttctat taaatagttt gcacttaagc    1620
cttgccagtg ttctgagctt ttcaataatc agtttactgc tctttcaggg atttctaagc    1680
caccagaatc tcacatgaga tgtgtgggtg gttgttttg gtctctgttg tcactaaaga    1740
ctaaatgagg gtttgcagtt gggaaagagg tcaactgaga tttggaaatc atctttgtaa    1800
tatttgcaaa ttatacttgt tcttatctgt gtcctaaaga tgtgttctct ataaaataca    1860
aaccaacgtg cctaattaat tatggaaaaa taattcagaa tctaaacacc actgaaaact    1920
tataaaaaat gtttagatac ataaatatgg tggtcagcgt taataaagtg gagaaatatt    1980
ggaaaaaaaa a                                                        1991

<210> SEQ ID NO 10
<211> LENGTH: 390
<212> TYPE: DNA
<213> ORGANISM: Homo sapiens
<220> FEATURE:
<221> NAME/KEY: misc_feature
<222> LOCATION: (11)
<223> OTHER INFORMATION: n = gat or c
<220> FEATURE:
<221> NAME/KEY: misc_feature
<222> LOCATION: (239)
<223> OTHER INFORMATION: n = gat or c
<220> FEATURE:
<221> NAME/KEY: misc_feature
<222> LOCATION: (328)
<223> OTHER INFORMATION: n = gat or c
<220> FEATURE:
<221> NAME/KEY: misc_feature
<222> LOCATION: (359)
<223> OTHER INFORMATION: n = gat or c

<400> SEQUENCE: 10
tttttttttt ntcggtctga aaaataatc cgtttaattg aaaaacctgg gaggatacta     60
ttccactccc ccagatgagg aggctgagga gaccagaccc ctacatcacc tcgtagccac    120
ttctgatact cttcacgagg cagcaggcaa agacaattcc caaaacctcg acaaaagcaa    180
ttccaagggc tgctgcagct accaccagca cattttccct cagccagccc ccaatcttnt    240
ccacacagcc ctccttatgg atcgccttct cgttgaaatt aatcccacag cccacagtaa    300
cattaatggc aggcagggag tcggggantc ggttctttcg gacatgggaa gggttttnt    360 cccaatctgt gtagttaggc aggccccaca                                    390

<210> SEQ ID NO 11
<211> LENGTH: 873
<212> TYPE: DNA
<213> ORGANISM: Homo sapiens

<400> SEQUENCE: 11
```

```
tagagagccc cggagccgcg gcgggagagg aacgcgcagc cagccttggg aagcccaggc    60
ccggcagcca tggcggtgga aggaggaatg aaatgtgtga agttcttgct ctacgtcctc   120
ctgctggcct tttgcgcctg tgcagtggga ctgattgccg tgggtgtcgg ggcacagctt   180
gtcctgagtc agaccataat ccagggggct acccctggct ctctgttgcc agtggtcatc   240
atcgcagtgg gtgtcttcct cttcctggtg gcttttgtgg gctgctgcgg ggcctgcaag   300
gagaactatt gtcttatgat cacgtttgcc atctttctgt ctcttatcat gttggtggag   360
gtggccgcag ccattgctgg ctatgtgttt agagataagg tgatgtcaga gtttaataac   420
aacttccggc agcagatgga gaattacccg aaaaacaacc acactgcttc gatcctggac   480
aggatgcagg cagattttaa gtgctgtggg gctgctaact acacagattg ggagaaaatc   540
ccttccatgt cgaagaaccg agtccccgac tcctgctgca ttaatgttac tgtgggctgt   600
gggattaatt tcaacgagaa ggcgatccat aaggagggct gtgtggagaa gattgggggc   660
tggctgagga aaaatgtgct ggtggtagct gcagcagccc ttggaattgc ttttgtcgag   720
gttttgggaa ttgtctttgc ctgctgcctc gtgaagagta tcagaagtgg ctacgaggtg   780
atgtaggggt ctggtctcct cagcctcctc atctggggga gtggaatagt atcctccagg   840 ttttttcaatt aaacggatta ttttttcaga ccg                              873
```

<210> SEQ ID NO 12
<211> LENGTH: 307
<212> TYPE: DNA
<213> ORGANISM: Homo sapiens
<220> FEATURE:
<221> NAME/KEY: misc_feature
<222> LOCATION: (65)
<223> OTHER INFORMATION: n = gat or c
<220> FEATURE:
<221> NAME/KEY: misc_feature
<222> LOCATION: (117)
<223> OTHER INFORMATION: n = gat or c
<220> FEATURE:
<221> NAME/KEY: misc_feature
<222> LOCATION: (131)
<223> OTHER INFORMATION: n = gat or c
<220> FEATURE:
<221> NAME/KEY: misc_feature
<222> LOCATION: (192)
<223> OTHER INFORMATION: n = gat or c
<220> FEATURE:
<221> NAME/KEY: misc_feature
<222> LOCATION: (207)
<223> OTHER INFORMATION: n = gat or c
<220> FEATURE:
<221> NAME/KEY: misc_feature
<222> LOCATION: (254)
<223> OTHER INFORMATION: n = gat or c
<220> FEATURE:
<221> NAME/KEY: misc_feature
<222> LOCATION: (266)
<223> OTHER INFORMATION: n = gat or c
<220> FEATURE:
<221> NAME/KEY: misc_feature
<222> LOCATION: (303)
<223> OTHER INFORMATION: n = gat or c

<400> SEQUENCE: 12

```
tttttttttt ttttcccaga gaccagaaat gtggcatttt aattgaataa cttcatactt    60
gcttnataat tgtatattta acataaataa tgtccacttg tcacatttat atttctntta   120
aacaatcaat nagtatttaa tgaattagtg tctgtacagt gaaaaataag gtagttgtta   180
aaaaaactta antttttatt ggttttnctt acataataaa aaatcagtaa ctatagccac   240
tttagggcaa ccanaaaatc ctcccngaat atataatttt ttacattgtt atattacact   300
``` ttnataa 307

<210> SEQ ID NO 13
<211> LENGTH: 4286
<212> TYPE: DNA
<213> ORGANISM: Homo sapiens

<400> SEQUENCE: 13

```
gagacattcc ggtgggggac tctggccagc ccgagcaacg tggatcctga gagcactccc      60
aggtaggcat ttgccccggt gggacgcctt gccagagcag tgtgtggcag gccccccgtgg    120
aggatcaaca cagtggctga acactgggaa ggaactggta cttggagtct ggacatctga    180
aacttggctc tgaaactgcg cagcggccac cggacgcctt ctggagcagg tagcagcatg    240
cagccgcctc caagtctgtg cggacgcgcc ctggttgcgc tggttcttgc ctgcggcctg    300
tcgcggatct ggggagagga gagaggcttc ccgcctgaca gggccactcc gcttttgcaa    360
accgcagaga taatgacgcc acccactaag accttatggc ccaagggttc caacgccagt    420
ctggcgcggt cgttggcacc tgcggaggtg cctaaaggag acaggacggc aggatctccg    480
ccacgcacca tctcccctcc cccgtgccaa ggacccatcg agatcaagga gactttcaaa    540
tacatcaaca cggttgtgtc ctgccttgtg ttcgtgctgg ggatcatcgg aactccaca    600
cttctgagaa ttatctacaa gaacaagtgc atgcgaaacg gtcccaatat cttgatcgcc    660
agcttggctc tgggagacct gctgcacatc gtcattgaca tccctatcaa tgtctacaag    720
ctgctggcag aggactggcc atttggagct gagatgtgta gctggtgcc tttcatacag    780
aaagcctccg tgggaatcac tgtgctgagt ctatgtgctc tgagtattga cagatatcga    840
gctgttgctt cttggagtag aattaaagga attggggttc caaaatggac agcagtagaa    900
attgttttga tttgggtggt ctctgtggtt ctggctgtcc ctgaagccat aggttttgat    960
ataattacga tggactacaa aggaagttat ctgcgaatct gcttgcttca tcccgttcag   1020
aagacagctt tcatgcagtt ttacaagaca gcaaaagatt ggtggctgtt cagtttctat   1080
ttctgcttgc cattggccat cactgcattt ttttatacac taatgacctg tgaaatgttg   1140
agaaagaaaa gtggcatgca gattgcttta aatgatcacc taaagcagag acgggaagtg   1200
gccaaaaccg tcttttgcct ggtccttgtc tttgccctct gctggcttcc ccttcacctc   1260
agcaggattc tgaagctcac tctttataat cagaatgatc ccaatagatg tgaactttg    1320
agctttctgt tggtattgga ctatattggt atcaacatgg cttcactgaa ttcctgcatt   1380
aacccaattg ctctgtattt ggtgagcaaa agattcaaaa actgctttaa gtcatgctta   1440
tgctgctggt gccagtcatt tgaagaaaaa cagtccttgg aggaaaagca gtcgtgctta   1500
aagttcaaag ctaatgatca cggatatgac aacttccgtt ccagtaataa atacagctca   1560
tcttgaaaga gaactattc actgtatttc attttcttta tattggaccg aagtcattaa   1620
aacaaatga acatttgcc aaacaaaac aaaaaactat gtatttgcac agcacactat    1680
taaaatatta agtgtaatta ttttaacact cacagctaca tatgacattt tatgagctgt   1740
ttacggcatg gaaagaaaat cagtgggaat taagaaagcc tcgtcgtgaa agcacttaat   1800
tttttacagt tagcacttca acatagctct taacaacttc caggatattc acacaacact   1860
taggcttaaa aatgagctca ctcagaattt ctattctttc taaaaagaga tttatttta    1920
aatcaatggg actctgatat aaaggaagaa taagtcactg taaaacagaa cttttaaatg   1980
aagcttaaat tactcaattt aaaattttaa atcctttaa aacaacttt caattaatat     2040
```

-continued

```
tatcacacta ttatcagatt gtaattagat gcaaatgaga gagcagttta gttgttgcat    2100
ttttcggaca ctggaaacat ttaaatgatc aggagggagt aacagaaaga gcaaggctgt    2160
ttttgaaaat cattcacctt tcactagaag cccaaacctc agcattctgc aatatgtaac    2220
caacatgtca caaacaagca gcatgtaaca gactggcaca tgtgccagct gaatttaaaa    2280
tataatactt ttaaaagaa aattattaca tcctttacat tcagttaaga tcaaacctca    2340
caaagagaaa tagaatgttt gaaaggctat cccaaaagac tttttgaat ctgtcattca    2400
cataccctgt gaagacaata ctatctacaa ttttttcagg attattaaaa tcttcttttt    2460
tcactatcgt agcttaaact ctgtttggtt ttgtcatctg taaatactta cctacataca    2520
ctgcatgtag atgattaaat gagggcaggc cctgtgctca tagctttacg atggagagat    2580
gccagtgacc tcataataaa gactgtgaac tgcctggtgc agtgtccaca tgacaaaggg    2640
gcaggtagca ccctctctca cccatgctgt ggttaaaatg gtttctagca tatgtataat    2700
gctatagtta aaatactatt tttcaaaatc atacagatta gtacatttaa cagctacctg    2760
taaagcttat tactaatttt tgtattattt ttgtaaatag ccaatagaaa gtttgcttg    2820
acatggtgct tttctttcat ctagaggcaa aactgctttt tgagaccgta agaacctctt    2880
agctttgtgc gttcctgcct aattttata tcttctaagc aaagtgcctt aggatagctt    2940
gggatgagat gtgtgtgaaa gtatgtacaa gagaaacgg aagagagagg aaatgaggtg    3000
gggttggagg aaacccatgg ggacagattc ccattcttag cctaacgttc gtcattgcct    3060
cgtcacatca atgcaaaagg tcctgatttt gttccagcaa aacacagtgc aatgttctca    3120
gagtgacttt cgaaataaat tgggcccaag agctttaact cggtcttaaa atatgcccaa    3180
attttactt tgtttttctt ttaataggct gggccacatg ttggaaataa gctagtaatg    3240
ttgttttctg tcaatattga atgtgatggt acagtaaacc aaacccaac aatgtggcca    3300
gaaagaaaga gcaataataa ttaattcaca caccatatgg attctattta taaatcaccc    3360
acaaacttgt tctttaattt catcccaatc acttttcag aggcctgtta tcatagaagt    3420
cattttagac tctcaatttt aaattaattt tgaatcacta atattttcac agtttattaa    3480
tatatttaat ttctatttaa attttagatt atttttatta ccatgtactg aatttttaca    3540
tcctgatacc ctttccttct ccatgtcagt atcatgttct ctaattatct tgccaaattt    3600
tgaaactaca cacaaaagc atacttgcat tatttataat aaaattgcat tcagtggctt    3660
tttaaaaaaa atgtttgatt caaaacttta acatactgat aagtaagaaa caattataat    3720
ttctttacat actcaaaacc aagatagaaa aaggtgctat cgttcaactt caaaacatgt    3780
ttcctagtat taaggacttt aatatagcaa cagacaaaat tattgttaac atggatgtta    3840
cagctcaaaa gatttataaa agattttaac ctattttctc ccttattatc cactgctaat    3900
gtggatgtat gttcaaacac cttttagtat tgatagctta catatggcca aaggaataca    3960
gtttatagca aaacatgggt atgctgtagc taactttata aaagtgtaat ataacaatgt    4020
aaaaaattat atatctggga ggatttttg gttgcctaaa gtggctatag ttactgattt    4080
tttattatgt aagcaaaacc aataaaaatt taagttttt taacaactac cttattttc    4140
actgtacaga cactaattca ttaaatacta attgattgtt taaagaaat ataaatgtga    4200
caagtggaca ttatttatgt taaatataca attatcaagc aagtatgaag ttattcaatt    4260
aaaatgccac atttctggtc tctggg                                         4286
```

<210> SEQ ID NO 14
<211> LENGTH: 395

```
<212> TYPE: DNA
<213> ORGANISM: Homo sapiens
<220> FEATURE:
<221> NAME/KEY: misc_feature
<222> LOCATION: (214)
<223> OTHER INFORMATION: n = gat or c
<220> FEATURE:
<221> NAME/KEY: misc_feature
<222> LOCATION: (268)
<223> OTHER INFORMATION: n = gat or c

<400> SEQUENCE: 14
tttttttttt tttttgcaca tcactccttt attatactga tatggaaaaa ggatttagta      60
cagttatgct cagatgaaca ctggacccat gtggcagggt caagcaacta gaacatgatt     120
cagaaatcag tgaaagatac acttggacag gaccaagagg catttcactg ccatgaaaca     180
aggcaggaag ggattctaat acacacacca gggnagcact cctgcccctc agaggtcaag     240
gagctgatcc tatattggta tgagggantg ggcttatttt ctgatgacca catgtgggga     300 cttttttcaac cgccacaagg aaaccccaga agggggttatt gttttgtatt atatatacta    360
tacttttttt aattaaaagt aaatttaaca cataa                                 395

<210> SEQ ID NO 15
<211> LENGTH: 1709
<212> TYPE: DNA
<213> ORGANISM: Homo sapiens

<400> SEQUENCE: 15
gggcggggtg ccgcatcccc agcccgccgc catggccgcc tacaaactgg tgctgatccg      60
gcacggcgag agcgcatgga acctggagaa ccgcttcagc ggctggtacg acgccgacct     120
gagcccggcg gccacgagg aggcgaagcg cggcgggcag cgctacgag atgctggcta      180 tgagtttgac atctgcttca cctcagtgca gaagagagcg atccggaccc tctggacagt     240
gctagatgcc attgatcaga tgtggctgcc agtggtgagg acttggcgcc tcaatgagcg     300
gcactatggg ggtctaaccg gtctcaataa agcagaaact gctgcaaagc atggtgaggc     360
ccaggtgaag atctggaggc gctcctatga tgtcccacca cctccgatgg agcccgacca     420
tcctttctac agcaacatca gtaaggatcg caggtatgca gacctcacag aagatcagct     480
accctcctgt gagagtctga aggatactat tgccagagct ctgcccttct ggaatgaaga     540
aatagttccc cagatcaagg aggggaaacg tgtactgatt gcagcccatg caacagcct     600 ccggggcatt gtcaagcatc tggagggtct ctctgaagag gctatcatgg agctgaacct     660
gccgactggt attcccattg tctatgaatt ggacaagaac ttgaagccta tcaagcccat     720
gcagtttctg ggggatgaag agacggtgcg caaagccatg gaagctgtgg ctgcccaggg     780
caaggccaag aagtgaaggc cggcggggag gatactgtcc ccaggagcac cctccctgcc     840
cgtcttgtcc ctctgcccct cccacctgca catgtcacac tgaccacatc tgtagacatc     900
ttgagttgta gctgcagacg gggaccagtg gctcccattt tcattttagc cattttgtcg     960
cctgcaccca ctcccttcat acaatctagt cagaatagca gttctagagc acaggttctc    1020
agtctaagct atggaaaagc tccccttatc caacagagtt taaaagtagt gacttgggtt    1080
tttgcgagtg ctttgtttac taaggacttt ggggaggaac catgctaagc catgaccagt    1140
gaggagaagc aacagagcct gtctgtcccc atgagcggag tctgtcctct gctcttctgc    1200
agtcaggtca ctgcctactg cctgggggct ctagtcattc cagtggaaga cgaatgtaac    1260
ctgcgtggtg atgtgacaac tgtttcctcc ctgaccccag aggatctggc tctaggttgg    1320
```

-continued

```
gatcaatcct gaatttcgtt atgtgttaat ttacttttat taaaaaagta tagtatatat    1380
aatacaaaac aataacccta ctggggtttc ttgtggcggt tgaaatagtc ccacatgtgg    1440
tcatcagaaa tagcattcct cataccaata taggatcagc tccttgacct ctgaggggtc    1500
aggagtgctt cctggtgtgt gtattagaat cccttcctgc cttgtttcat ggcagtgaaa    1560
tgcctcttgg tcctgtccag tgtatctttc actgatttct gaatcatgtt ctagttgctt    1620
gaccctgcca catgggtcca gtgttcatct gagcataact gtactaaatc cttttccat    1680 atcagtataa taaggagtg atgtgcaat                                      1709
```

<210> SEQ ID NO 16
<211> LENGTH: 387
<212> TYPE: DNA
<213> ORGANISM: Homo sapiens
<220> FEATURE:
<221> NAME/KEY: misc_feature
<222> LOCATION: (26)
<223> OTHER INFORMATION: n = gat or c
<220> FEATURE:
<221> NAME/KEY: misc_feature
<222> LOCATION: (90)
<223> OTHER INFORMATION: n = gat or c
<220> FEATURE:
<221> NAME/KEY: misc_feature
<222> LOCATION: (324)
<223> OTHER INFORMATION: n = gat or c
<220> FEATURE:
<221> NAME/KEY: misc_feature
<222> LOCATION: (337)
<223> OTHER INFORMATION: n = gat or c
<220> FEATURE:
<221> NAME/KEY: misc_feature
<222> LOCATION: (348)
<223> OTHER INFORMATION: n = gat or c
<220> FEATURE:
<221> NAME/KEY: misc_feature
<222> LOCATION: (368)
<223> OTHER INFORMATION: n = gat or c

<400> SEQUENCE: 16

```
ttttttttt taacaaact caaaantact tgtgctttta tttaaaaaaa aaatacaatc      60
aaggtactgt ccagaaatgt tttggaaaan aagatctctt gaaaaatcct tagttttcat   120
catcatcatc atcattatta tattaataat attaatcata tccttaaaat ggaaacagta   180
ttgcttttct ggtttctgtt gtatgaaatg taaaaaaagg gatggcttcc aatgacacat   240
ttaatctttg ctaacaaaaa taatgacaat taattataca gcttcatgta aaatcggctg   300
ggtctaaacc aacctacccc tgtncatcct ccccctntcc cattcccngg ggccacctgg   360 ggggggggnaa aaaccctttt gcgttgt                                     387
```

<210> SEQ ID NO 17
<211> LENGTH: 7560
<212> TYPE: DNA
<213> ORGANISM: Homo sapiens

<400> SEQUENCE: 17

```
accggccaca gcctgcctac tgtcacccgc ctctcccgcg cgcagataca cgccccgcc     60 tccgtgggca caaaggcagc gctgctgggg aactcggggg aacgcgcacg tgggaaccgc   120
cgcagctcca cactccaggt acttcttcca aggacctagg tctctcgccc atcggaaga    180 aaataattct ttcaagaaga tcagggacaa ctgatttgaa gtctactctg tgcttctaaa   240
tccccaattc tgctgaaagt gaatccctag agccctagag ccccagcagc acccagccaa   300
acccacctcc accatggggg ccatgactca gctgttggca ggtgtctttc ttgcttttcct  360
```

-continued

```
tgccctcgct accgaaggtg gggtcctcaa gaaagtcatc cggcacaagc gacagagtgg      420
ggtgaacgcc accctgccag aagagaacca gccagtggtg tttaaccacg tttacaacat      480
caagctgcca gtgggatccc agtgttcggt ggatctggag tcagccagtg gggagaaaga      540
cctggcaccg ccttcagagc ccagcgaaag ctttcaggag cacacagtag atggggaaaa      600
ccagattgtc ttcacacatc gcatcaacat ccccgccgg gcctgtggct gtgccgcagc       660
ccctgatgtt aaggagctgc tgagcagact ggaggagctg gagaacctgg tgtcttccct      720
gagggagcaa tgtactgcag agcaggctg ctgtctccag cctgccacag gccgcttgga       780
caccaggccc ttctgtagcg gtcggggcaa cttcagcact gaaggatgtg gctgtgtctg      840
cgaacctggc tggaaaggcc caactgctc tgagcccgaa tgtccaggca actgtcacct       900
tcgaggccgg tgcattgatg ggcagtgcat ctgtgacgac ggcttcacgg gcgaggactg      960
cagccagctg gcttgcccca gcgactgcaa tgaccagggc aagtgcgtga atggagtctg    1020
catctgtttc gaaggctacg ccggggctga ctgcagccgt gaaatctgcc cagtgccctg    1080
cagtgaggag cacggcacat gtgtagatgg cttgtgtgtg tgccacgatg gctttgcagg    1140
cgatgactgc aacaagcctc tgtgtctcaa caattgctac aaccgtggac gatgcgtgga    1200
gaatgagtgc gtgtgtgatg agggtttcac gggcgaagac tgcagtgagc tcatctgccc    1260
caatgactgc ttcgaccggg gccgctgcat caatggcacc tgctactgcg aagaaggctt    1320
cacaggtgaa gactgcggga acccacctg cccacatgcc tgccacaccc agggccggtg     1380
tgaggagggg cagtgtgtat gtgatgaggg ctttgccggt ttggactgca gcgagaagag    1440
gtgtcctgct gactgtcaca atcgtggccg ctgtgtagac gggcggtgtg agtgtgatga    1500
tggtttcact ggagctgact gtgggagct caagtgtccc aatggctgca gtggccatgg     1560
ccgctgtgtc aatgggcagt gtgtgtgtga tgagggctat actggggagg actgcagcca    1620
gctacggtgc cccaatgact gtcacagtcg gggccgctgt gtcgagggca atgtgtatg     1680 tgagcaaggc ttcaagggct atgactgcag tgacatgagc tgccctaatg actgtcacca    1740
gcacggccgc tgtgtgaatg catgtgtgt ttgtgatgac ggctacacag gggaagactg     1800
ccgggatcgc caatgcccca gggactgcag caacagggc ctctgtgtgg acggacagtg     1860
cgtctgtgag gacggcttca ccggccctga ctgtgcagaa ctctcctgtc caatgactg     1920 ccatggccag ggtcgctgtg tgaatgggca gtgcgtgtgc catgaaggat ttatgggcaa    1980
agactgcaag gagcaaagat gtcccagtga ctgtcatggc cagggccgct gcgtggacgg    2040
ccagtgcatc tgccacgagg gcttcacagg cctggactgt ggccagcact cctgccccag    2100
tgactgcaac aacttaggac aatgcgtctc gggccgctgc atctgcaacg agggctacag    2160
cggagaagac tgctcagagg tgtctcctcc caaagacctc gttgtgacag aagtgacgga    2220
agagacggtc aacctggcct gggacaatga gatgcgggtc acagagtacc ttgtcgtgta    2280
cacgcccacc cacgagggtg gtctggaaat gcagttccgt gtgcctgggg accagacgtc    2340
caccatcatc caggagctgg agcctggtgt ggagtacttt atccgtgtat ttgccatcct    2400
ggagaacaag aagagcattc ctgtcagcgc cagggtggcc acgtacttac ctgcacctga    2460
aggcctgaaa ttcaagtcca tcaaggagac atctgtggaa gtggagtggg atcctctaga    2520
cattgctttt gaaacctggg agatcatctt ccggaatatg aataaagaag atgagggaga    2580
gatcaccaaa agcctgagga ggccagagac ctcttaccgg caaactgtc tagctcctgg    2640 gcaagagtat gagatatctc tgcacatagt gaaaaacaat acccgggcc ctggcctgaa    2700
```

-continued

```
gagggtgacc accacacgct tggatgcccc cagccagatc gaggtgaaag atgtcacaga    2760
caccactgcc ttgatcacct ggttcaagcc cctggctgag atcgatggca ttgagctgac    2820
ctacggcatc aaagacgtgc caggagaccg taccaccatc gatctcacag aggacgagaa    2880
ccagtactcc atcgggaacc tgaagcctga cactgagtac gaggtgtccc tcatctcccg    2940
cagaggtgac atgtcaagca acccagccaa agagaccttc acaacaggcc tcgatgctcc    3000
caggaatctt cgacgtgttt cccagacaga taacagcatc ccctggaat ggaggaatgg    3060
caaggcagct attgacagtt acagaattaa gtatgccccc atctctggag gggaccacgc    3120
tgaggttgat gttccaaaga gccaacaagc cacaaccaaa accacactca caggtctgag    3180
gccgggaact gaatatggga ttggagtttc tgctgtgaag aagacaagg agagcaatcc    3240
agcgaccatc aacgcagcca cagagttgga cacgcccaag gaccttcagg tttctgaaac    3300
tgcagagacc agcctgaccc tgctctggaa gacaccgttg gccaaatttg accgctaccg    3360
cctcaattac agtctcccca caggccagtg ggtgggagtg cagcttccaa gaaacaccac    3420
ttcctatgtc ctgagaggcc tggaaccagg acaggagtac aatgtcctcc tgacagccga    3480
gaaaggcaga cacaagagca agcccgcacg tgtgaaggca tccactgaac aagcccctga    3540
gctggaaaac ctcaccgtga ctgaggttgg ctgggatggc ctcagactca actggaccgc    3600
ggctgaccag gcctatgagc actttatcat tcaggtgcag gaggccaaca aggtggaggc    3660
agctcggaac ctcaccgtgc tggcagcct tcgggctgtg acataccgg gcctcaaggc    3720
tgctacgcct tatacagtct ccatctatgg ggtgatccag ggctatagaa caccagtgct    3780
ctctgctgag gcctccacag gggaaactcc caatttggga gaggtcgtgg tggccgaggt    3840
gggctgggat gccctcaaac tcaactggac tgctccagaa ggggcctatg agtacttttt    3900
cattcaggtg caggaggctg acacagtaga ggcagcccag aacctcaccg tcccaggagg    3960
actgaggtcc acagacctgc ctgggctcaa agcagccact cattatacca tcaccatccg    4020
cggggtcact caggacttca gcacaacccc tctctctgtt gaagtcttga cagaggaggt    4080
tccagatatg ggaaacctca cagtgaccga ggttagctgg gatgctctca gactgaactg    4140
gaccacgcca gatggaacct atgaccagtt tactattcag gtccaggagg ctgaccaggt    4200
ggaagaggct cacaatctca cggttcctgg cagcctgcgt tccatggaaa tcccaggcct    4260
cagggctggc actccttaca cagtcaccct gcacggcgag gtcaggggcc acagcactcg    4320
accccttgct gtagaggtcg tcacagagga tctcccacag ctgggagatt tagccgtgtc    4380
tgaggttggc tgggatggcc tcagactcaa ctggaccgca gctgacaatg cctatgagca    4440
ctttgtcatt caggtgcagg aggtcaacaa agtggaggca gcccagaacc tcacgttgcc    4500
tggcagcctc agggctgtgg acatcccggg cctcgaggct gccacgcctt atagagtctc    4560
catctatggg gtgatccggg gctatagaac accagtactc tctgctgagg cctccacagc    4620
caaagaacct gaaattggaa acttaaatgt ttctgacata actcccgaga gcttcaatct    4680
ctcctggatg gctaccgatg ggatcttcga gacctttacc attgaaatta ttgattccaa    4740
taggttgctg gagactgtgg aatataatat ctctggtgct gaacgaactg cccatatctc    4800
agggctaccc cctagtactg attttattgt ctacctctct ggacttgctc ccagcatccg    4860
gaccaaaacc atcagtgcca cagccacgac agaggccctg cccctctgg aaaacctaac    4920
catttccgac attaatccct acgggttcac agtttcctgg atggcatcgg agaatgcctt    4980
tgacagcttt ctagtaacgg tggtggattc tgggaagctg ctggaccccc aggaattcac    5040
actttcagga acccagagga agctggagct tagaggcctc ataactggca ttggctatga    5100
```

```
ggttatggtc tctggcttca cccaagggca tcaaaccaag cccttgaggg ctgagattgt    5160
tacagaagcc gaaccggaag ttgacaacct tctggtttca gatgccaccc cagacggttt    5220
ccgtctgtcc tggacagctg atgaagggct cttcgacaat tttgttctca aaatcagaga    5280
taccaaaaag cagtctgagc cactggaaat aaccctactt gccccgaac gtaccaggga     5340 cttaacaggt ctcagagagg ctactgaata cgaaattgaa ctctatggaa taagcaaagg    5400
aaggcgatcc cagacagtca gtgctatagc aacaacagcc atgggctccc caaggaagt    5460 cattttctca gacatcactg aaaattcggc tactgtcagc tggagggcac ccacggccca    5520
agtggagagc ttccggatta cctatgtgcc cattacagga ggtacaccct ccatggtaac    5580 tgtgacgga accaagactc agaccaggct ggtgaaactc atacctggcg tggagtacct     5640
tgtcagcatc atcgccatga agggctttga ggaaagtgaa cctgtctcag ggtcattcac    5700
cacagctctg gatggcccat ctggcctggt gacagccaac atcactgact cagaagcctt    5760
ggccaggtgg cagccagcca ttgccactgt ggacagttat gtcatctcct acacaggcga    5820
gaaagtgcca gaaattacac gcacggtgtc cgggaacaca gtggagtatg ctctgaccga    5880
cctcgagcct gccacggaat acacactgag aatctttgca gagaaagggc cccagaagag    5940
ctcaaccatc actgccaagt tcacaacaga cctcgattct caagagact tgactgctac      6000 tgaggttcag tcggaaactg ccctccttac ctggcgaccc cccgggcat cagtcaccgg      6060 ttacctgctg gtctatgaat cagtggatgg cacagtcaag gaagtcattg tgggtccaga    6120
taccacctcc tacagcctgg cagacctgag cccatccacc cactacacag ccaagatcca    6180
ggcactcaat gggccctga ggagcaatat gatccagacc atcttcacca caattggact      6240
cctgtacccc ttccccaagg actgctccca agcaatgctg aatggagaca cgacctctgg    6300
cctctacacc atttatctga atggtgataa ggctcaggcg ctggaagtct tctgtgacat     6360
gacctctgat gggggtggat ggattgtgtt cctgagacgc aaaaacggac gcgagaactt    6420
ctaccaaaac tggaaggcat atgctgctgg atttgggac cgcagagaag aattctggct      6480
tgggctggac aacctgaaca aaatcacagc ccaggggcag tacgagctcc gggtggacct    6540
gcgggaccat ggggagacag cctttgctgt ctatgacaag ttcagcgtgg agatgccaa     6600 gactcgctac aagctgaagg tggaggggta cagtgggaca gcaggtgact ccatggccta    6660
ccacaatggc agatccttct ccacctttga caaggacaca gattcagcca tcaccaactg    6720
tgctctgtcc tacaaagggg ctttctggta caggaactgt caccgtgtca acctgatggg    6780
gagatatggg gacaataacc acagtcaggg cgttaactgg ttccactgga agggccacga    6840
acactcaatc cagtttgctg agatgaagct gagaccaagc aacttcagaa atcttgaagg    6900
caggcgcaaa cgggcataaa ttggagggac cactgggtga gagaggaata aggcggccca    6960
gagcgaggaa aggattttac caaagcatca atacaaccag cccaaccatc ggtccacacc    7020
tgggcatttg gtgagaatca aagctgacca tggatccctg gggccaacgg caacagcatg    7080
ggcctcacct cctctgtgat ttctttcttt gccaaaaga catcagtctc caacatgttt    7140
ctgttttgtt gtttgattca gcaaaaatct cccagtgaca acatcgcaat agtttttttac     7200 ttctcttagg tggctctggg atgggagagg ggtaggatgt acaggggtag tttgttttag     7260
aaccagccgt atttacatg aagctgtata attaattgtc attattttg ttagcaaaga       7320 ttaaatgtgt cattggaagc catcccttttt tttacatttc atacaacaga aaccagaaaa    7380
gcaatactgt ttccattta aggatatgat taatattatt aatataataa tgatgatgat      7440
```

-continued

| gatgatgaaa actaaggatt tttcaagaga tctttctttc caaaacattt ctggacagta | 7500 |
| cctgattgta ttttttttt aaataaaagc acaagtactt tgaaaaaaa accggaattc | 7560 |

<210> SEQ ID NO 18
<211> LENGTH: 209
<212> TYPE: DNA
<213> ORGANISM: Homo sapiens
<220> FEATURE:
<221> NAME/KEY: misc_feature
<222> LOCATION: (49)
<223> OTHER INFORMATION: n = gat or c
<220> FEATURE:
<221> NAME/KEY: misc_feature
<222> LOCATION: (86)..(89)
<223> OTHER INFORMATION: n = gat or c
<220> FEATURE:
<221> NAME/KEY: misc_feature
<222> LOCATION: (95)..(99)
<223> OTHER INFORMATION: n = gat or c

<400> SEQUENCE: 18

| ggagggtgac aacacatctc ttaggcagag cagtgacagg ctgtgcccna aagtccaaac | 60 |
| aggccaggca gagaagggca gggacagggc tcaggctgag aagaacagct ggcgtccagg | 120 |
| cagggtggcc agaacgggtt gggcacaaag gatgggcccg cagctaaagt catttggtgc | 180 |
| ggcgcntcna gcatntccnt agggaaggt | 209 |

<210> SEQ ID NO 19
<211> LENGTH: 5421
<212> TYPE: DNA
<213> ORGANISM: Homo sapiens
<220> FEATURE:
<221> NAME/KEY: misc_feature
<222> LOCATION: (2019)
<223> OTHER INFORMATION: n = gat or c
<220> FEATURE:
<221> NAME/KEY: misc_feature
<222> LOCATION: (213)..(216)
<223> OTHER INFORMATION: n = gat or c

<400> SEQUENCE: 19

| gaattccggc gccgggggcc gcccgcccgc cgcccgctgc ctgcgccgcc ggccgggcat | 60 |
| gagttagtcg cagacatgga caccaaacat ttcctgccgc tcgatttctc cacccaggtg | 120 |
| aactcctccc tcacctcccc gacggggcga ggctccatgg ctgcccccctc gctgcacccg | 180 |
| tccctgggc ctggcatcgg ctccccggga cagctgcatt ctcccatcag caccctgagc | 240 |
| tcccccatca acggcatggg cccgcctttc tcggtcatca gctcccccat gggccccac | 300 |
| tccatgtcgg tgcccaccac acccaccctg gcttcagca ctggcagccc ccagctcagc | 360 |
| tcacctatga acccgtcag cagcagcgag gacatcaagc ccccctggg cctcaatggc | 420 |
| gtcctcaagg tccccgccca cccctcagga aacatggctt ccttcaccaa gcacatctgc | 480 |
| gccatctgcg ggaccgctc ctcaggcaag cactatggag tgtacagctg cgaggggtgc | 540 |
| aagggcttct tcaagcggac ggtgcgcaag gacctgacct acacctgccg cgacaacaag | 600 |
| gactgcctga ttgacaagcg gcagcggaac cggtgccagt actgccgcta ccagaagtgc | 660 |
| ctggccatgg gcatgaagcg ggaagccgtg caggaggagc ggcagcgtgg caaggaccgg | 720 |
| aacgagaatg aggtggagtc gaccagcagc gccaacgagg acatgccggt ggagaggatc | 780 |
| ctggaggctg agctggccgt ggagcccaag accgagacct acgtggaggc aaacatgggg | 840 |
| ctgaacccca gctcgccgaa cgaccctgtc accaacattt gccaagcagc cgacaaacag | 900 |
| cttttcaccc tggtggagtg ggccaagcgg atcccacact tctcagagct gccctggac | 960 |

```
gaccaggtca tcctgctgcg ggcaggctgg aatgagctgc tcatcgcctc cttctcccac   1020
cgctccatcg ccgtgaagga cgggatcctc ctggccaccg ggctgcacgt ccaccggaac   1080
agcgcccaca cgcagggggt gggcgccatc tttgacaggg tgctgacgga gcttgtgtcc   1140
aagatgcggg acatgcagat ggacaagacg gagctgggct gcctgcgcgc catcgtcctc   1200
tttaaccctg actccaaggg gctctcgaac ccggccgagg tggaggcgct gagggagaag   1260
gtctatgcgt ccttggaggc ctactgcaag cacaagtacc cagagcagcc gggaaggttc   1320
gctaagctct tgctccgcct gccggctctg cgctccatcg ggctcaaatg cctggaacat   1380
ctcttcttct tcaagctcat cggggacaca cccattgaca ccttccttat ggagatgctg   1440
gaggcgccgc accaaatgac ttaggcctgc gggcccatcc tttgtgccca cccgttctgg   1500
ccaccctgcc tggacgccag ctgttcttct cagcctgagc cctgtccctg cccttctctg   1560
cctggcctgt ttggactttg ggcacagcc tgtcactgct ctgcctaaga gatgtgttgt   1620
caccctcctt atttctgtta ctacttgtct gtggcccagg gcagtggctt tcctgagcag   1680
cagccttcgt ggcaagaact agcgtgagcc cagccaggcg cctccccacc gggctctcag   1740
gacgccctgc cacacccacg gggcttgggc gactacaggg tcttcggccc cagccctgga   1800
gctgcaggag ttgggaacgg ggcttttgtt tccgttgctg tttatcgatg ctggttttca   1860
gaattcctgt gtggccctcc tgtctggagt gacatcttca tctgctctga atactggtgc   1920
ccagccagcc cgtgacagct ccccctaat caggagggga cagctggggg cgcaagctgg   1980
tgtgtcatca gcaaagacct cagccgcctc ggggatgana ggggactcgt ggggcaagca   2040
agctgccctg tgctctgagt gagggggaag gtagcccctt tttccaaagg taactcacag   2100
ttttgccctc gagccaatga gaacatgagc tgccctctgt gcaaggtttc ggggccacct   2160
ccaggctgca ggggcgggtc actcgccccc ctgttttctc tctgccttgg tgttctggtt   2220
tcagactccc gactccccgt tcagaccaga gtgcccagc cctcccag cctgagtctt    2280
ctccttgctc tgcggggtgg gctgagactt gtccttgttt cctgcagggc tggccctggc   2340
tcgggcaggg tggggcatca ccacctcact ggccttgctg gaggcacagg gctctgcgga   2400
cctgcagcca tctgtgaggc ccgcggggat gggggggggag gagggtggcc tgttggtttc   2460
cctcagaggg ggcaggtggc ctggagagag agggctcag gaactgggag cctggtgggt    2520
ggggcagatg ctccgcggcc tggagtggtt ctgccggggc attggtggga cccctgctca   2580
ggccttctct ctggctgcca gttgtgtcta aaagactctt ggaatctgag aacccggagt   2640
cgcagcgccc tcgggcctgg gccacacgca ggccctggtg ggaccaccca gcctggtatt   2700
gtccacggac agcgttgttc acccagagcc ttacttggga gcctcactga acgcctgctc   2760
tggttgaagg tggggtgggg gcggggcttg gggcctccct ggctcagccc agtgcggcct   2820
ggcgctcctc ccgcaggctc tgcccccggg ctccggtggt gcgggccct tcaggttga    2880
actcgcctct tttgcactgg aaggtcctcc ctttggcctg agtactttc ctgttcacgc    2940
ctcagtcccg tggacccagc ctttgtcagt ggcaggtgcc tgaacagagg gtggatgggg   3000
gggataccgg agggggtctt gtcttcccag ccgcagtcta ggaatgatgc ggggggggtgg   3060
acgccttctc catagtcttt ccccacctgg agcagggggct tcctcagtgg tgaggggagc   3120
tgcctacagg ttggaccggg aggcagtggc ttggagaggc agctttccag ccttggtggg   3180
gaagaaagtg tccattcttt gccttcctgg agctcccagc cagagctgag cttaggcacc   3240
cgagtggagc ctgcagctga gtctgtgccc gagacaggct gtcagagatt ccagaagcct   3300
```

-continued

```
ctcctcccccg ccgccctcca cccctgcctt tcagcgttgt ggatccctag aggtggcccc    3360
ctgcccgatc caccgtcctg aggcagagtg ttgagcctca tacctgtacc aggtccccgg    3420
ccagctgggc ccctcccagg cactgccagg aagcccagc tgcccctggc gggtgtggtg    3480
gaaatggcag gagggtgcag gtactcttgg ggccccagcg gtgggagtgc aaaagaccca    3540
acgccaacac ctggtgcctt ttgcagccag cgcccaccca tccgtgcccg gaccttgggg    3600
aatgcccgcg gctccagagg aaaaagccca gggacggggc ctccgttgcg gggggtcggc    3660
tgcttcttgg gaactttgtc gtttccggcg ctggctggct ggctggctgt aaagcactga    3720
agcccccccg ccgccaaccc ctgaaagcag aacctggcct ccctggccac agcagcctta    3780
cccaccgctc tacgtgtccc gggcacttcc cgcagccttc ccgtccctt ctcatcggcc    3840 ttgtagttgt acagtgctgt tggtttgaaa aggtgatgtg tggggagtgc ggctcatcac    3900
tgagtagaga ggtagaattt ctatttaacc agacctgtag tagtattacc aatccagttc    3960
aattaaggtg attttctgta attattatta ttttggtggg acaatctta atnttnctaa     4020 agatagcact aacatcagct cattagccac ctgtgcctgt ccccgccttg gcccggctgg    4080
atgaagcggc ttccccgcag ggccccccact tcccagtggc tgcttcctgg ggacccaggg    4140
caccccggca ccttcaggca cgctcctcag ctggtcacct cccggctttg ccgttcagat    4200
ggggctcctg aggctcagga gtgaagatgc cacagagccg ggctcccta ggctgcgtcg     4260 ggcatgcttg gaagctggcc tgccaggacc ttccaccctg gggcctgtgt cagccgccgg    4320
ccctccgcac cctggaagca cacggcctct gggaaggaca gccctgacct tcggttttcc    4380
gagcacggtg tttcccaaga attctgggct ggcggcctgg tggcagtgct ggagatgacc    4440
ccgagcccct ccccgtgggg cacccaggag gaccctgccg gaatgtgcag cctgtgggta    4500
gtcggctggt gtccctgtcg tggagctggg gtgcgtgatc tggtgctcgt ccacgcaggt    4560
gtgtggtgta acatgtatg tgctgtacag agagacgcgt gtggagagag ccgcacacca     4620
gcgccaccca ggaaaggcgg agcggttacc agtgttttgt gtttattttt aatcaagacg    4680
tttcccctgt tttcctataa atttgcttcg tgtaagcaag tacataagga ccctcctttg    4740
gtgaaatccg ggttcgaatg aatatctcaa ggcaggagat gcatctattt taagatgctt    4800
tggagcagac agctttagcc gttcccaatc cttagcaatg ccttagctgg dacgcatagc    4860
taatacttta gagaggatga cagatccata aagagagtaa agataagaga aaatgtctaa    4920
agcatctgga agggtaaaaa aaaaaatcta ttttgtaca aatgtaattt tatccctcat     4980
gtatacttgg atatggcggg gggagggctg ggactgtttc gtttctgctt ctagagattg    5040
aggtgaaagc ttcgtccgag aaacgccagg acagacgatg gcagaggaga gggctcctgt    5100
gacggcggcg aggcttggga ggaaaccgcc gcaatggggg tgtcttccct cggggcagga    5160
gggtgggcct gtggctttca agggttttct tcccttttcga gtaattttta aagccttgct    5220
ctgttgtgtc ctgttgccgg ctctggcctt tctgtgactg actgtgaagt ggcttctccg    5280
tacgattgtc tctgaaacat cgtggccgca ggtgcagggt ttgatggaca gtagcattag    5340
aattgtggaa aaggaaacacg caagggaga agtgtgagag gagaaacaaa atatgagcgt    5400
ttaaaataca tcgccattca g                                              5421
```

<210> SEQ ID NO 20
<211> LENGTH: 481
<212> TYPE: DNA
<213> ORGANISM: Homo sapiens
<220> FEATURE:
<221> NAME/KEY: misc_feature
<222> LOCATION: (475)..(478)
<223> OTHER INFORMATION: n = g, a, t or c

<400> SEQUENCE: 20

| | | | | | |
|---|---|---|---|---|---|
| agatgttcac | aattcagttt | attcaggcaa | catattggct | gttttcagtg | tggacagcta | 60 |
| cacttaagag | caaacatgat | gaatctattg | agaattcaga | ggtagccttt | atctgcattt | 120 |
| ttttttaaac | taaaaggtat | ttaggaacca | ccttctgtca | tcgaattatc | attaaaagct | 180 |
| tccatatcag | cagtaatgca | aggccaataa | gaacaattcc | agcaaccaca | ccagctacaa | 240 |
| ttggaatgat | gtctggacca | gtgggacact | ctggattctc | cacaacatga | accatgacct | 300 |
| cgttgttccc | attcactgaa | tacgtaaaat | agaaccaaca | gtccgtcaac | atccttctcc | 360 |
| tttacaatgg | gacacaggat | caggttggga | ccggctgggg | gtaatttgtc | ccgactttct | 420 |
| accttgggta | atgttaaaat | aggaacattc | ctgtgtgcat | gtgtccttcc | tttcnccntt | 480 |
| a | | | | | | 481 |

<210> SEQ ID NO 21
<211> LENGTH: 3614
<212> TYPE: DNA
<213> ORGANISM: Homo sapiens

<400> SEQUENCE: 21

| | | | | | |
|---|---|---|---|---|---|
| gtccgccaaa | acctgcgcgg | atagggaaga | acagcacccc | ggcgccgatt | gccgtaccaa | 60 |
| acaagcctaa | cgtccgctgg | gccccggacg | ccgcgcggaa | aagatgaatt | tacaaccaat | 120 |
| tttctggatt | ggactgatca | gttcagtttg | ctgtgtgttt | gctcaaacag | atgaaaatag | 180 |
| atgtttaaaa | gcaaatgcca | aatcatgtgg | agaatgtata | caagcagggc | caaattgtgg | 240 |
| gtggtgcaca | aattcaacat | ttttacagga | aggaatgcct | acttctgcac | gatgtgatga | 300 |
| tttagaagcc | ttaaaaaaga | agggttgccc | tccagatgac | atagaaaatc | ccagaggctc | 360 |
| caaagatata | aagaaaaata | aaaatgtaac | caaccgtagc | aaaggaacag | cagagaagct | 420 |
| caagccagag | gatattcatc | agatccaacc | acagcagttg | gttttgcgat | taagatcagg | 480 |
| ggagccacag | acatttacat | taaaattcaa | gagagctgaa | gactatccca | ttgacctcta | 540 |
| ctaccttatg | gacctgtctt | attcaatgaa | agacgatttg | gagaatgtaa | aaagtcttgg | 600 |
| aacagatctg | atgaatgaaa | tgaggaggat | tacttcggac | ttcagaattg | gatttggctc | 660 |
| atttgtggaa | aagactgtga | tgccttacat | tagcacaaca | ccagctaagc | tcaggaaccc | 720 |
| ttgcacaagt | gaacagaact | gcaccacccc | atttagctac | aaaaatgtgc | tcagtcttac | 780 |
| taataaagga | gaagtattta | atgaacttgt | tggaaaacag | cgcatatctg | gaaatttgga | 840 |
| ttctccagaa | ggtggtttcg | atgccatcat | gcaagttgca | gtttgtggat | cactgattgg | 900 |
| ctggaggaat | gttacacggc | tgctggtgtt | ttccacagat | gccgggtttc | actttgctgg | 960 |
| agatgggaaa | cttggtggca | ttgttttacc | aaatgatgga | caatgtcacc | tggaaaataa | 1020 |
| tatgtacaca | atgagccatt | attatgatta | tccttctatt | gctcaccttg | tccagaaact | 1080 |
| gagtgaaaat | aatattcaga | caatttttgc | agttactgaa | gaatttcagc | ctgtttacaa | 1140 |
| ggagctgaaa | aacttgatcc | ctaagtcagc | agtaggaaca | ttatctgcaa | attctagcaa | 1200 |
| tgtaattcag | ttgatcattg | atgcatacaa | ttcccttttc | tcagaagtca | ttttggaaaa | 1260 |
| cggcaaattg | tcagaaggag | taacaataag | ttacaaatct | tactgcaaga | acgggtgaa | 1320 |
| tggaacaggg | gaaatggaa | gaaaatgttc | caatatttcc | attggagatg | aggttcaatt | 1380 |
| tgaaattagc | ataacttcaa | ataagtgtcc | aaaaaaggat | tctgacagct | ttaaaattag | 1440 |

-continued

```
gcctctgggc tttacggagg aagtagaggt tattcttcag tacatctgtg aatgtgaatg      1500
ccaaagcgaa ggcatccctg aaagtcccaa gtgtcatgaa ggaaatggga catttgagtg      1560
tggcgcgtgc aggtgcaatg aagggcgtgt tggtagacat tgtgaatgca gcacagatga      1620
agttaacagt gaagacatgg atgcttactg caggaaagaa aacagttcag aaatctgcag      1680
taacaatgga gagtgcgtct gcggacagtg tgtttgtagg aagagggata atacaaatga      1740
aatttattct ggcaaattct gcgagtgtga taatttcaac tgtgatagat ccaatggctt      1800
aatttgtgga ggaaatggtg tttgcaagtg tcgtgtgtgt gagtgcaacc ccaactacac      1860
tggcagtgca tgtgactgtt cttttggatac tagtacttgt gaagccagca acggacagat      1920
ctgcaatggc cggggcatct gcgagtgtgg tgtctgtaag tgtacagatc cgaagtttca      1980
agggcaaacg tgtgagatgt gtcagacctg ccttggtgtc tgtgctgagc ataaagaatg      2040
tgttcagtgc agagccttca ataaaggaga aagaaagac acatgcacac aggaatgttc       2100
ctattttaac attaccaagg tagaaagtcg ggacaaatta ccccagccgg tccaacctga      2160
tcctgtgtcc cattgtaagg agaaggatgt tgacgactgt tggttctatt ttacgtattc      2220
agtgaatggg aacaacgagg tcatggttca tgttgtggag aatccagagt gtcccactgg      2280
tccagacatc attccaattg tagctggtgt ggttgctgga attgttctta ttggccttgc      2340
attactgctg atatggaagc ttttaatgat aattcatgac agaagggagt ttgctaaatt      2400
tgaaaaggag aaaatgaatg ccaaatggga cacgggtgaa atcctatttt ataagagtgc      2460
cgtaacaact gtggtcaatc cgaagtatga gggaaaatga gtactgcccg tgcaaatccc      2520
acaacactga atgcaaagta gcaatttcca tagtcacagt taggtagctt tagggcaata      2580
ttgccatggt tttactcatg tgcaggtttt gaaaatgtac aatatgtata attttttaaaa     2640 tgttttatta ttttgaaaat aatgttgtaa ttcatgccag ggactgacaa aagacttgag      2700
acaggatggt tattcttgtc agctaaggtc acattgtgcc ttttttgacct tttcttcctg     2760 gactattgaa atcaagctta ttggattaag tgatatttct atagcgattg aaagggcaat      2820
agttaaagta atgagcatga tgagagtttc tgttaatcat gtattaaaac tgattttttag    2880 ctttacatat gtcagtttgc agttatgcag aatccaaagt aaatgtcctg ctagctagtt      2940
aaggattgtt ttaaatctgt tatttttgcta tttgcctgtt agacatgact gatgacatat     3000
ctgaaagaca agtatgttga gagttgctgg tgtaaaatac gtttgaaata gttgatctac      3060
aaaggccatg ggaaaaattc agagagttag gaaggaaaaa ccaatagctt taaaacctgt      3120
gtgccatttt aagagttact taatgtttgg taacttttat gccttcactt tacaaattca      3180
agccttagat aaaagaaccg agcaattttc tgctaaaaag tccttgattt agcactattt      3240
acatacaggc catactttac aaagtatttg ctgaatgggg acctttttgag ttgaatttat     3300 tttattattt ttattttgtt taatgtctgg tgctttctat cacctcttct aatcttttaa      3360
tgtatttgtt tgcaattttg gggtaagact ttttttatgag tactttttct ttgaagtttt    3420
agcggtcaat ttgccttttt aatgaacatg tgaagttata ctgtggctat gcaacagctc      3480
tcacctacgc gagtcttact ttgagttagt gccataacag accactgtat gtttacttct      3540
caccatttga gttgcccatc ttgtttcaca ctagtcacat tcttgttta agtgccttta       3600 gttttaacag ttca                                                       3614
```

<210> SEQ ID NO 22
<211> LENGTH: 393
<212> TYPE: DNA
<213> ORGANISM: Homo sapiens
<220> FEATURE:
<221> NAME/KEY: misc_feature
<222> LOCATION: (4)
<223> OTHER INFORMATION: n = gat or c
<220> FEATURE:
<221> NAME/KEY: misc_feature
<222> LOCATION: (6)
<223> OTHER INFORMATION: n = gat or c
<220> FEATURE:
<221> NAME/KEY: misc_feature
<222> LOCATION: (7)
<223> OTHER INFORMATION: n = gat or c
<220> FEATURE:
<221> NAME/KEY: misc_feature
<222> LOCATION: (8)
<223> OTHER INFORMATION: n = gat or c
<220> FEATURE:
<221> NAME/KEY: misc_feature
<222> LOCATION: (162)
<223> OTHER INFORMATION: n = gat or c
<220> FEATURE:
<221> NAME/KEY: misc_feature
<222> LOCATION: (268)
<223> OTHER INFORMATION: n = gat or c
<220> FEATURE:
<221> NAME/KEY: misc_feature
<222> LOCATION: (345)
<223> OTHER INFORMATION: n = gat or c
<220> FEATURE:
<221> NAME/KEY: misc_feature
<222> LOCATION: (388)
<223> OTHER INFORMATION: n = gat or c

<400> SEQUENCE: 22
tagnannnta ccaggtttta ttatcttttt atcaaaaaaa atcagtaaca gacaacagtg      60
tgagaggtgc ctacagagga ggtgctcact ccaacacagc ccaagggaa gggcactggg     120 ggcagaagag gacccagcca gctgggaccc tgggttgcag tngtgacggg agctaatggc    180
cactggtgca gcaagggagg gtggttcccc tcaccgcagc cactgggtc aggaggagac     240 acgacctgcc caggctaagc caccaggnct cccctctcag gagagggagg gtcccagaca    300
acaggcccca gctggggtct catcagccct cccccattcc cccncctcc ttacccaggg     360 ggagacaagg gtcgttccag cacagctnag gct                                 393

<210> SEQ ID NO 23
<211> LENGTH: 2613
<212> TYPE: DNA
<213> ORGANISM: Homo sapiens

<400> SEQUENCE: 23
gcgcgccttc tccagtccgc ggtgccatgg cccccgcccg tctgttcgcg ctgctgctgc      60
tcttcgtagg cggagtcgcc gagtcgatcc gagagactga ggtcatcgac ccccaggacc    120
tcctagaagg ccgatacttc tccggagccc taccagacga tgaggatgta gtggggcccg    180
ggcaggaatc tgatgacttt gagctgtctg gctctggaga tctggatgac ttggaagact    240
ccatgatcgg ccctgaagtt gtccatccct tggtgcctct agataaccat atccctgaga    300
gggcagggtc tgggagccaa gtccccaccg aacccaagaa actagaggag aatgaggtta    360
tccccaagag aatctcaccc gttgaagaga gtgaggatgt gtccaacaag gtgtcaatgt    420
ccagcactgt gcagggcagc aacatctttg agagaacgga ggtcctggca gctctgattg    480
tgggtggcat cgtgggcatc ctctttgccg tcttcctgat cctactgctc atgtaccgta    540
tgaagaagaa ggatgaaggc agctatgacc tgggcaagaa acccatctac aagaaagccc    600
ccaccaatga gttctacgcg tgaagcttgc ttgtgggcac tggcttggac tttagcgggg    660

```
agggaagcca gggggattttg aagggtggac attagggtag ggtgaggtca acctaatact    720
gacttgtcag tatctccagc tctgattacc tttgaagtgt tcagaagaga cattgtcttc    780
tactgttctg ccaggttctt cttgagcttt gggcctcagt tgccctggca gaaaaatgga    840
ttcaacttgg cctttctgaa ggcaagactg ggattggatc acttcttaaa cttccagtta    900
agaatctagg tccgccctca agcccatact gaccatgcct catccagagc tcctctgaag    960
ccagggggct aacggatgtt gtgtggagtc ctggctggag gtcctccccc agtggccttc   1020
ctcccttcct ttcacagccg gtctctctgc caggaaatgg gggaaggaac tagaaccacc   1080
tgcaccttga gatgtttctg taaatgggta cttgtgatca cactacggga atctctgtgg   1140
tatatacctg gggccattct aggctctttc aagtgacttt tggaaatcaa cctttttat   1200
ttgggggga ggatggggaa aagagctgag agtttatgct gaaatggatt tatagaatat   1260
ttgtaaatct attttagtg tttgttcgtt tttaactg ttcattcctt tgtgcagagt   1320
gtatatctct gcctgggcaa gagtgtggag gtgccgaggt gtcttcattc tctcgcacat   1380
ttccacagca cctgctaagt ttgtatttaa tggtttttgt ttttgttttt gtttgttttct   1440
tgaaaatgag agaagagccg gagagatgat ttttattaat ttttttttt tttttttttt   1500
tactatttat agctttagat agggcctccc ttcccctctt cttctttgt tctctttcat   1560
taaaccctt ccccagtttt tttttatac tttaaacccc gctcctcatg gccttggccc   1620
tttctgaagc tgcttcctct tataaaatag cttttgccga acatagtttt tttttttagca   1680
gatcccaaaa tataatgaag gggatggtgg gatatttgtg tctgtgttct tataatatat   1740
tattattcttt ccttggttct agaaaaatag ataaatatat ttttttcagg aaatagtgtg   1800
gtgtttccag tttgatgttg ctgggtggtt gagtgagtga attttcatgt ggctgggtgg   1860
gttttttgcct tttttctcttg ccctgttcct ggtgccttct gatgggctg gaaatagttga   1920
ggtggatggt tctacccttt ctgccttctg tttgggaccc agctggtgtt ctttggtttg   1980
cttttcttcag gctctagggc tgtgctatcc aatacagtaa ccacatgcgg ctgtttaaag   2040
ttaagccaat taaaatcaca taagattaaa aattccttcc tcagttgcac taaccacgtt   2100
tctagaggcg tcactgtatg tagttcatgg ctactgtact gacagcgaga gcatgtccat   2160
ctgttggaca gcactattct agagaactaa actggcttaa cgagtcacag cctcagctgt   2220
gctgggacga cccttgtctc cctgggtagg ggggggggaa tggggagggg ctgatgaggc   2280
cccagctggg gcctgttgtc tgggaccctc cctctcctga gaggggaggc ctggtggctt   2340
agcctgggca ggtcgtgtct cctcctgacc ccagtggctg cggtgagggg aaccaccctc   2400
ccttgctgca ccagtggcca ttagctcccg tcaccactgc aacccagggt cccagctggc   2460
tgggtcctct tctgccccca gtgcccttcc ccttgggctg tgttggagtg agcacctcct   2520
ctgtaggcac ctctcacact gttgtctgtt actgatttt tttgataaaa agataataaa   2580
acctggtact ttctaaaaaa aaaaaaaaaa aaa                               2613

<210> SEQ ID NO 24
<211> LENGTH: 522
<212> TYPE: DNA
<213> ORGANISM: Homo sapiens
<220> FEATURE:
<221> NAME/KEY: misc_feature
<222> LOCATION: (498)
<223> OTHER INFORMATION: n = gat or c
<220> FEATURE:
<221> NAME/KEY: misc_feature
<222> LOCATION: (504)..(507)
<223> OTHER INFORMATION: n = gat or c
```

<400> SEQUENCE: 24

```
agcttacaca gtgtttattt gacactgaaa cgaagagctt ctgtacaata gaaagcacag      60
tgtgtgcctg gctctaaggc aggatgctaa gagagagaac cagggtcagc tggagaatag     120
acaaatgcag agctcagaga ggtgggacat ccagctcgac gagggagtct tgggagaagt     180
gaagcaaaga aacttatatg gaagtcatat cgttgagagc gtggtccagc tcctcgctga     240
tggctttgta cttcagtttc tgagcgtaca gctcgtcttc taagtcatca atgcttttct     300
ccaatttagt tactgacctc tccgcaaact cagcccgagt ctcagcctcc ttcagcttgt     360
cggaaaggac cttgatctct tcctcatatc tgtcttcctt ctgcgagtac ttctcagcct     420
gagcctccag tgacttcaaa gttgttcgtc acagttttca attttcttca agctcggcac     480
atttgccttc tgagagtnag ccgntcntct gcacgttcca gg                        522
```

<210> SEQ ID NO 25
<211> LENGTH: 1043
<212> TYPE: DNA
<213> ORGANISM: Homo sapiens

<400> SEQUENCE: 25

```
ccgcgcgctc gccccgccgc tcctgctgca gccccaggcc cctcgccgcc gccaccatgg      60
acgccatcaa gaagaagatg cagatgctga agctcgacaa ggagaacgcc ttggatcgag     120
ctgagcaggc ggaggccgac aagaaggcgg cggaagacag gagcaagcag ctggaagatg     180
agctggtgtc actgcaaaag aaactcaagg caccgaaga tgaactggac aaatactctg     240
aggctctcaa agatgcccag gagaagctgg agctggcaga gaaaaaggcc accgatgctg     300
aagccgacgt agcttctctg aacagacgca tccagctggt tgaggaagag tgagagtgag     360
agaggcatga aagtcattga gagtcgagcc caaaagatg aagaaaaat ggaaattcag       420
gagatccaac tgaaagaggc caagcacatt gctgaagatg ccgaccgcaa atacgaagag     480
gtggcccgta agctggtcat cattgagagc gacctggaac gtgcagagga gcgggctgag     540
ctctcagaag gcaaatgtgc cgagcttgaa gaagaattga aaactgtgac gaacaacttg     600
aagtcactgg aggctcaggc tgagaagtac tcgcagaagg aagacagata tgaggaagag     660
atcaaggtcc tttccgacaa gctgaaggag gctgagactc gggctgagtt tgcggagagg     720
tcagtaacta aattggagaa aagcattgat gacttagaag acgagctgta cgctcagaaa     780
ctgaagtaca aagccatcag cgaggagctg gaccacgctc tcaacgatat gacttccata     840
taagtttctt tgcttcactt ctcccaagac tccctcgtcg agctggatgt cccacctctc     900
tgagctctgc atttgtctat tctccagctg accctggttc tctctcttag catcctgcct     960
tagagccagg cacacactgt gctttctatt gtacagaagc tcttcgtttc agtgtcaaat    1020
aaacactgtg taagctaaaa aaa                                            1043
```

<210> SEQ ID NO 26
<211> LENGTH: 397
<212> TYPE: DNA
<213> ORGANISM: Homo sapiens
<220> FEATURE:
<221> NAME/KEY: misc_feature
<222> LOCATION: (183)
<223> OTHER INFORMATION: n = gat or c
<220> FEATURE:
<221> NAME/KEY: misc_feature
<222> LOCATION: (211)
<223> OTHER INFORMATION: n = gat or c
<220> FEATURE:

<221> NAME/KEY: misc_feature
<222> LOCATION: (279)
<223> OTHER INFORMATION: n = gat or c
<220> FEATURE:
<221> NAME/KEY: misc_feature
<222> LOCATION: (307)..(310)
<223> OTHER INFORMATION: n = gat or c
<220> FEATURE:
<221> NAME/KEY: misc_feature
<222> LOCATION: (345)..(350)
<223> OTHER INFORMATION: n = gat or c
<220> FEATURE:
<221> NAME/KEY: misc_feature
<222> LOCATION: (361)
<223> OTHER INFORMATION: n = gat or c
<220> FEATURE:
<221> NAME/KEY: misc_feature
<222> LOCATION: (380)
<223> OTHER INFORMATION: n = gat or c
<220> FEATURE:
<221> NAME/KEY: misc_feature
<222> LOCATION: (388)
<223> OTHER INFORMATION: n = gat or c

<400> SEQUENCE: 26

```
gccgtggggt gggaaagtgg gaaggtggag ttttccccag tggcagtgct tagcttggat      60
cctgagaggg agtaccaggt ggagggttgt ctcaggcacc atcctcctgc cctgggctgc     120
tggggagccc ctatcagcag gctgagcggg gctaggggtt ttgaagggc agaggacata      180
gcntccagca ggatggacct cagccgcagt naggcagcta caggaatcct tagggtctgg     240
ctgggttggg gggtcagctc ctcctgcagc tccaggggnt tcaggataac ctccaccctc     300
atccatnttn acatagagga tttcgtcagg ctcctggggc aggangcaan gcctttcagt     360
ntgttctcca aatcttcccn caactctnta aaacttt                              397
```

<210> SEQ ID NO 27
<211> LENGTH: 4986
<212> TYPE: DNA
<213> ORGANISM: Homo sapiens

<400> SEQUENCE: 27

```
gagtggagtt ctggaggaat gtttaccaga cacagagccc agagggacag cgcccagagc      60
ccagatagag agacacggcc tcactggctc agcaccaggg tcccctttccc cctcctcagc   120
tccctccctg gcccctttaa gaaagagctg atcctctcct ctcttgagtt aacccctgat     180
tgtccaggtg gcccctggct ctggcctggt gggcggaggc aaaggggag ccaggggcgg      240
agaaagggtt gcccaagtct gggagtgagg gaaggaggca ggggtgctga gaaggcggct    300
gctgggcaaa gccggtggca agggcctccc ctgccgctgt gccaggcagg cagtgccaaa    360
tccgggagc ctggagctgg ggggagggcc gggacagcc cggccctgcc ccctccccg       420
ctggagccc agcaacttct gaggaaagtt tggcacccat ggcgtggcgg tgccccagga     480
tgggcagggt cccgctggcc tggtgcttgg cgctgtgcgg ctgggcgtgc atggccccca    540
ggggcacgca ggctgaagaa agtcccttcg tgggcaaccc agggaatatc acaggtgccc    600
ggggactcac gggcacccctt cggtgtcagc tccaggttca gggagagccc ccgaggtac    660
attggcttcg ggatggacag atcctggagc tcgcggacag cacccagacc caggtgcccc    720
tgggtgagga tgaacaggat gactggatag tggtcagcca gctcagaatc acctccctgc    780
agctttccga cacgggacag taccagtgtt tggtgtttct gggacatcag accttcgtgt    840
cccagcctgg ctatgttggg ctggagggct tgccttactt cctggaggag cccgaagaca    900
ggactgtggc cgccaacacc cccttcaacc tgagctgcca agctcaggga ccccccagagc   960
```

-continued

| | |
|---|---|
| ccgtggacct actctggctc caggatgctg tcccctggc cacggctcca ggtcacggcc | 1020 |
| cccagcgcag cctgcatgtt ccagggctga acaagacatc ctctttctcc tgcgaagccc | 1080 |
| ataacgccaa gggggtcacc acatcccgca cagccaccat cacagtgctc ccccagcagc | 1140 |
| cccgtaacct ccacctggtc tcccgccaac ccacggagct ggaggtggct tggactccag | 1200 |
| gcctgagcgg catctacccc ctgacccact gcacctgca ggctgtgctg tcagacgatg | 1260 |
| ggatgggcat ccaggcggga gaaccagacc cccagagga gccctcacc tcgcaagcat | 1320 |
| ccgtgccccc ccatcagctt cggctaggca gcctccatcc tcacaccct tatcacatcc | 1380 |
| gcgtggcatg caccagcagc cagggcccct catcctggac ccactggctt cctgtggaga | 1440 |
| cgccggaggg agtgcccctg gcccccccta gaacattag tgctacgcgg aatgggagcc | 1500 |
| aggccttcgt gcattggcaa gagccccggg cgcccctgca gggtaccctg ttagggtacc | 1560 |
| ggctggcgta tcaaggccag gacacccag aggtgctaat ggacataggg ctaaggcaag | 1620 |
| aggtgaccct ggagctgcag ggggacgggt ctgtgtccaa tctgacagtg tgtgtggcag | 1680 |
| cctacactgc tgctggggat ggaccctgga gcctcccagt accctggag gcctggcgcc | 1740 |
| cagtgaagga accttcaact cctgccttct cgtggccctg gtggtatgta ctgctaggag | 1800 |
| cagtcgtggc cgctgcctgt gtcctcatct tggctctctt ccttgtccac cggcgaaaga | 1860 |
| aggagacccg ttatggagaa gtgtttgaac caacagtgga agaggtgaa ctggtagtca | 1920 |
| ggtaccgcgt gcgcaagtcc tacagtcgtc ggaccactga agctaccttg aacagcctgg | 1980 |
| gcatcagtga agagctgaag gagaagctgc gggatgtgat ggtggaccgg cacaaggtgg | 2040 |
| ccctggggaa gactctggga gaggagagt ttggagctgt gatggaaggc cagctcaacc | 2100 |
| aggacgactc catcctcaag gtggctgtga agacgatgaa gattgccatc tgcacgaggt | 2160 |
| cagagctgga ggatttcctg agtgaagcgg tctgcatgaa ggaatttgac catcccaacg | 2220 |
| tcatgaggct catcggtgtc tgtttccagg ttctgaacg agagagcttc ccagcacctg | 2280 |
| tggtcatctt acctttcatg aaacatggag acctacacag cttcctcctc tattcccggc | 2340 |
| tcggggacca gccagtgtac ctgcccactc agatgctagt gaagttcatg gcagacatcg | 2400 |
| ccagtggcat ggagtatctg agtaccaaga gattcataca ccgggacctg gcggccagga | 2460 |
| actgcatgct gaatgagaac atgtccgtgt gtgtggcgga cttcgggctc tccaagaaga | 2520 |
| tctacaatgg ggactactac cgccagggac gtatcgccaa gatgccagtc aagtggattg | 2580 |
| ccattgagag tctagctgac cgtgtctaca ccagcaagag cgatgtgtgg tccttcgggg | 2640 |
| tgacaatgtg ggagattgcc acaagaggcc aaaccccata tccgggcgtg gagaacagcg | 2700 |
| agatttatga ctatctgcgc cagggaaatc gcctgaagca gctgcggac tgtctggatg | 2760 |
| gactgtatgc cttgatgtcg cggtgctggg agctaaatcc ccaggaccgg ccaagtttta | 2820 |
| cagagctgcg ggaagatttg gagaacacac tgaaggcctt gcctcctgcc caggagcctg | 2880 |
| acgaaatcct ctatgtcaac atggatgagg gtggaggtta tcctgaaccc ctggagctg | 2940 |
| caggaggagc tgaccccca acccagccag accctaagga ttcctgtagc tgcctcactg | 3000 |
| cggctgaggt ccatcctgct ggacgctatg tcctctgccc ttccacaacc cctagccccg | 3060 |
| ctcagcctgc tgatagggc tccccagcag ccccagggca ggaggatggt gcctgagaca | 3120 |
| accctccacc tggtactccc tctcaggatc caagctaagc actgccactg ggaaaactc | 3180 |
| caccttccca cttttccacc ccacgcctta tccccacttg cagccctgtc ttcctaccta | 3240 |
| tcccacctcc atcccagaca ggtccctccc cttctctgtg cagtagcatc accttgaaag | 3300 |

-continued

```
cagtagcatc accatctgta aaaggaaggg gttggattgc aatatctgaa gccctcccag    3360
gtgttaacat tccaagactc tagagtccaa ggtttaaaga gtctagattc aaaggttcta    3420
ggtttcaaag atgctgtgag tctttggttc taaggacctg aaattccaaa gtctctaatt    3480
ctattaaagt gctaaggttc taaggcctac tttttttttt tttttttttt tttttttttt    3540
ttttgcgata gagtctcact gtgtcaccca ggctggagtg cagtggtgca atctcgcctc    3600
actgcaacct tcacctaccg agttcaagtg attttcctgc cttggcctcc caagtagctg    3660
ggattacagg tgtgtgccac cacacccggc taattttat attttagta gagacagggt     3720 ttcaccatgt tggccaggct ggtctaaaac tcctgacctc aagtgatctg cccacctcag    3780
cctcccaaag tgctgagatt acaggcatga gccactgcac tcaaccttaa gacctactgt    3840
tctaaagctc tgacattatg tggttttaga ttttctggtt ctaacatttt tgataaagcc    3900
tcaaggtttt aggttctaaa gttctaagat tctgatttta ggagctaagg ctctatgagt    3960
ctagatgttt attcttctag agttcagagt ccttaaaatg taagattata gattctaaag    4020
attctatagt tctagacatg gaggttctaa ggcctaggat tctaaaatgt gatgttctaa    4080
ggctctgaga gtctagattc tctggctgta aggctctaga tcataaggct tcaaaatgtt    4140
atcttctcaa gttctaagat tctaatgatg atcaattata gtttctgagg ctttatgata    4200
atagattctc ttgtataaga tcctagatcc taagggtcga aagctctaga atctgcaatt    4260
caaaagttcc aagagtctaa agatggagtt tctaaggtcc ggtgttctaa gatgtgatat    4320
tctaagactt actctaagat cttagattct ctgtgtctaa gattctagat cagatgctcc    4380
aagattctag atgattaaat aagattctaa cggtctgttc tgtttcaagg cactctagat    4440
tccattggtc caagattccg gatcctaagc atcaagttaa taagactctc acactcagtt    4500
gtgactaact agacaccaaa gttctaataa tttctaatgt tggacacctt taggttcttt    4560
gctssattct gcctctctag gaccatggtt aagagtccaa gaatccacat ttctaaaatc    4620
ttatagttct aggcactgta gttctaagac tcaaatgttc taagtttcta agattctaaa    4680
ggtccacagg tctagactat taggtgcaat ttcaaggttc taaccctata ctgtagtatt    4740
ctttggggtg cccctctcct tcttagctat cattgcttcc tcctcccaa ctgtgggggt     4800 gtgccccctt caagcctgtg caatgcatta gggatgcctc ctttccgcag gggatggacg    4860
atctcccacc tttcgggcca tgttgccccc gtgagccaat ccctcacctt ctgagtacag    4920
agtgtggact ctggtgcctc cagaggggct caggtcacat aaaactttgt atatcaacga    4980
aaaaaa                                                               4986
```

<210> SEQ ID NO 28
<211> LENGTH: 233
<212> TYPE: DNA
<213> ORGANISM: Homo sapiens
<220> FEATURE:
<221> NAME/KEY: misc_feature
<222> LOCATION: (14)..(15)
<223> OTHER INFORMATION: n = gat or c
<220> FEATURE:
<221> NAME/KEY: misc_feature
<222> LOCATION: (122)
<223> OTHER INFORMATION: n = gat or c
<220> FEATURE:
<221> NAME/KEY: misc_feature
<222> LOCATION: (216)
<223> OTHER INFORMATION: n = gat or c

<400> SEQUENCE: 28

```
gccatcaatg atcnntgccg gctccccaca cccatggact gcccctccgc catctaccag    60
```

```
ctcatgatgc agtgctggca gcaggagcgt gcccgccgcc ccaagttcgc tgacatcgtc    120
anatgcctgg acaagctcat tcgtgcccct gactccctca agaccctggc tgactttgac    180
ccccgcgtgt ctatccggct ccccagcacg agcggnctcg agggggtgcc cct            233

<210> SEQ ID NO 29
<211> LENGTH: 3921
<212> TYPE: DNA
<213> ORGANISM: Homo sapiens

<400> SEQUENCE: 29
cggaagttgc gcgcaggccg gcgggcggga gcggacaccg aggccggcgt gcaggcgtgc     60
gggtgtgcgg gagccgggct cggggggatc ggaccgagag cgagaagcgc ggcatggagc    120
tccaggcagc ccgcgcctgc ttcgccctgc tgtggggctg tgcgctggcc gcggccgcgg    180
cggcgcaggg caaggaagtg gtactgctgg actttgctgc agctggaggg gagctcggct    240
ggctcacaca cccgtatggc aaagggtggg acctgatgca gaacatcatg aatgacatgc    300
cgatctacat gtactccgtg tgcaacgtga tgtctggcga ccaggacaac tggctccgca    360
ccaactgggt gtaccgagga gaggctgagc gtaacaactt tgagctcaac tttactgtac    420
gtgactgcaa cagcttccct ggtgcgccag ctcctgcaag ggagactttc aacctctact    480
atgccgagtc ggacctggac tacggcacca acttccagaa gcgcctgttc accaagattg    540
acaccattgc gcccgatgag atcaccgtca gcagcgactt cgaggcacgc acgtgaagc    600 tgaacgtgga ggagcgctcc gtggggccgc tcacccgcaa aggcttctac ctggccttcc    660
aggatatcgg tgcctgtgtg gcgctgctct ccgtccgtgt ctactacaag aagtgccccg    720
agctgctgca gggcctggcc cacttccctg agaccatcgc cggctctgat gcaccttccc    780
tggccactgt ggccggcacc tgtgtggacc atgccgtggt gccaccgggg ggtgaagagc    840
cccgtatgca ctgtgcagtg gatggcgagt ggctggtgcc cattgggcag tgcctgtgcc    900
aggcaggcta cgagaaggtg gaggatgcct gccaggcctg ctcgcctgga ttttttaagt    960
ttgaggcatc tgagagcccc tgcttggagt gccctgagca cacgctgcca tcccctgagg   1020
gtgccacctc ctgcgagtgt gaggaaggct tcttccgggc acctcaggac ccagcgtcga   1080
tgccttgcac acgacccct tccgccccac actacctcac agccgtgggc atgggtgcca   1140
aggtggagct gcgctggacg ccccctcagg acagcggggg ccgcgaggac attgtctaca   1200
gcgtcacctg cgaacagtgc tggcccgagt ctggggaatg cgggcgtgt gaggccagtg   1260 tgcgctactc ggagcctcct cacggactga cccgcaccag tgtgacagtg agcgacctgg   1320
agccccacat gaactacacc ttcaccgtgg aggcccgcaa tggcgtctca ggcctggtaa   1380
ccagccgcag cttccgtact gccagtgtca gcatcaacca gacagagccc cccaaggtga   1440
ggctggaggg ccgcagcacc acctcgctta gcgtctcctg gagcatcccc cgccgcagc   1500 agagccgagt gtggaagtac gaggtcactt accgcaagaa gggagactcc aacagctaca   1560
atgtgcgccg caccgagggt ttctccgtga ccctggacga cctggcccca gacaccacct   1620
acctggtcca ggtgcaggca ctgacgcagg agggccaggg ggccggcagc aaggtgcacg   1680
aattccagac gctgtccccg gagggatctg gcaacttggc ggtgattggc ggcgtggctg   1740
tcggtgtggt cctgcttctg gtgctggcag gagttggctt ctttatccac cgcaggagga   1800
agaaccagcg tgcccgccag tccccggagg acgtttactt ctccaagtca gaacaactga   1860
agcccctgaa gacatacgtg gaccccccac acatatgagga ccccaaccag gctgtgttga   1920
```

-continued

```
agttcactac cgagatccat ccatcctgtg tcactcggca gaaggtgatc ggagcaggag    1980
agtttgggga ggtgtacaag ggcatgctga agacatcctc ggggaagaag gaggtgccgg    2040
tggccatcaa gacgctgaaa gccggctaca cagagaagca gcgagtggac ttcctcggcg    2100
aggccggcat catgggccag ttcagccacc acaacatcat ccgcctagag ggcgtcatct    2160
ccaaatacaa gcccatgatg atcatcactg agtacatgga gaatgggggcc ctggacaagt    2220
tccttcggga gaaggatggc gagttcagcg tgctgcagct ggtgggcatg ctgcggggca    2280
tcgcagctgg catgaagtac ctggccaaca tgaactatgt gcaccgtgac ctggctgccc    2340
gcaacatcct cgtcaacagc aacctggtct gcaaggtgtc tgactttggc ctgtcccgcg    2400
tgctggagga cgaccccgag gccacctaca ccaccagtgg cggcaagatc cccatccgct    2460
ggaccgcccc ggaggccatt tcctaccgga agttcacctc tgccagcgac gtgtggagct    2520
ttggcattgt catgtgggag gtgatgacct atggcgagcg ccctactggg gagttgtcca    2580
accacgaggt gatgaaagcc atcaatgatg gcttccggct ccccacaccc atggactgcc    2640
cctccgccat ctaccagctc atgatgcagt gctggcagca ggagcgtgcc cgccgcccca    2700
agttcgctga catcgtcagc atcctggaca agctcattcg tgccctgac tccctcaaga    2760
ccctggctga cttgacccc cgcgtgtcta tccggctccc cagcacgagc ggctcggagg    2820
gggtgccctt ccgcacggtg tccgagtggc tggagtccat caagatgcag cagtatacgg    2880
agcacttcat ggcggccggc tacactgcca tcgagaaggt ggtgcagatg accaacgacg    2940
acatcaagag gattgggtgt cggctgcccg gccaccagaa gcgcatcgcc tacagcctgc    3000
tgggactcaa ggaccaggtg aacactgtgg ggatccccat ctgagcctcg acagggcctg    3060
gagcccccatc ggccaagaat acttgaagaa acagagtggc ctccctgctg tgccatgctg    3120
ggccactggg gactttattt atttctagtt cttttcctcc cctgcaactt ccgctgaggg    3180
gtctcggatg acaccctggc ctgaactgag gagatgacca gggatgctgg gctgggccct    3240
cttcccctgc gagacgcaca cagctgagca cttagcaggc accgccacgt cccagcatcc    3300
ctggagcagg agccccgcca cagccttcgg acagacatat aggatattcc caagccgacc    3360
ttccctccgc cttctcccac atgaggccat ctcaggagat ggagggcttg gcccagcgcc    3420
aagtaaacag ggtacctcaa gccccatttc ctcacactaa gagggcagac tgtgaacttg    3480
actgggtgag acccaaagcg gtccctgtcc ctctagtgcc ttctttagac cctcgggccc    3540
catcctcatc cctgactggc caaacccttg ctttcctggg cctttgcaag atgcttggtt    3600
gtgttgaggt ttttaaatat atattttgta ctttgtggag agaatgtgtg tgtgtggcag    3660
ggggcccccgc cagggctggg gacagagggt gtcaaacatt cgtgagctgg ggactcaggg    3720
accggtgctg caggagtgtc ctgcccatgc cccagtcggc cccatctctc atccttttgg    3780
ataagtttct attctgtcag tgttaaagat tttgttttgt tggacatttt tttcgaatct    3840
taatttatta ttttttttat atttattgtt agaaaatgac ttatttctgc tctggaataa    3900
agttgcagat gattcaaacc g                                             3921
```

<210> SEQ ID NO 30
<211> LENGTH: 503
<212> TYPE: DNA
<213> ORGANISM: Homo sapiens
<220> FEATURE:
<221> NAME/KEY: misc_feature
<222> LOCATION: (320)
<223> OTHER INFORMATION: n = gat or c
<220> FEATURE:
<221> NAME/KEY: misc_feature

```
<222> LOCATION: (321)
<223> OTHER INFORMATION: n = gat or c
<220> FEATURE:
<221> NAME/KEY: misc_feature
<222> LOCATION: (433)
<223> OTHER INFORMATION: n = gat or c
<220> FEATURE:
<221> NAME/KEY: misc_feature
<222> LOCATION: (462)
<223> OTHER INFORMATION: n = gat or c
<220> FEATURE:
<221> NAME/KEY: misc_feature
<222> LOCATION: (485)
<223> OTHER INFORMATION: n = gat or c

<400> SEQUENCE: 30 ttttttacg ctaattggca catttgcttt atttatttat ttttaaaaca aactgggttt      60
tttgaatttt ttccttttg ttcattccat cacattgaaa aggaggaaaa caaaaatgat    120
tttgaattca ctcgatattt tggactcctc agatgaacgg aacattgcac acacacttgg   180
aacagagaga gagagagaga ggaaagtgga ctcccacagg gccacacgca ccagatcaaa   240
taacttggga tacagtgcaa gaatttccca aaatgattga atcatcatta ccaaaaactt   300
ggccataaca acaccaaggn nacaaaaaat gtttaaggcc acactgtttg acttggggat   360 cttcctgct tttttttttt ttttttaaaa tgtttgccac acaggggaga aagagggct    420 agtgggtgg ggnaagggca ggtttcacag acgtgagccg gggcagggng gggtttcggg   480
ttggngctga ggaagggta ggg                                           503

<210> SEQ ID NO 31
<211> LENGTH: 1231
<212> TYPE: DNA
<213> ORGANISM: Homo sapiens

<400> SEQUENCE: 31
gaattccaga aaagaggtgg agaggggggg aataagaaag agagagaagg aaaggagaga    60
aggcaggaag aaggcaaggg acgagacaac catgctgtgc tgtatgagaa gaaccaaaca   120
ggttgaaaaa aatgatgacg accaaaagat tgaacaagat ggtatcaaac cagaagataa   180
agctcataag gccgcaacca aaattcaggc tagcttccgt ggacacataa caaggaaaaa   240
gctcaaagga gagaagaagg atgatgtcca agctgctgag gctgaagcta ataagaagga   300
tgaagcccct gttgccgatg gggtggagaa gaagggagaa ggcaccacta ctgccgaagc   360
agccccagcc actggctcca agcctgatga gcccggcaaa gcaggagaaa ctccttccga   420
ggagaagaag ggggaggtg atgctgccac agagcaggca gcccccagg ctcctgcatc    480 ctcagaggag aaggccggct cagctgagac agaaagtgcc actaaagctt ccactgataa   540
ctcgccgtcc tccaaggctg aagatgcccc agccaaggag gagcctaaac aagccgatgt   600
gcctgctgct gtcactgctg ctgctgccac caccctgcc gcagaggatg ctgctgccaa    660
ggcaacagcc cagcctccaa cggagactgg ggagagcagc caagctgaag agaacataga   720
agctgtagat gaaaccaaac ctaaggaaag tgccggcag gacgagggta agaagagga    780 acctgaggct gaccaagaac atgcctgaac tctaagaaat ggctttccac atccccaccc   840 tccctctcc tgagcctgtc tctccctacc ctcttctcag ctccactctg aagtcccttc    900
ctgtcctgct cacgtctgtg agtctgtcct ttcccaccca ctagccctct ttctctctgt   960
gtggcaaaca tttaaaaaaa aaaaaaaaa gcaggaaaga tcccaagtca acagtgtgg   1020 cttaaacatt ttttgtttct tggtgttgtt atggcaagtt tttggtaatg atgattcaat  1080
```

-continued

| cattttggga aattcttgca ctgtatccaa gttatttgat ctggtgcgtg tggccctgtg | 1140 |
| ggagtccact ttcctctctc tctctctctc tgttccaagt gtgtgtgcaa tgttccgttc | 1200 |
| atctgaggag tccaaaatat tgagtgaatt c | 1231 |

<210> SEQ ID NO 32
<211> LENGTH: 418
<212> TYPE: DNA
<213> ORGANISM: Homo sapiens
<220> FEATURE:
<221> NAME/KEY: misc_feature
<222> LOCATION: (136)
<223> OTHER INFORMATION: n = gat or c
<220> FEATURE:
<221> NAME/KEY: misc_feature
<222> LOCATION: (353)
<223> OTHER INFORMATION: n = gat or c
<220> FEATURE:
<221> NAME/KEY: misc_feature
<222> LOCATION: (383)
<223> OTHER INFORMATION: n = gat or c
<220> FEATURE:
<221> NAME/KEY: misc_feature
<222> LOCATION: (411)
<223> OTHER INFORMATION: n = gat or c

<400> SEQUENCE: 32

| tttttttttac cgatgcaccc cacagtcagg gtgattttat ttctagaaaa ggtgacaggt | 60 |
| gctgcacgtg ggcaggagca ggtcacagtg aggcagggcc aggggcatcc ccctctcaac | 120 |
| acaacctagg cgccanagcc taccggccag gtagtagcaa gggctggccc atgtagtgag | 180 |
| cccagcatgg ggagacgctg agggcccatg gcgccaaag ccaggggca gcagcctcca | 240 |
| aacaccgaca cgccacgtc ccctggggca ggaaaggtgg atgccccagg gcacttctg | 300 |
| ttcctcctgc tgggagggcc tgggcaggct tggttttcaa ggacaccagc cgnagggagg | 360 |
| gccttgggca ggttggccag ggnattagga gggcagggga ttgggtttag ncaggga | 418 |

<210> SEQ ID NO 33
<211> LENGTH: 2910
<212> TYPE: DNA
<213> ORGANISM: Homo sapiens

<400> SEQUENCE: 33

| gcgacgcggc gcaggcggcg ggagtgcgag ctgggcccgt gtttcggccg ccgccatggc | 60 |
| cgcggtggac ctggagaagc tgcgggcgtc gggcgcgggc aaggccatcg gcgtcctgac | 120 |
| cagcggcggg gacgcgcaag gcatgaacgc tgctgtccgg gctgtgacgc gcatgggcat | 180 |
| ttatgtgggt gccaaagtct tcctcatcta cgagggctat gagggcctcg tggagggagg | 240 |
| tgagaacatc aagcaggcca actggctgag cgtctccaac atcatccagc tgggcggcac | 300 |
| tatcattggc agcgctcgct gcaaggcctt taccaccagg gaggggcgcc gggcagcggc | 360 |
| ctacaacctg gtccagcacg gcatcaccaa cctgtgcgtc atcggcgggg atggcagcct | 420 |
| cacaggtgcc aacatcttcc gcagcgagtg gggcagcctg ctggaggagc tggtggcgga | 480 |
| aggtaagatc tcagagacta cagcccggac ctactcgcac ctgaacatcg cgggcctagt | 540 |
| gggctccatc gataacgact tctgcggcac cgacatgacc atcggcacgg actcggccct | 600 |
| ccaccgcatc atggaggtca tcgatgccat caccaccact gcccagagcc accagaggac | 660 |
| cttcgtgctg gaagtgatgg gccggcactg cgggtacctg gcgctggtat ctgcactggc | 720 |
| ctcaggggcc gactggctgt tcatccccga ggctccaccc gaggacggct gggagaactt | 780 |
| catgtgtgag aggctgggtg agactcggag ccgtgggtcc cgactgaaca tcatcatcat | 840 |

-continued

```
cgctgagggt gccattgacc gcaacgggaa gcccatctcg tccagctacg tgaaggacct    900
ggtggttcag aggctgggct tcgacacccg tgtaactgtg ctgggccacg tgcagcgggg    960
agggacgccc tctgccttcg accggatcct gagcagcaag atgggcatgg aggcggtgat   1020
ggcgctgctg gaagccacgc tgacacgcc ggcctgcgtg gtcaccctct cggggaacca    1080
gtcagtgcgc ctgcccctca tggagtgcgt gcagatgacc aaggaagtgc agaaagccat   1140
ggatgacaag aggtttgacg aggccaccca gctccgtggt gggagcttcg agaacaactg   1200
gaacatttac aagctcctcg cccaccagaa gcccccaag gagaagtcta acttctccct    1260
ggccatcctg aatgtggggg ccccggcggc tggcatgaat gcggccgtgc gctcggcggt   1320
gcggaccggc atctcccatg acacacagt atacgtggtg cacgatggct tcgaaggcct    1380
agccaagggt caggtgcaag aagtaggctg gcacgacgtg gccggctggt tggggcgtgg   1440
tggctccatg ctggggacca agaggaccct gcccaagggc cagctggagt ccattgtgga   1500
gaacatccgc atctatggta ttcacgccct gctggtggtc ggtgggtttg aggcctatga   1560
aggggtgctg cagctggtgg aggctcgcgg gcgctacgag gagctctgca tcgtcatgtg   1620
tgtcatccca gccaccatca gcaacaacgt ccctggcacc gacttcagcc tgggctccga   1680
cactgctgta aatgccgcca tggagagctg tgaccgcatc aaacagtctg cctcggggac   1740
caagcgccgt gtgttcatcg tggagaccat ggggggttac tgtggctacc tggccaccgt   1800
gactggcatt gctgtggggg ccgacgccgc ctacgtcttc gaggacccct tcaacatcca   1860
cgacttaaag gtcaacgtgg agcacatgac ggagaagatg aagacagaca ttcagagggg   1920
cctggtgctg cggaacgaga gtgccatga ctactacacc acggagttcc tgtacaacct    1980
gtactcatca gagggcaagg gcgtcttcga ctgcaggacc aatgtcctgg ccacctgca    2040
gcagggtgg cgctccaacc cccttgacc ggaactatgg gaccaagctg ggggtgaagg    2100
ccatgctgtg gttgtcggag aagctgcgcg aggtttaccg caaggacgg gtgttcgcca   2160
atgccccaga ctcggcctgc gtgatcggcc tgaagaagaa ggcggtggcc ttcagccccg   2220
tcactgagct caagaaagac actgatttcg agcaccgcat gccacgggag cagtggtggc   2280
tgagcctgcg gctcatgctg aagatgctgg cacaataccg catcagtatg gccgcctacg   2340
tgtcaggga gctggagcac gtgacccgcc gcaccctgag catggacaag ggcttctgag   2400
gccagccatg cccacgcccc tccccagccc caccatgc cagcgcagcg ccagggctca    2460
gatgggcct gggctgttgt gtctggagcc tgcaggcagg tggggctgc gtccctgctc    2520
agcccatccc ctgcctctat ccctggccac ctgccaggcc tccctcgggc tggtgtcttg   2580
agaccagcct gccaggccct ccagcaggag gacagagtgc cctggggcat ccaccttcct   2640
gcccagggga cgtggcgctg tcggtgtttg gaggctgctg cccctggct ttggcgcccc    2700
atgggccctc agcgtctccc catgctgggc tcactacatg ggccagccct tgctctacct   2760
ggccggtagg ctgctggcgc ctaggttgtg ttgagagggg gatgcccctg gccctgcctc   2820
actgtgacct gctcctgccc acgtgcagca cctgtcacct tttctagaaa taaaatcacc   2880
ctgactgtgg ggtgcatcgg tctccggaga                                    2910
```

<210> SEQ ID NO 34
<211> LENGTH: 461
<212> TYPE: DNA
<213> ORGANISM: Homo sapiens

<400> SEQUENCE: 34

-continued

```
gcaatgagat aacgttttat tttaattctc accatttata tacaaacaca agtgaataaa      60
acacatcgca aaatggtaaa atttcatatt tagtatttat aggtgcatag tttcatgctc     120
acatattttt gagtattata tatattaaca aatttcacaa tacgtcatta ttcttagaca     180
gtatcattaa aagacaccta aaaatcttat aatatatgat agcaaatcac taacaacttc     240
tgaacaacag caacaaaaaa atagtgagga tttagaaata agtggtagtc acttaggtgt     300
ttttaatttg ttttaacatc gtagattgaa gccacaaaat ccacagcaca caaagaccct     360
gctaccatgt attcacttca gtgaaaggga agcaccgaaa tgctgagtgg gggcaggtac     420
agatacatca atcactgctg atggaagact tcgagataca c                         461
```

<210> SEQ ID NO 35
<211> LENGTH: 1096
<212> TYPE: DNA
<213> ORGANISM: Homo sapiens

<400> SEQUENCE: 35

```
gaattcatta gccatggatg tattcatgaa aggactttca aaggccaagg agggagttgt      60
ggctgctgct gagaaaacca aacagggtgt ggcagaagca gcaggaaaga caaagagggg    120
tgttctctat gtaggctcca aaaccaagga gggagtggtg catggtgtgg caacagtggc    180
tgagaagacc aaagagcaag tgacaaatgt tggaggagca gtggtgacgg tgtgacagc     240 agtagcccag aagacagtgg agggagcagg gagcattgca gcagccactg ctttgtcaa     300 aaaggaccag ttgggcaagg aagggtatca agactacgaa cctgaagcct aagaaatatc    360
tttgctccca gtttcttgag atctgctgac agatgttcca tcctgtacaa gtgctcagtt    420
ccaatgtgcc cagtcatgac atttctcaaa gttttttacag tgtatctcga agtcttccat    480
cagcagtgat tgaagtatct gtacctgccc ccactcagca tttcggtgct tccctttcac    540
tgaagtgaat acatggtagc agggtctttg tgtgctgtgg attttgtggc ttcaatctac    600
gatgttaaaa caaattaaaa acacctaagt gactaccact tatttctaaa tcctcactat    660
ttttttgttg ctgttgttca gaagttgtta gtgatttgct atcatatatt ataagatttt    720
taggtgtctt ttaatgatac tgtctaagaa taatgacgta ttgtgaaatt tgttaatata    780
tataatactt aaaaatatgt gagcatgaaa ctatgcacct ataaatacta aatatgaaat    840
tttaccattt tgcgatgtgt tttattcact tgtgtttgta tataaatggt gagaattaaa    900
ataaaacgtt atctcattgc aaaaatattt tattttatc ccatctcact ttaataataa     960
aaatcatgct tataagcaac atgaattaag aactgacaca aaggacaaaa atataaagtt    1020
attaatagcc atttgaagaa ggaggaattt tagaagaggt agagaaaatg gaacattaac    1080
cctacactcg gaattc                                                   1096
```

<210> SEQ ID NO 36
<211> LENGTH: 450
<212> TYPE: DNA
<213> ORGANISM: Homo sapiens
<220> FEATURE:
<221> NAME/KEY: misc_feature
<222> LOCATION: (407)
<223> OTHER INFORMATION: n = gat or c
<220> FEATURE:
<221> NAME/KEY: misc_feature
<222> LOCATION: (430)
<223> OTHER INFORMATION: n = gat or c

<400> SEQUENCE: 36

```
tttttttttg tttctaaagt acaaattcag tttattcatc tgtttatgac acagtacaca      60
```

```
ggaggcaaag tgtttcacat catagacttc acttccaact ccttggaatg ttcatttctt        120
tggcttacag gagagactag acaggaaggc caggcaatgc ttaggcaact aaaatgaggt        180
tgggggtaat gctaacgtca ccctcacagg gatggccacg gggactgtta ttcgcaagct        240
ggttttctag acctgttagc tggaagcatg gtgagcacca tttctgggac gctcaggccg        300
tgtcgggctt cagtcatctc caccacacag gtacagcagg cgcttttctg ggtaggtcgc        360
ccttagtgtc ttgctgggat attaatagta caggggactt gccgtantt  ctcttggatt       420 tcagacccan ttttcaacat gttccatttc                                         450
```

<210> SEQ ID NO 37
<211> LENGTH: 1362
<212> TYPE: DNA
<213> ORGANISM: Homo sapiens

<400> SEQUENCE: 37

```
catttgggga cgctctcagc tctcggcgca cggcccagct tccttcaaaa tgtctactgt         60
tcacgaaatc ctgtgcaagc tcagcttgga gggtgatcac tctacacccc caagtgcata       120
tgggtctgtc aaagcctata ctaactttga tgctgagcgg gatgctttga acattgaaac       180
agccatcaag accaaaggtg tggatgaggt caccattgtc aacattttga ccaaccgcag       240
caatgcacag agacaggata ttgccttcgc ctaccagaga aggaccaaaa aggaacttgc       300
atcagcactg aagtcagcct tatctggcca cctggagacg gtgattttgg gcctattgaa       360
gacacctgct cagtatgacg cttctgagct aaaagcttcc atgaagggc  tgggaaccga       420 cgaggactct ctcattgaga tcatctgctc cagaaccaac caggagctgc aggaaattaa       480
cagagtctac aaggaaatgt acaagactga tctggagaag gacattattt cggacacatc       540
tggtgacttc cgcaagctga tggttgccct ggcaaagggt agaagagcag aggatggctc       600
tgtcattgat tatgaactga ttgaccaaga tgctcgggat ctctatgacg ctggagtgaa       660
gaggaaagga actgatgttc ccaagtggat cagcatcatg accgagcgga gcgtgcccca       720
cctccagaaa gtatttgata ggtacaagag ttacagccct tatgacatgt tggaaagcat       780
caggaaagag gttaaggag  acctggaaaa tgctttcctg aacctggttc agtgcattca       840
gaacaagccc ctgtattttg ctgatcggct gtatgactcc atgaagggca aggggacgcg       900
agataaggtc ctgatcagaa tcatggtctc ccgcagtgaa gtggacatgt tgaaaattag       960
gtctgaattc aagagaaagt acggcaagtc cctgtactat tatatccagc aagacactaa      1020
gggcgactac cagaaagcgc tgctgtacct gtgtggtgga gatgactgaa gcccgacacg      1080
gcctgagcgt ccagaaatgg tgctcaccat gcttccagct aacaggtcta gaaaccagc       1140 ttgcgaataa cagtccccgt ggccatccct gtgagggtga cgttagcatt accccaacc       1200 tcattttagt tgcctaagca ttgcctggcc ttcctgtcta gtctctcctg taagccaaag      1260
aaatgaacat tccaaggagt tggaagtgaa gtctatgatg tgaaacactt tgcctcctgt      1320
gtactgtgtc ataaacagat gaataaactg aatttgtact tt                         1362
```

<210> SEQ ID NO 38
<211> LENGTH: 480
<212> TYPE: DNA
<213> ORGANISM: Homo sapiens
<220> FEATURE:
<221> NAME/KEY: misc_feature
<222> LOCATION: (311)
<223> OTHER INFORMATION: n = gat or c
<220> FEATURE:

```
<221> NAME/KEY: misc_feature
<222> LOCATION: (389)
<223> OTHER INFORMATION: n = gat or c
<220> FEATURE:
<221> NAME/KEY: misc_feature
<222> LOCATION: (454)
<223> OTHER INFORMATION: n = gat or c
<220> FEATURE:
<221> NAME/KEY: misc_feature
<222> LOCATION: (470)
<223> OTHER INFORMATION: n = gat or c

<400> SEQUENCE: 38
tttttttttt tttttttttt ttttaaaca ttagtgttca tagcttccaa gagacatgct      60
gactttcatt tcttgaggta ctctgcacat acgcaccaca tctctatctg gcctttgcat     120
ggagtgacca tagctccttc tctcttacat tgaatgtaga gaatgtagcc attgtagcag     180
cttgtgttgt cacgcttctt cttttgagca actttcttac actgaagaaa ggcagaatga     240
gtgcttcaga atgtgatttc ctactaacct gttccttgga taggcttttt agtatagtat     300 ttttttttg ncatttctc catcagcaac cagggagact gcacctgatg gaaaagatat       360
atgactgctt catgacattc ctaaactanc tttttttatt ccacatctac gttttggtg      420 gagtccctt tgcatcattg ttttaaggat gatnaaaaaa aaatatcacn agggggaat       480

<210> SEQ ID NO 39
<211> LENGTH: 1597
<212> TYPE: DNA
<213> ORGANISM: Homo sapiens

<400> SEQUENCE: 39
aacaaactgc acccactgaa ctccgcagct agcatccaaa tcagcccttg agatttgagg     60
ccttggagac tcaggagttt tgagagcaaa atgacaacac ccagaaattc agtaaatggg    120
actttcctgg cagagccaat gaaaggccct attgctatgc aatctggtcc aaaaccactc    180
ttcaggagga tgtcttcact ggtgggcccc acgcaaagct tcttcatgag ggaatctaag    240
actttggggg ctgtccagat tatgaatggg ctcttccaca ttgccctggg gggtcttctg    300
atgatcccag cagggatcta tgcacccatc tgtgtgactg tgtggtaccc tctctgggga    360
ggcattatgt atattatttc cggatcactc ctggcagcaa cggagaaaaa ctccaggaag    420
tgtttggtca aggaaaaat gataatgaat tcattgagcc tctttgctgc catttctgga     480
atgattcttt caatcatgga catacttaat attaaaattt cccatttttt aaaaatggag    540
agtctgaatt ttattagagc tcacacacca tatattaaca tatacaactg tgaaccagct    600
aatccctctg agaaaaactc cccatctacc caatactgtt acagcataca atctctgttc    660
ttgggcattt tgtcagtgat gctgatcttt gccttcttcc aggaacttgt aatagctggc    720
atcgttgaga atgaatggaa aagaacgtgc tccagaccca aatctaacat agttctcctg    780
tcagcagaag aaaaaaaaga acagactatt gaaataaaag aagaagtggt tgggctaact    840
gaaacatctt cccaaccaaa gaatgaagaa gacattgaaa ttattccaat ccaagaagag    900
gaagaagaag aaacagagac gaactttcca gaacctcccc aagatcagga atcctcacca    960
atagaaaatg acagctctcc ttaagtgatt tcttctgttt tctgtttcct tttttaaaca   1020
ttagtgttca tagcttccaa gagacatgct gactttcatt tcttgaggta ctctgcacat   1080
acgcaccaca tctctatctg gcctttgcat ggagtgacca tagctccttc tctcttacat   1140
tgaatgtaga gaatgtagcc attgtagcag cttgtgttgt cacgcttctt cttttgagca   1200
actttcttac actgaagaaa ggcagaatga gtgcttcaga atgtgatttc ctactaacct   1260
```

```
gttccttgga taggctttttt agtatagtat ttttttttgt catttctcc atcagcaacc      1320 agggagactg cacctgatgg aaaagatata tgactgcttc atgacattcc taaactatct      1380 ttttttttatt ccacatctac gttttggtg gagtcccttt tgcatcattg ttttaaggat      1440
gataaaaaaa aataacaac tagggacaat acagaaccca ttccatttat ctttctacag      1500
ggctgacatt gtggcacatt cttagagtta ccacacccca tgagggaagc tctaaatagc      1560
caacacccat ctgtttttg taaaaacagc atagctt                                 1597

<210> SEQ ID NO 40
<211> LENGTH: 434
<212> TYPE: DNA
<213> ORGANISM: Homo sapiens
<220> FEATURE:
<221> NAME/KEY: misc_feature
<222> LOCATION: (146)..(148)
<223> OTHER INFORMATION: n = gat or c
<220> FEATURE:
<221> NAME/KEY: misc_feature
<222> LOCATION: (347)
<223> OTHER INFORMATION: n = gat or c
<220> FEATURE:
<221> NAME/KEY: misc_feature
<222> LOCATION: (411)..(413)
<223> OTHER INFORMATION: n = gat or c
<220> FEATURE:
<221> NAME/KEY: misc_feature
<222> LOCATION: (421)
<223> OTHER INFORMATION: n = gat or c

<400> SEQUENCE: 40
aagtgaacat taaccattta ttcaaagtta tacaagaatt tgacggatta aagtcttcta        60
tgacataaag ccatttcaaa tagtttcatg tctcagctga gcaggaggag aggggggtgaa      120 agaataagtg agtaggcccc gttggnnangc tagacagtaa aaacagactc aacagcagcc      180
gcccccagcc tgctgtcctc cctgattgcc tgcatgtgtt gcattggtag cagcatgctg       240
acgggccaat tttaatgcca tttgcctcat tattaatgtc aaagactcct tcttgaattt       300
tttcataaat ttcttttgct gtattaataa atgcctcttc tacattngga agcagtctta       360
gcagacgttt ccatgaagat gagtccatgg tcccgtggca aaaggcttca ncnttccttc       420 nttttttttac ttct                                                         434

<210> SEQ ID NO 41
<211> LENGTH: 1148
<212> TYPE: DNA
<213> ORGANISM: Homo sapiens

<400> SEQUENCE: 41
gctcggtcgg gcgctgtctc cctcggctct gcgggtgtca gttcgtccgg cttcctcaca        60 gccccctcact cccggcggct gacagcagca gcggcggcgg cgggcggcgc ctggcgtttc      120
gaggctgagc ggcaccgggg ttggggcgcg gaggaggagc agcagcggga ggaggagccg       180
tgtgccctgg cactgagcgg ccgcggccat ggcgtacgcc tatctcttca agtacatcat       240
aatcggcgac acaggtgttg gtaaatcatg cttattgcta cagtttacag acaagaggtt      300
tcagccagtg catgacctta ctattggtgt agagttcggt gctcgaatga taactattga       360
tgggaaacag ataaaacttc agatatggga tacggcaggg caagaatcct ttcgttccat       420
cacaaggtcg tattcagag gtgcagcagg agctttacta gtttacgata ttacacggag        480
agatacattc aaccacttga caacctggtt agaagatgcc cgccagcatt ccaattccaa       540
```

```
catggtcatt atgcttattg gaaataaaag tgatttagaa tctagaagag aagtaaaaaa    600
agaagaaggt gaagcttttg cacgagaaca tggactcatc ttcatggaaa cgtctgctaa    660
gactgcttcc aatgtagaag aggcatttat taatacagca aaagaaattt atgaaaaaat    720
tcaagaagga gtctttgaca ttaataatga ggcaaatggc attaaaattg gccctcagca    780
tgctgctacc aatgcaacac atgcaggcaa tcagggagga cagcaggctg ggggcggctg    840
ctgttgagtc tgttttact gtctagctgc ccaacggggc ctactcactt attctttcac     900
cccctctcct cctgctcagc tgagacatga aactatttga aatggcttta tgtcacagaa    960
gactttaatc cgtcaaattc ttgtataact ttgaataaat ggttaatgtt cacttaaaag    1020
acagattttg gagattgtat tcatatctat ttgcatttga tttctaggtc aattgatgtg    1080
attatttttg ttaaatgttg tcttgtgccc ttaactacga actgaattgt attaaacact    1140
acaaagtc                                                             1148
```